US012595489B2

(12) United States Patent
Lu et al.

(10) Patent No.: US 12,595,489 B2
(45) Date of Patent: Apr. 7, 2026

(54) STERILE GENES AND RELATED CONSTRUCTS AND APPLICATIONS THEREOF

(71) Applicants: PIONEER OVERSEAS CORPORATION, Johnston, IA (US); SINOBIOWAY BIO-AGRICULTURE GROUP CO. LTD., Beijing (CN)

(72) Inventors: Guihua Lu, San Diego, CA (US); Guanfan Mao, Beijing (CN); Guokui Wang, Beijing (CN); Wei Wang, Beijing (CN); Huanhuan Ding, Beijing City (CN); Yuzhen Zheng, Zhengzhou City (CN); Marc C Albertsen, Grimes, IA (US); Tim Fox, Des Moines, IA (US)

(73) Assignees: PIONEER OVERSEAS CORPORATION; SINOBIOWAY BIO-AGRICULTURE GROUP CO. LTD. (CN)

( * ) Notice: Subject to any disclaimer, the term of this patent is extended or adjusted under 35 U.S.C. 154(b) by 219 days.

(21) Appl. No.: 17/597,380

(22) PCT Filed: Jul. 5, 2019

(86) PCT No.: PCT/CN2019/094829
§ 371 (c)(1),
(2) Date: Jan. 4, 2022

(87) PCT Pub. No.: WO2021/003592
PCT Pub. Date: Jan. 14, 2021

(65) Prior Publication Data
US 2022/0275383 A1 Sep. 1, 2022

(51) Int. Cl.
*C12N 15/82* (2006.01)
*C07K 14/415* (2006.01)
(52) U.S. Cl.
CPC .......... *C12N 15/829* (2013.01); *C07K 14/415* (2013.01)
(58) Field of Classification Search
CPC .................................................. C12N 15/829
See application file for complete search history.

(56) References Cited

U.S. PATENT DOCUMENTS 6,559,357 B1 * 5/2003 Fischer ................ C12N 15/827
536/23.6
8,299,318 B2 * 10/2012 Brover ................... A23L 27/10
536/23.6

FOREIGN PATENT DOCUMENTS

CN         103834684 A    6/2014
WO       2008/002445 A2   1/2008

OTHER PUBLICATIONS

Berka et al, 2022, J. Exp. Bot. 73:1894-1909.*
Anonymous: NCBI_GenBank: XM_020319314.1, Feb. 24, 2017 (Feb. 24, 2017).
Anonymous: NCBI_GenBank: XM_020295943.1, Feb. 24, 2017 (Feb. 24, 2017).
Anonymous: NCBI_GenBank: XM_020308017.1, Feb. 24, 2017 (Feb. 24, 2017).
Anonymous: NCBI_GenBank: XM_015777617.2, Aug. 7, 2018 (Aug. 7, 2018).
Anonymous: NCBI_GenBank: XM_015775442.2, Aug. 7, 2018 (Aug. 7, 2018).
Jia, L.; et al.: NCBI_GenBank: AY459336.1, Jul. 27, 2016 (Jul. 27, 2016).
Ma, L.; et al.: NCBI_GenBank: CL975429.1, Feb. 4, 2014 (Feb. 4, 2014).
Schnable, P. S.; et al.: NCBI_GenBank: NM_001143423.1, Jun. 25, 2017 (Jun. 25, 2017).
International Search Report and Written Opinion for International Application No. PCT/CN2019/094829, Mailed Apr. 2, 2020.
International Preliminary Report on Patentability for International Application No. PCT/CN2019/094829, mailed Jan. 20, 2022, 06 Pages.

* cited by examiner

*Primary Examiner* — Anne Kubelik

(57) ABSTRACT

Isolated polynucleotides and polypeptides, and recombinant DNA constructs useful for regulating plant sterility are provided, and methods utilizing these recombinant DNA constructs are also provided. Compositions comprising these recombinant DNA constructs or a modified endogenous sterile gene are further provided.

3 Claims, 10 Drawing Sheets

Specification includes a Sequence Listing.

Fig.1 Relative expression levels of OsZOS3-17 transgene

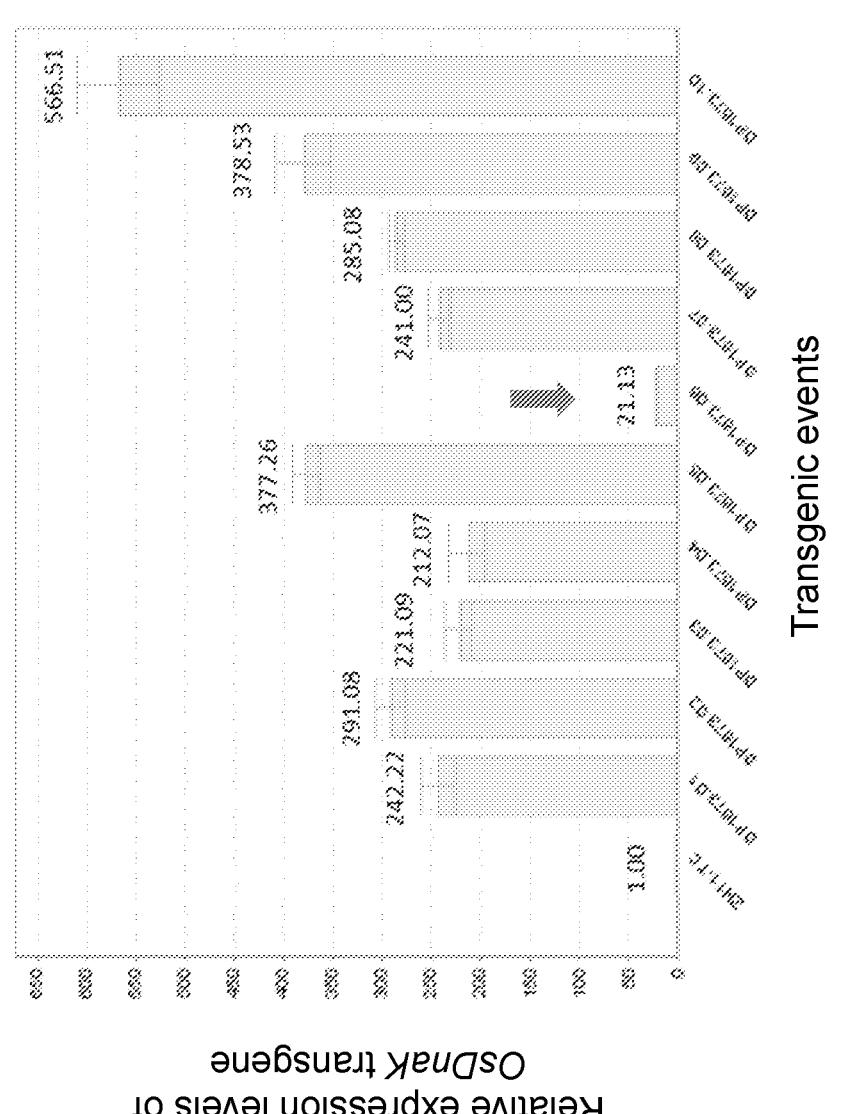
Fig.2 Relative expression levels of *OsDnaK* transgene

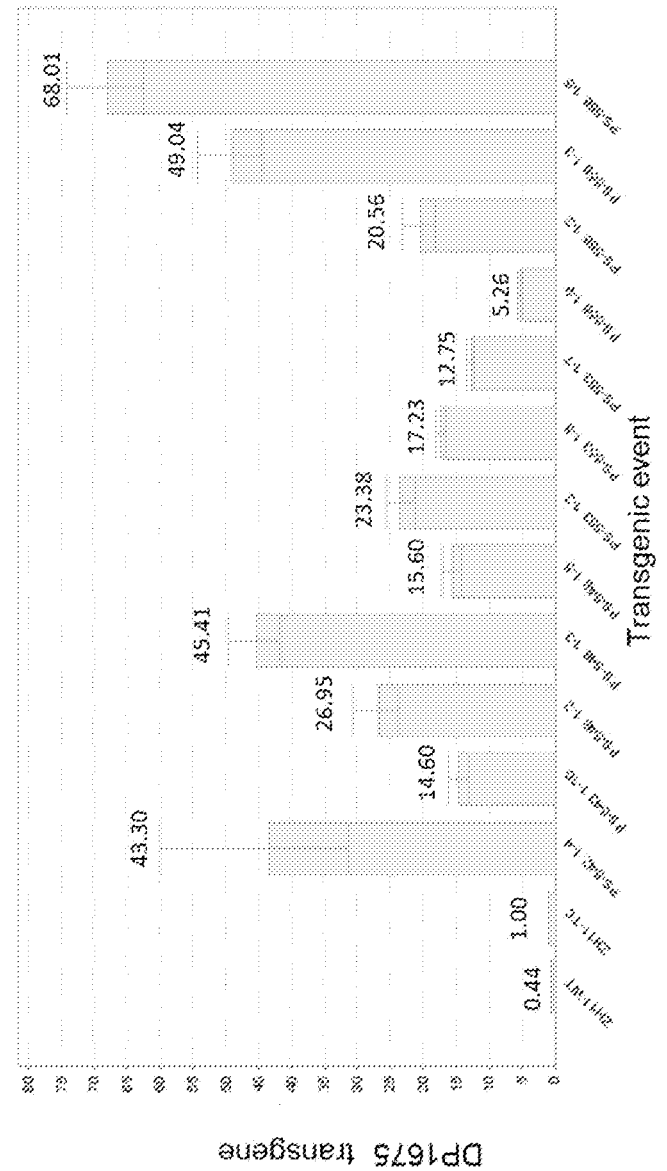
Fig.3 Relative expression levels of *OsPPT1-1* transgene

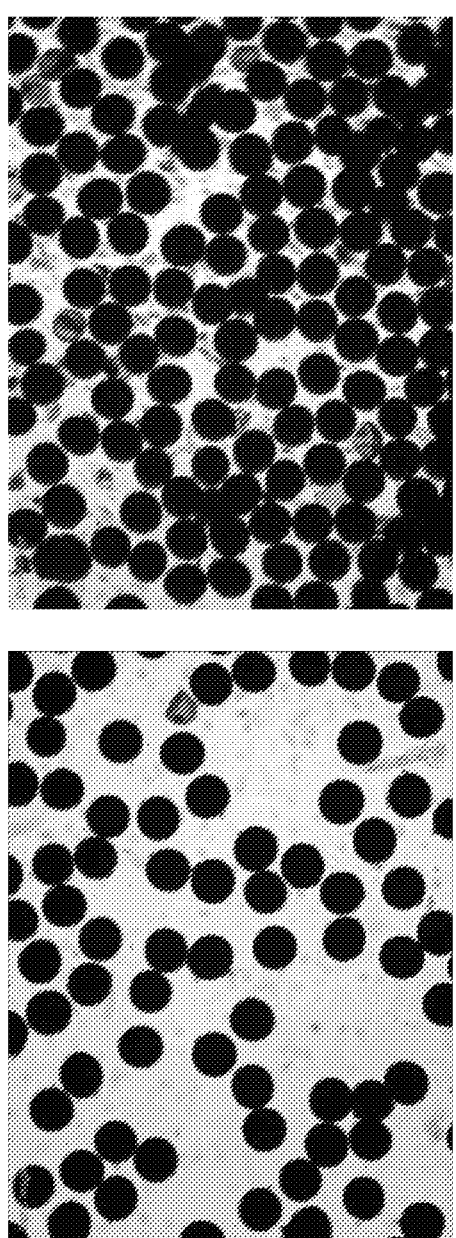
Fig. 4 Pollen staining result from DP0640 plants

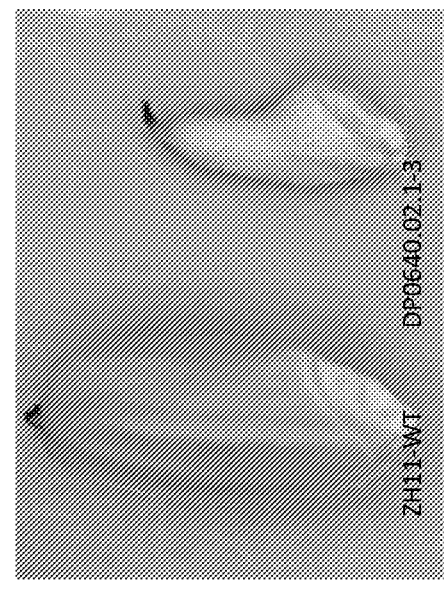
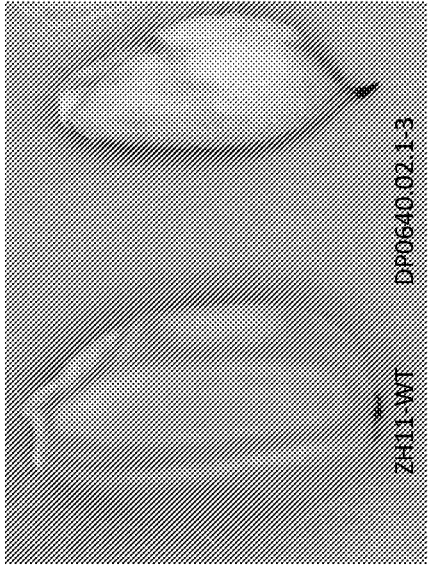
Fig.5 Seed morphology of DP0640 transgenic rice seeds

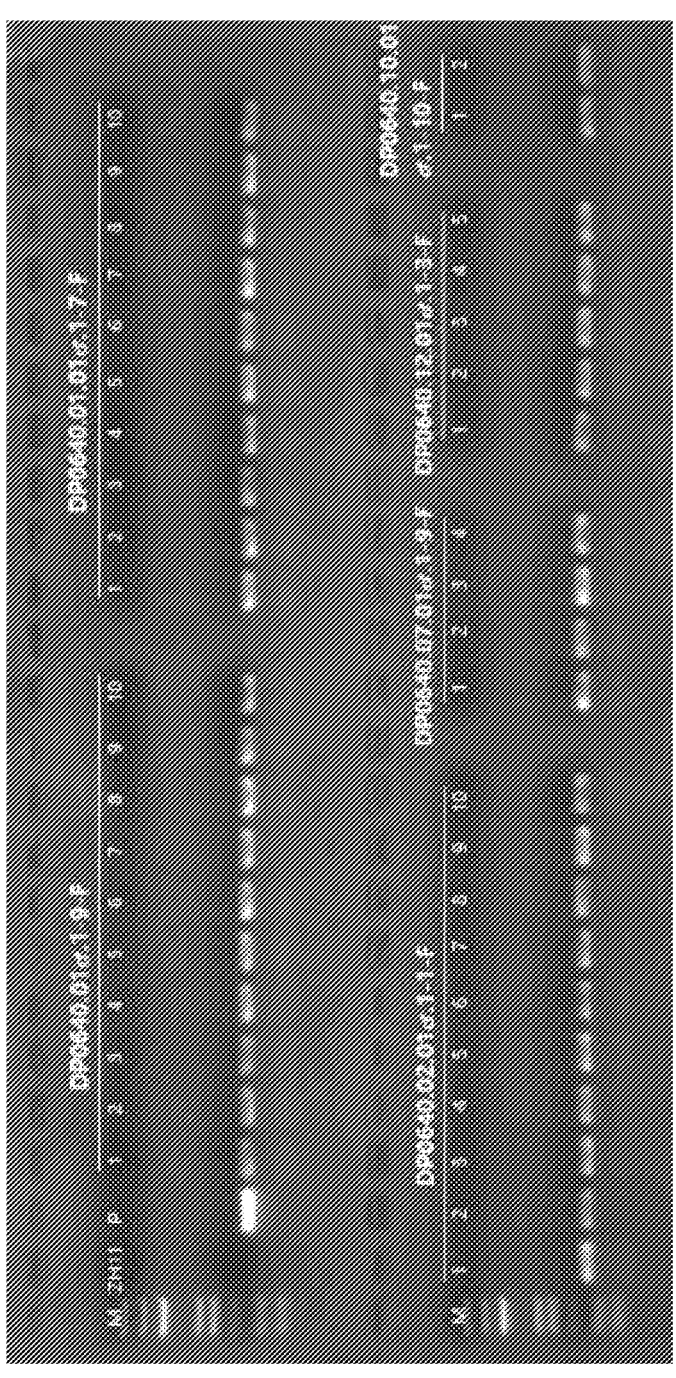
Fig.6 PCR amplification result of F1 hybrid plants of
DP0640 transgenic cross-out rice plants

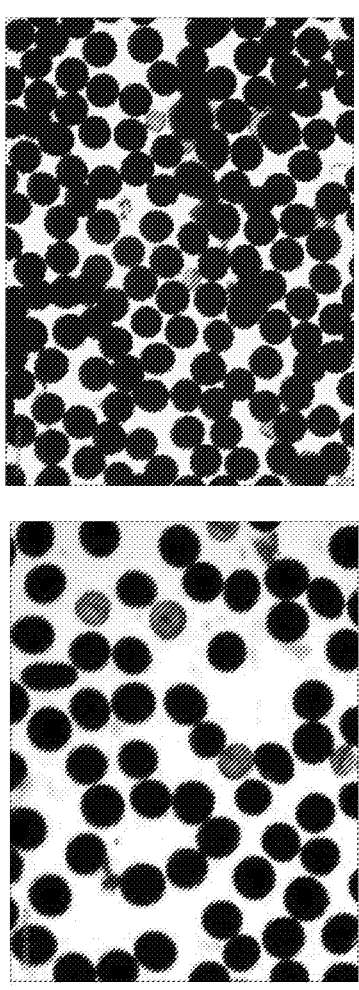
Fig.7 Pollen staining result from DP1673 plants

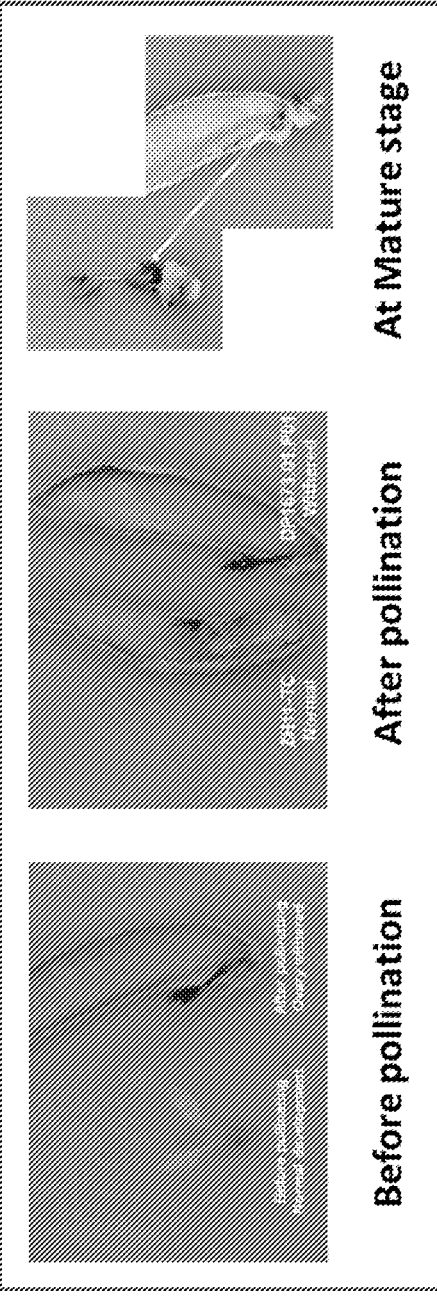
Fig.8 Pistil development of DP1673.01 plants
Before pollination    After pollination    At Mature stage

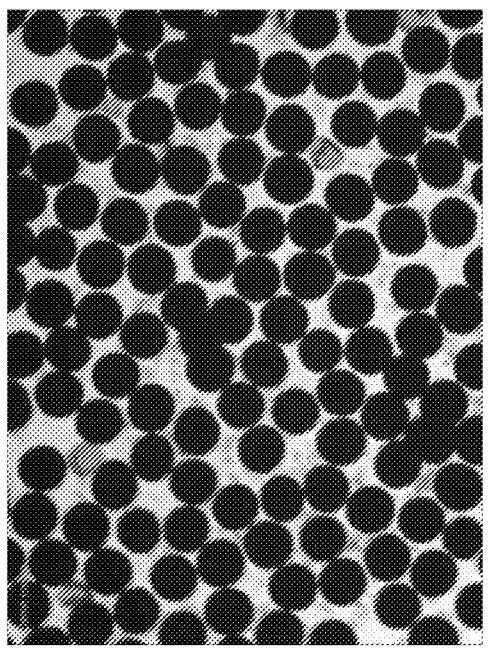
Fig. 9 Pollen staining result from DP1675 plants

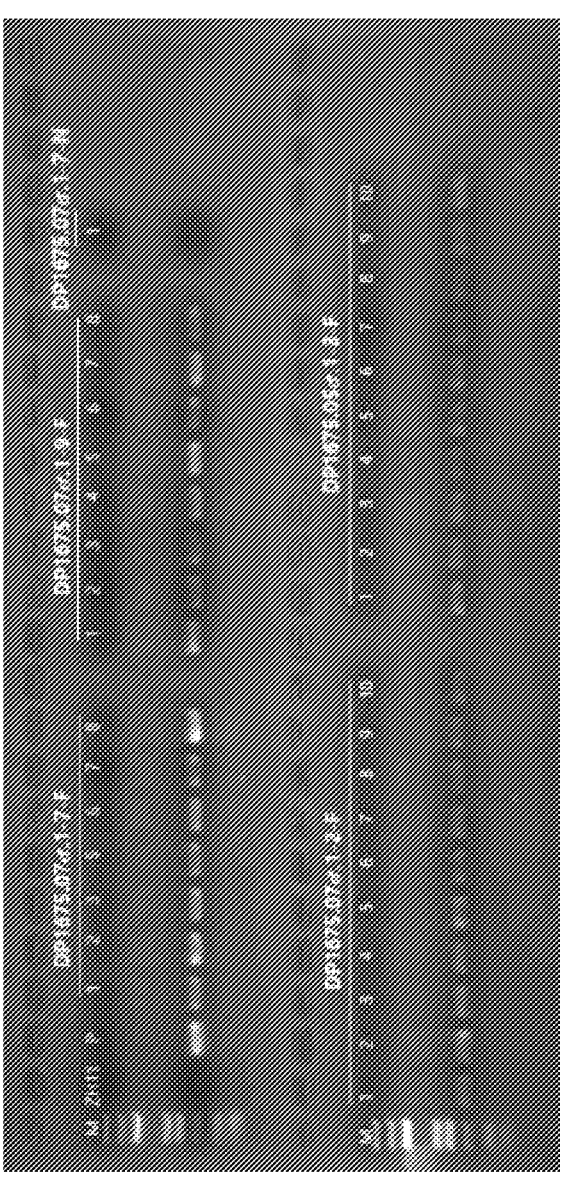
Fig.10 PCR amplification result of F1 hybrid plants of DP1675 transgenic cross-out rice plants

SEQUENCE LISTING

<160> NUMBER OF SEQ ID NOS: 52

<210> SEQ ID NO 1
<211> LENGTH: 1644
<212> TYPE: DNA

<213> ORGANISM: Oryza sativa

<400> SEQUENCE: 1
gaaaaaattc ccccaaaacc ctagcggcgg cggcgcgcgc tcccctcccc acctccgccg          60
ccgcggcgtc gaggcagcac cggagggcga tggcgtcgac ggtgctggag gcgacgcggg         120
cgaagcacga ggacatggag aggctggagc ggctggcggt gcgggagctg cagcgggagc         180
ccgccaacgc gcgcgaccgc ctctaccagt cccaccgcgt gcgccacatg ctcgacctcg         240
tcatctccac ctccggcaag ctcgtggaaa tctacgagga caaggataat gctaggaagg         300
atgagatctc caaccatctt agttccacag tgcaagctga aatctttcca aagttctatg         360
acaggctcaa agagatccgt gattaccata ggcgtaatcc ttctgcccgt ttcgttagtg         420
caactgatga tttcgaagag ctactaaagg aggaaccggc tattgaattc actggagagg         480
aagcttttgg ccgatacctg gacttgcatg agctttacaa tgagttcata aattccaagt         540
ttggaactcc aatggaatac tcagcatatg ttggcacctt ttctcatgtg gagaagatgg         600
cacaaaatct gaaaacctcc aggcaataca gagaataccg ggagcatatt ttggagtatc         660
tgacatcatt tctgtatcac acagaaccat gcaagacat tgagaagatt tttgcaaagt         720
tggaaagcga gtttgaagaa cagtggatca atggtgaagt gcctggatgg gagagcaagg         780
acccagagaa agaatctgca caagagtcag taatagacct tgattactat accactgttg         840
aagagcttgt tgagctgggc ccagaaaagt tgaaagaggc tttagctgct cgtggattaa         900
aaagtggtgg tactgttcaa cagcgtgctg agcgactttt cttgttgaag catacaccct         960
tggaacaatt ggatcgtaag cattttgcca aaggttcaca cagttctgtc tccaatgcta        1020
cttctaatgg taacaatttc aaggataatt tgaagaagga aattgcttta atggaagtaa        1080
agatgaggcg cctttgtgag ctactagatg agatcattgt acggacaaag gaaaatgcag        1140
agaagaagct gactctcaca tatgaagaaa tggaagcaga acgagaagag gaagaagtgc        1200
aagctgatag tgaaagtgat gatgaagacc aacaaatcta caatcctctt aagttgccga        1260
tgggttggga cggcaaacct atccctatt ggctatataa gctccatggt cttggtcagg        1320
aattcaaatg tgagatatgt ggaaaccaca gctactgggg gcgacgggct tatgagcggc        1380
atttcaagga gtggcgccat cagcacggga tgcgctgtct tggaattcct aatactaaga        1440
acttcaatga aatcacatcc atccaggagg caaaagaact ctgggagaaa attcaacaac        1500
gacaagggct gaacaagtgg cggccagacc tagaagaaga gtacgaagat caggagggaa        1560
atatctacaa caagaagacc tacactgatc tgcagcgcca gggcctgatt tagaatccct        1620
gatgcgatcc taacattttg gccc                                              1644

<210> SEQ ID NO 2
<211> LENGTH: 1524
<212> TYPE: DNA
<213> ORGANISM: Oryza sativa

<400> SEQUENCE: 2
atggcgtcga cggtgctgga ggcgacgcgg gcgaagcacg aggacatgga gaggctggag          60
cggctggcgg tgcgggagct gcagcgggag cccgccaacg cgcgcgaccg cctctaccag         120
tcccaccgcg tgcgccacat gctcgacctc gtcatctcca cctccggcaa gctcgtggaa         180
atctacgagg acaaggataa tgctaggaag gatgagatct ccaaccatct tagttccaca         240
gtgcaagctg aaatctttcc aaagttctat gacaggctca agagatccg tgattaccat         300 aggcgtaatc cttctgcccg tttcgttagt gcaactgatg atttcgaaga gctactaaag         360

-continued

```
gaggaaccgg ctattgaatt cactggagag gaagcttttg gccgatacct ggacttgcat      420
gagctttaca atgagttcat aaattccaag tttggaactc caatggaata ctcagcatat      480
gttggcacct tttctcatgt ggagaagatg gcacaaaatc tgaaaacctc caggcaatac      540
agagaatacc tggagcatat tttggagtat ctgacatcat ttctgtatca cacagaacca      600
ttgcaagaca ttgagaagat ttttgcaaag ttggaaagcg agtttgaaga acagtggatc      660
aatggtgaag tgcctggatg ggagagcaag gacccagaga aagaatctgc acaagagtca      720
gtaatagacc ttgattacta taccactgtt gaagagcttg ttgagctggg cccagaaaag      780
ttgaaagagg ctttagctgc tcgtggatta aaaagtggtg gtactgttca acagcgtgct      840
gagcgacttt tcttgttgaa gcatacaccc ttgaacaat tggatcgtaa gcattttgcc       900
aaaggttcac acagttctgt ctccaatgct acttctaatg gtaacaattt caaggataat      960
ttgaagaagg aaattgcttt aatggaagta aagatgaggc gcctttgtga gctactagat     1020
gagatcattg tacggacaaa ggaaaatgca gagaagaagc tgactctcac atatgaagaa     1080
atggaagcag aacgagaaga ggaagaagtg caagctgata gtgaaagtga tgatgaagac     1140
caacaaatct acaatcctct taagttgccg atgggttggg acggcaaacc tatccctat     1200 tggctatata agctccatgg tcttggtcag gaattcaaat gtgagatatg tggaaaccac     1260
agctactggg ggcgacgggc ttatgagcgg catttcaagg agtggcgcca tcagcacggg     1320
atgcgctgtc ttggaattcc taatactaag aacttcaatg aaatcacatc catccaggag     1380
gcaaaagaac tctgggagaa aattcaacaa cgacaagggc tgaacaagtg gcggccagac     1440
ctagaagaag agtacgaaga tcaggaggga aatatctaca caagaagac ctacactgat      1500 ctgcagcgcc agggcctgat ttag                                            1524
```

<210> SEQ ID NO 3
<211> LENGTH: 507
<212> TYPE: PRT
<213> ORGANISM: Oryza sativa

<400> SEQUENCE: 3

```
Met Ala Ser Thr Val Leu Glu Ala Thr Arg Ala Lys His Glu Asp Met
1               5                   10                  15

Glu Arg Leu Glu Arg Leu Ala Val Arg Glu Leu Gln Arg Glu Pro Ala
            20                  25                  30

Asn Ala Arg Asp Arg Leu Tyr Gln Ser His Arg Val Arg His Met Leu
        35                  40                  45

Asp Leu Val Ile Ser Thr Ser Gly Lys Leu Val Glu Ile Tyr Glu Asp
    50                  55                  60

Lys Asp Asn Ala Arg Lys Asp Glu Ile Ser Asn His Leu Ser Ser Thr
65                  70                  75                  80

Val Gln Ala Glu Ile Phe Pro Lys Phe Tyr Asp Arg Leu Lys Glu Ile
                85                  90                  95

Arg Asp Tyr His Arg Arg Asn Pro Ser Ala Arg Phe Val Ser Ala Thr
            100                 105                 110

Asp Asp Phe Glu Glu Leu Leu Lys Glu Glu Pro Ala Ile Glu Phe Thr
        115                 120                 125

Gly Glu Glu Ala Phe Gly Arg Tyr Leu Asp Leu His Glu Leu Tyr Asn
    130                 135                 140

Glu Phe Ile Asn Ser Lys Phe Gly Thr Pro Met Glu Tyr Ser Ala Tyr
145                 150                 155                 160
```

```
Val Gly Thr Phe Ser His Val Glu Lys Met Ala Gln Asn Leu Lys Thr
                165                 170                 175

Ser Arg Gln Tyr Arg Glu Tyr Leu Glu His Ile Leu Glu Tyr Leu Thr
                180                 185                 190

Ser Phe Leu Tyr His Thr Glu Pro Leu Gln Asp Ile Glu Lys Ile Phe
                195                 200                 205

Ala Lys Leu Glu Ser Glu Phe Glu Glu Gln Trp Ile Asn Gly Glu Val
            210                 215                 220

Pro Gly Trp Glu Ser Lys Asp Pro Glu Lys Glu Ser Ala Gln Glu Ser
225                 230                 235                 240

Val Ile Asp Leu Asp Tyr Tyr Thr Thr Val Glu Glu Leu Val Glu Leu
                245                 250                 255

Gly Pro Glu Lys Leu Lys Glu Ala Leu Ala Ala Arg Gly Leu Lys Ser
                260                 265                 270

Gly Gly Thr Val Gln Gln Arg Ala Glu Arg Leu Phe Leu Leu Lys His
                275                 280                 285

Thr Pro Leu Glu Gln Leu Asp Arg Lys His Phe Ala Lys Gly Ser His
                290                 295                 300

Ser Ser Val Ser Asn Ala Thr Ser Asn Gly Asn Asn Phe Lys Asp Asn
305                 310                 315                 320

Leu Lys Lys Glu Ile Ala Leu Met Glu Val Lys Met Arg Arg Leu Cys
                325                 330                 335

Glu Leu Leu Asp Glu Ile Ile Val Arg Thr Lys Glu Asn Ala Glu Lys
                340                 345                 350

Lys Leu Thr Leu Thr Tyr Glu Glu Met Glu Ala Glu Arg Glu Glu Glu
                355                 360                 365

Glu Val Gln Ala Asp Ser Glu Ser Asp Asp Glu Asp Gln Gln Ile Tyr
                370                 375                 380

Asn Pro Leu Lys Leu Pro Met Gly Trp Asp Gly Lys Pro Ile Pro Tyr
385                 390                 395                 400

Trp Leu Tyr Lys Leu His Gly Leu Gly Gln Glu Phe Lys Cys Glu Ile
                405                 410                 415

Cys Gly Asn His Ser Tyr Trp Gly Arg Arg Ala Tyr Glu Arg His Phe
                420                 425                 430

Lys Glu Trp Arg His Gln His Gly Met Arg Cys Leu Gly Ile Pro Asn
                435                 440                 445

Thr Lys Asn Phe Asn Glu Ile Thr Ser Ile Gln Glu Ala Lys Glu Leu
                450                 455                 460

Trp Glu Lys Ile Gln Gln Arg Gln Gly Leu Asn Lys Trp Arg Pro Asp
465                 470                 475                 480

Leu Glu Glu Glu Tyr Glu Asp Gln Glu Gly Asn Ile Tyr Asn Lys Lys
                485                 490                 495

Thr Tyr Thr Asp Leu Gln Arg Gln Gly Leu Ile
                500                 505
```

```
<210> SEQ ID NO 4
<211> LENGTH: 2071
<212> TYPE: DNA
<213> ORGANISM: Oryza sativa

<400> SEQUENCE: 4
ttgaacggaa gagaagaaag atggcgggca acaagggaga gggccctgcg atcggcatcg      60
acctcggcac gacctactcg tgcgtcggcg tgtggcagca tgacagggtg gagatcatcg     120
ccaacgacca gggcaaccgc accacgccgt cgtacgtggc cttcaccgac accgagaggc     180
```

```
tcatcggcga cgccgccaag aaccaggtcg ccatgaaccc caccaacacc gtctttgatg      240
caaagcggct gatcgggcgg cgcttctcgg acccgtcggt gcaggcggac atgaagatgt      300
ggccgttcaa ggtggtgcct ggcccagccg acaagccgat gatcgtggtg acgtacaagg      360
gcgaggagaa gaagttctcg gcggaggaga tctcgtccat ggtgctcacc aagatgaagg      420
agatcgccga ggccttcctc agcaccacca tcaagaacgc cgtcatcacc gtcccggcct      480
acttcaacga ctcccaacgc caggccacca aggacgccgg cgtcatctcc ggactcaacg      540
tcatgcgcat catcaacgag cccaccgccg ccgccatcgc ctacggcctc gacaagaagg      600
ccgccagcac cggcgagaag aatgtcctca tcttcgacct cggcggcggc accttcgacg      660
tctccatcct caccatcgag gagggcatct tcgaggtcaa ggccaccgcc ggcgacaccc      720
acctgggagg cgaggacttc gacaaccgga tggtgaacca cttcgtgcag gagttcaaga      780
ggaagcacaa gaaggacatc accggcaacc cgagggcgct ccggcggctg aggacggcgt      840
gcgagagggc gaagaggacg ctgtcctcca ccgcccagac caccatcgag atcgactcgc      900
tctacgaggg catcgacttc tacgccacca tcacccgcgc ccgcttcgag gagctcaaca      960
tggacctctt ccgccggtgc atggagcccg tggagaagtg cctccgcgac gccaagatgg     1020
acaaggccca gatccacgat gtcgtcctcg tcggaggctc cacccgtatc cccaaggtgc     1080
agcagctcct gcaggacttc ttcaacggga aggagctctg caagagcatc aaccccgacg     1140
aggccgtggc gtacggcgcc gccgtccagg ccgccatcct cagcggcgag ggcaaccaga     1200
gggtgcagga cctgctcctc ctcgacgtca cgccgctctc gctcgggttg gagacggccg     1260
ggggtgtcat gaccgtgctg atcccgagga acaccaccat cccaaccaag aaggagcagg     1320
tcttctccac ctactccgac aaccagcccg gcgtgctcat ccaggtgtac gagggcgaga     1380
ggacgaggac caaggacaac aacctgctcg gcaagttcga gctcaccggc atcccgccgg     1440
cgccgagggg cgtgccccag atcaacgtga cgttcgacat cgacgcgaac ggcatcctga     1500
acgtgtcggc ggaggacaag acgacgggga agaagaacaa gatcaccatc accaacgaca     1560
aggggcggct gagcaaggag gagatcgagc ggatggtgca ggaggccgag aagtacaagg     1620
ccgaggacga gcaggtgcgg cacaaggtgg aggcccgcaa cgcgctggag aactacgcgt     1680
acaacatgcg caacacggtg cgcgacgaga agatcgcctc caagctcccc gccgacgaca     1740
agaagaagat cgaggacgcc atcgaggatg ccatcaagtg gctcgacggc aaccagctcg     1800
ccgaggccga cgagttcgag gacaagatga aggagctcga gagcctctgc aatccgatca     1860
tctcaaagat gtaccagggc ggcgccggtg tccggcggg catggacgaa gacgcccca      1920 acggcagtgc cggcaccggc ggtggcagcg cgctggccc caagatcgag gaagtggact      1980
aagcgagtgg actgagtata tgacatgttg agcgggacga agaaggagcg atgcattctg     2040
ggacgtcatc atcatcttta gagtttcatg c                                    2071
```

<210> SEQ ID NO 5
<211> LENGTH: 1962
<212> TYPE: DNA
<213> ORGANISM: Oryza sativa

<400> SEQUENCE: 5

```
atggcgggca acaagggaga gggccctgcg atcggcatcg acctcggcac gacctactcg       60
tgcgtcggcg tgtggcagca tgacaggggtg gagatcatcg ccaacgacca gggcaaccgc      120
accacgccgt cgtacgtggc cttcaccgac accgagaggc tcatcggcga cgccgccaag      180
```

-continued

```
aaccaggtcg ccatgaaccc caccaacacc gtctttgatg caaagcggct gatcgggcgg      240
cgcttctcgg acccgtcggt gcaggcggac atgaagatgt ggccgttcaa ggtggtgcct      300
ggcccagccg acaagccgat gatcgtggtg acgtacaagg gcgaggagaa gaagttctcg      360
gcggaggaga tctcgtccat ggtgctcacc aagatgaagg agatcgccga ggccttcctc      420
agcaccacca tcaagaacgc cgtcatcacc gtcccggcct acttcaacga ctcccaacgc      480
caggccacca aggacgccgg cgtcatctcc ggactcaacg tcatgcgcat catcaacgag      540
cccaccgccg ccgccatcgc ctacggcctc gacaagaagg ccgccagcac cggcgagaag      600
aatgtcctca tcttcgacct cggcggcggc accttcgacg tctccatcct caccatcgag      660
gagggcatct tcgaggtcaa ggccaccgcc ggcgacaccc acctgggagg cgaggacttc      720
gacaaccgga tggtgaacca cttcgtgcag gagttcaaga ggaagcacaa gaaggacatc      780
accggcaacc cgagggcgct ccggcggctg aggacggcgt gcgagagggc gaagaggacg      840
ctgtcctcca ccgcccagac caccatcgag atcgactcgc tctacgaggg catcgacttc      900
tacgccacca tcacccgcgc ccgcttcgag gagctcaaca tggacctctt ccgccggtgc      960
atggagcccg tggagaagtg cctccgcgac gccaagatgg acaaggccca gatccacgat     1020
gtcgtcctcg tcggaggctc cacccgtatc cccaaggtgc agcagctcct gcaggacttc     1080
ttcaacggga aggagctctg caagagcatc aaccccgacg aggccgtggc gtacggcgcc     1140
gccgtccagg ccgccatcct cagcggcgag ggcaaccaga gggtgcagga cctgctcctc     1200
ctcgacgtca cgccgctctc gctcgggttg gagacggccg ggggtgtcat gaccgtgctg     1260
atcccgagga caccaccat cccaaccaag aaggagcagg tcttctccac ctactccgac     1320
aaccagcccg gcgtgctcat ccaggtgtac gagggcgaga ggacgaggac caaggacaac     1380
aacctgctcg gcaagttcga gctcaccggc atcccgccgg cgccgagggg cgtgccccag     1440
atcaacgtga cgttcgacat cgacgcgaac ggcatcctga cgtgtcggc ggaggacaag     1500 acgacgggga agaagaacaa gatcaccatc accaacgaca aggggcggct gagcaaggag     1560
gagatcgagc ggatggtgca ggaggccgag aagtacaagg ccgaggacga gcaggtgcgg     1620
cacaaggtgg aggcccgcaa cgcgctggag aactacgcgt acaacatgcg caacacggtg     1680
cgcgacgaga agatcgcctc caagctcccc gccgacgaca agaagaagat cgaggacgcc     1740
atcgaggatg ccatcaagtg gctcgacggc aaccagctcg ccgaggccga cgagttcgag     1800
gacaagatga aggagctcga gagcctctgc aatccgatca tctcaaagat gtaccagggc     1860
ggcgccggtg tccggcggg catggacgaa gacgccccca acggcagtgc cggcaccggc     1920
ggtggcagcg cgctggcccc caagatcgag gaagtggact aa                       1962
```

<210> SEQ ID NO 6
<211> LENGTH: 653
<212> TYPE: PRT
<213> ORGANISM: Oryza sativa

<400> SEQUENCE: 6

```
Met Ala Gly Asn Lys Gly Glu Gly Pro Ala Ile Gly Ile Asp Leu Gly
1               5                   10                  15

Thr Thr Tyr Ser Cys Val Gly Val Trp Gln His Asp Arg Val Glu Ile
            20                  25                  30

Ile Ala Asn Asp Gln Gly Asn Arg Thr Thr Pro Ser Tyr Val Ala Phe
        35                  40                  45

Thr Asp Thr Glu Arg Leu Ile Gly Asp Ala Ala Lys Asn Gln Val Ala
    50                  55                  60
```

-continued

```
Met Asn Pro Thr Asn Thr Val Phe Asp Ala Lys Arg Leu Ile Gly Arg
65              70                  75                  80

Arg Phe Ser Asp Pro Ser Val Gln Ala Asp Met Lys Met Trp Pro Phe
                85                  90                  95

Lys Val Val Pro Gly Pro Ala Asp Lys Pro Met Ile Val Val Thr Tyr
                100                 105                 110

Lys Gly Glu Glu Lys Lys Phe Ser Ala Glu Glu Ile Ser Ser Met Val
            115                 120                 125

Leu Thr Lys Met Lys Glu Ile Ala Glu Ala Phe Leu Ser Thr Thr Ile
    130                 135                 140

Lys Asn Ala Val Ile Thr Val Pro Ala Tyr Phe Asn Asp Ser Gln Arg
145                 150                 155                 160

Gln Ala Thr Lys Asp Ala Gly Val Ile Ser Gly Leu Asn Val Met Arg
                165                 170                 175

Ile Ile Asn Glu Pro Thr Ala Ala Ala Ile Ala Tyr Gly Leu Asp Lys
                180                 185                 190

Lys Ala Ala Ser Thr Gly Glu Lys Asn Val Leu Ile Phe Asp Leu Gly
            195                 200                 205

Gly Gly Thr Phe Asp Val Ser Ile Leu Thr Ile Glu Glu Gly Ile Phe
    210                 215                 220

Glu Val Lys Ala Thr Ala Gly Asp Thr His Leu Gly Gly Glu Asp Phe
225                 230                 235                 240

Asp Asn Arg Met Val Asn His Phe Val Gln Glu Phe Lys Arg Lys His
                245                 250                 255

Lys Lys Asp Ile Thr Gly Asn Pro Arg Ala Leu Arg Arg Leu Arg Thr
                260                 265                 270

Ala Cys Glu Arg Ala Lys Arg Thr Leu Ser Ser Thr Ala Gln Thr Thr
            275                 280                 285

Ile Glu Ile Asp Ser Leu Tyr Glu Gly Ile Asp Phe Tyr Ala Thr Ile
    290                 295                 300

Thr Arg Ala Arg Phe Glu Glu Leu Asn Met Asp Leu Phe Arg Arg Cys
305                 310                 315                 320

Met Glu Pro Val Glu Lys Cys Leu Arg Asp Ala Lys Met Asp Lys Ala
                325                 330                 335

Gln Ile His Asp Val Val Leu Val Gly Gly Ser Thr Arg Ile Pro Lys
                340                 345                 350

Val Gln Gln Leu Leu Gln Asp Phe Phe Asn Gly Lys Glu Leu Cys Lys
            355                 360                 365

Ser Ile Asn Pro Asp Glu Ala Val Ala Tyr Gly Ala Ala Val Gln Ala
    370                 375                 380

Ala Ile Leu Ser Gly Glu Gly Asn Gln Arg Val Gln Asp Leu Leu Leu
385                 390                 395                 400

Leu Asp Val Thr Pro Leu Ser Leu Gly Leu Glu Thr Ala Gly Gly Val
                405                 410                 415

Met Thr Val Leu Ile Pro Arg Asn Thr Thr Ile Pro Thr Lys Lys Glu
                420                 425                 430

Gln Val Phe Ser Thr Tyr Ser Asp Asn Gln Pro Gly Val Leu Ile Gln
            435                 440                 445

Val Tyr Glu Gly Glu Arg Thr Arg Thr Lys Asp Asn Asn Leu Leu Gly
    450                 455                 460

Lys Phe Glu Leu Thr Gly Ile Pro Pro Ala Pro Arg Gly Val Pro Gln
465                 470                 475                 480
```

```
Ile Asn Val Thr Phe Asp Ile Asp Ala Asn Gly Ile Leu Asn Val Ser
                485                 490                 495

Ala Glu Asp Lys Thr Thr Gly Lys Lys Asn Lys Ile Thr Ile Thr Asn
            500                 505                 510

Asp Lys Gly Arg Leu Ser Lys Glu Glu Ile Glu Arg Met Val Gln Glu
            515                 520                 525

Ala Glu Lys Tyr Lys Ala Glu Asp Glu Gln Val Arg His Lys Val Glu
        530                 535                 540

Ala Arg Asn Ala Leu Glu Asn Tyr Ala Tyr Asn Met Arg Asn Thr Val
545                 550                 555                 560

Arg Asp Glu Lys Ile Ala Ser Lys Leu Pro Ala Asp Asp Lys Lys Lys
                565                 570                 575

Ile Glu Asp Ala Ile Glu Asp Ala Ile Lys Trp Leu Asp Gly Asn Gln
            580                 585                 590

Leu Ala Glu Ala Asp Glu Phe Glu Asp Lys Met Lys Glu Leu Glu Ser
        595                 600                 605

Leu Cys Asn Pro Ile Ile Ser Lys Met Tyr Gln Gly Gly Ala Gly Gly
        610                 615                 620

Pro Ala Gly Met Asp Glu Asp Ala Pro Asn Gly Ser Ala Gly Thr Gly
625                 630                 635                 640

Gly Gly Ser Gly Ala Gly Pro Lys Ile Glu Glu Val Asp
                645                 650
```

<210> SEQ ID NO 7
<211> LENGTH: 3411
<212> TYPE: DNA
<213> ORGANISM: Oryza sativa

<400> SEQUENCE: 7

```
cctttctta gtgggcttca taacgcgagc cccatgccgg aatacgatcc ggcccatggg     60
ccaatgggag tccgtttcgt cttcgtcttc gtcgtcgtcg tcttctttc ttgcaagaaa    120 gaaaaggcgg agcaggagca gcaacgagaa aaggcggagg cggcggcgca accgacaagg    180
aaaagcaaag cgagagcagg aaaacctcgc cggcggcgac accaccacca ccagcaggca    240
gggatggccc ggtacgaccg cgcgatcacc gtcttctccc ccgacggcca cctcttccag    300
gtggagtacg ccctcgaggc cgtccgcaag ggcaacgccg ccgtcggcgt ccgcggcacc    360
gacaccgtcg tcctcggcgt cgagaagaaa tccaccccca agctccagga ctccaggtaa    420
atccttcaac ccgcccctc cccttcgccg gatctcaccc gcggatcgat ctccccccca    480
aatccaggtc catgcgcaag atcgccagcc tcgacaccca catcgcgctt gcctgcgcgg    540
ggctcaaggc ggacgcccgc gtgctcatca accgggcgcg cgtcgagtgc cagagccacc    600
gcctcaccgt cgaggacccc gtcaccgtcg agtacatcac gcgctacatc gccggactgc    660
agcagaagta cacccagagc ggcgggggtgc gccccttcgg cctctccacc ctcatcgtcg    720
gcttcgaccc ctacaccgag aagcccgccc tctaccagac cgacccatcc ggcaccttct    780
ccgcctggaa ggccaacgcc accggccgca actccaactc catgcgcgag ttcctcgaga    840
agaattacaa ggacacctcc ggcaaggaga ccatcaagct tgccatccga gccctccttg    900
aggtatatat atacacttca cactgaataa ttttactagt taaaactacc tctagctttg    960
atccactacc actgaatcag taactgtgct tctgaagaca gatactcaaa agtaattcac   1020
taatttgtgt tgcttatgtt gactggttca gtaatttgta agatgcccgc ctacgattga   1080
acatcgttat cttcgttaag ttccatatga ctcaatttgg tgcaaagatt aatagttccc   1140
```

-continued

```
tgaatctttg ttacaatcgg ctgagactat aaatgcagtc atgaacctaa aatagagtgg      1200
gatggatggg attggtttta ttgtgtttgc ttccatctta aagatgatac ttattggtgc      1260
ctggagtgat catagcaatt ggtatggctt ggatctgtaa tctcataaat catctccagc      1320
tatttcagca tttgtatatt ggttttcatc tgcacctcaa attttattgt tgtagtgttg      1380
gctataggtc tttaactctt tatccgtagt aaatcgtctc tagctattta atcatttgtg      1440
tattttgatt gtcatctgca tctcatattt taagtgttaa gcacggtttc aaaagttttt      1500
aaaggcattc ttatgtgagt acatttttct cttcaaaagt tattaaagtt gtttgattag      1560
tggcatataa acttttgttt ttctgttatt gataatctgc acctgtagtt ctcttctatt      1620
gcactgtaga agctgcaact tgcatgtatt ttgtcaactc tgctgccgct ttagtatgtt      1680
gctgcttaga tataggcacg gatgcctagt tcattgtatt tactgtctag gtaaaaaaaa      1740
tgtatataca ccattacaaa aatacatatc aaattaaggt catctttgtt taggcttaga      1800
cttattggct tgagattta agtcagctta ttggcttata tgttttataa accggtggat       1860
ttgaaatcct aagttcaatg gttgagtcat acctccactt catataatcc aacaaaatgg      1920
tttctccaac ctagcttttg gcttaacagt gtaagagtgg cttgtggctt taaaaagggc      1980
aaacaaataa gctgcttgtt tgtttaggct taggcttttt ggctcataag ctagcttata      2040
agcctaaaca aagaaggcct aagtctaaat gtccttttt cattactgta agtctctaac       2100
tgcaaatggt tatgttcctc aaggacacat agttcatagc taaatacttc aaattaagtt      2160
cttagcctgc atctggttat atattcgttt attggtggct tcaaatggtt aacacatatg      2220
cacagccacc attgagttta tgctagctaa tggtaagcag ttgatcattt ttgcaatctg      2280
ttgctcatac agaccgtgaa aatgcacgtc tcttgcacat tttgtcatat acgtatatgt      2340
ctgtacctct tttagtgaaa tatcttgctt tttttcgttg ttggaagaca aagtagtatg      2400
ttagtacttt gtttcatgct ttgccagttg ccacatatga caaactcatt gacctttttt      2460
ccattggtca gtggcagagg tagatgggta catgggggta catgtgtacc ccaaactctt      2520
tgctaaccaa ccacactata cataaacata tacaatttat actcaaataa gaaaactagc      2580
tattcaaggg aatgaagagt cacttatttt attagatttg aactttcatg aatctatata      2640
ccatatatga accaatttga taatttactg gtaaatgtca ctatattcta ataatcatgc      2700
cacttaggtc agattctgaa cccctcatta agaatattct ggctccacca atgccattgg      2760
ttatcacata tgcacagttc atgatatccg aaatcaattt cttactctgc ttatacattc      2820
attggtggct tcaaatggtt atcacatatg catattaact attgagtcca tggtacttat      2880
ttctttataa tgacattact actgccattt gataggtaat taagcatttt gtcagtctgt      2940
tgcacatgta gaatttctg atgagctctt ttagtgcaac aaatgtcatc cttttttact        3000
tgtctgtaga cagagatgcc tgcttgcttt gctttttttt tttcatgacg aactcattgg      3060
cctttgacct ttgtttattc agtgtttttt gctgagttgg tttctccatc atagctatat      3120
catttgatgc ttggcatttt atatgcaaca aatatcttaa atttgagtaa tgggttgatg      3180
tctccaggtt gtcgagagcg gtggcaagaa catcgagatt gcggtgatga cacacaagga      3240
tggcctccgc gagctggagg aggctgagat cgacgagtac gtggctgaga ttgaagcaga      3300
gaaggctgcc gccgaggccg cgaagaaggg cgccccgaaa gaaacctgac ctgatcatca      3360
tgattcagca aagcataatc tctcttagca tgtgttgttt cttttctgtt c               3411
```

<210> SEQ ID NO 8
<211> LENGTH: 960

```
<212> TYPE: DNA
<213> ORGANISM: Oryza sativa

<400> SEQUENCE: 8
atgccggaat acgatccggc ccatgggcca atgggagtcc gtttcgtctt cgtcttcgtc      60
gtcgtcgtct tctttcttg caagaaagaa aaggcggagc aggagcagca acgagaaaag      120
gcggaggcgg cggcgcaacc gacaaggaaa agcaaagcga gagcaggaaa acctcgccgg      180
cggcgacacc accaccacca gcaggcaggg atggcccggt acgaccgcgc gatcaccgtc      240
ttctcccccg acggccacct cttccaggtg gagtacgccc tcgaggccgt ccgcaagggc      300
aacgccgccg tcggcgtccg cggcaccgac accgtcgtcc tcggcgtcga gaagaaatcc      360
acccccaagc tccaggactc caggtccatg cgcaagatcg ccagcctcga cacccacatc      420
gcgcttgcct gcgcggggct caaggcggac gcccgcgtgc tcatcaaccg ggcgcgcgtc      480
gagtgccaga gccaccgcct caccgtcgag gaccccgtca ccgtcgagta catcacgcgc      540
tacatcgccg gactgcagca gaagtacacc cagagcggcg gggtgcgccc cttcggcctc      600 tccacctca tcgtcggctt cgaccctac accgagaagc ccgccctcta ccagaccgac       660
ccatccggca ccttctccgc ctggaaggcc aacgccaccg ccgcaactc caactccatg       720 cgcgagttcc tcgagaagaa ttacaaggac acctccggca aggagaccat caagcttgcc      780
atccgagccc tccttgaggt tgtcgagagc ggtggcaaga acatcgagat tgcggtgatg      840
acacacaagg atggcctccg cgagctggag gaggctgaga tcgacgagta cgtggctgag      900
attgaagcag agaaggctgc cgccgaggcc gcgaagaagg cgccccgaa agaaacctga       960

<210> SEQ ID NO 9
<211> LENGTH: 319
<212> TYPE: PRT
<213> ORGANISM: Oryza sativa

<400> SEQUENCE: 9

Met Pro Glu Tyr Asp Pro Ala His Gly Pro Met Gly Val Arg Phe Val
1               5                   10                  15

Phe Val Phe Val Val Val Val Phe Phe Ser Cys Lys Lys Glu Lys Ala
                20                  25                  30

Glu Gln Glu Gln Gln Arg Glu Lys Ala Glu Ala Ala Ala Gln Pro Thr
            35                  40                  45

Arg Lys Ser Lys Ala Arg Ala Gly Lys Pro Arg Arg Arg Arg His His
        50                  55                  60

His His Gln Gln Ala Gly Met Ala Arg Tyr Asp Arg Ala Ile Thr Val
65                  70                  75                  80

Phe Ser Pro Asp Gly His Leu Phe Gln Val Glu Tyr Ala Leu Glu Ala
                85                  90                  95

Val Arg Lys Gly Asn Ala Ala Val Gly Val Arg Gly Thr Asp Thr Val
            100                 105                 110

Val Leu Gly Val Glu Lys Lys Ser Thr Pro Lys Leu Gln Asp Ser Arg
        115                 120                 125

Ser Met Arg Lys Ile Ala Ser Leu Asp Thr His Ile Ala Leu Ala Cys
        130                 135                 140

Ala Gly Leu Lys Ala Asp Ala Arg Val Leu Ile Asn Arg Ala Arg Val
145                 150                 155                 160

Glu Cys Gln Ser His Arg Leu Thr Val Glu Asp Pro Val Thr Val Glu
                165                 170                 175

Tyr Ile Thr Arg Tyr Ile Ala Gly Leu Gln Gln Lys Tyr Thr Gln Ser
```

```
            180              185              190
Gly Gly Val Arg Pro Phe Gly Leu Ser Thr Leu Ile Val Gly Phe Asp
        195              200              205

Pro Tyr Thr Glu Lys Pro Ala Leu Tyr Gln Thr Asp Pro Ser Gly Thr
    210              215              220

Phe Ser Ala Trp Lys Ala Asn Ala Thr Gly Arg Asn Ser Asn Ser Met
225              230              235              240

Arg Glu Phe Leu Glu Lys Asn Tyr Lys Asp Thr Ser Gly Lys Glu Thr
            245              250              255

Ile Lys Leu Ala Ile Arg Ala Leu Leu Glu Val Val Glu Ser Gly Gly
        260              265              270

Lys Asn Ile Glu Ile Ala Val Met Thr His Lys Asp Gly Leu Arg Glu
    275              280              285

Leu Glu Glu Ala Glu Ile Asp Glu Tyr Val Ala Glu Ile Glu Ala Glu
    290              295              300

Lys Ala Ala Ala Glu Ala Ala Lys Lys Gly Ala Pro Lys Glu Thr
305              310              315
```

```
<210> SEQ ID NO 10
<211> LENGTH: 26
<212> TYPE: DNA
<213> ORGANISM: Artificial Sequence
<220> FEATURE:
<223> OTHER INFORMATION: Forward primer for cloning cDNA of OsZOS3-17
      gene

<400> SEQUENCE: 10
gaaaaaattc ccccaaaacc ctagcg                                        26

<210> SEQ ID NO 11
<211> LENGTH: 24
<212> TYPE: DNA
<213> ORGANISM: Artificial Sequence
<220> FEATURE:
<223> OTHER INFORMATION: Reverse primer for cloning cDNA of OsZOS3-17
      gene

<400> SEQUENCE: 11
gggccaaaat gttaggatcg catc                                          24

<210> SEQ ID NO 12
<211> LENGTH: 24
<212> TYPE: DNA
<213> ORGANISM: Artificial Sequence
<220> FEATURE:
<223> OTHER INFORMATION: Forward primer for cloning cDNA of OsDnaK gene

<400> SEQUENCE: 12
ttgaacggaa gagaagaaag atgg                                          24

<210> SEQ ID NO 13
<211> LENGTH: 27
<212> TYPE: DNA
<213> ORGANISM: Artificial Sequence
<220> FEATURE:
<223> OTHER INFORMATION: Reverse primer for cloning cDNA of OsDnaK gene

<400> SEQUENCE: 13
gcatgaaact ctaaagatga tgatgac                                       27

<210> SEQ ID NO 14
<211> LENGTH: 26
```

<212> TYPE: DNA
<213> ORGANISM: Artificial Sequence
<220> FEATURE:
<223> OTHER INFORMATION: Forward primer for cloning cDNA of OsPPT1-1
      gene

<400> SEQUENCE: 14
ccttttctta gtgggcttca taacgc                                            26

<210> SEQ ID NO 15
<211> LENGTH: 28
<212> TYPE: DNA
<213> ORGANISM: Artificial Sequence
<220> FEATURE:
<223> OTHER INFORMATION: Reverse primer for cloning cDNA of OsPPT1-1
      gene

<400> SEQUENCE: 15
gaacagaaaa gaaacaacac atgctaag                                          28

<210> SEQ ID NO 16
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsZOS3-17 gene

<400> SEQUENCE: 16
aggcaaaaga actctgggag                                                   20

<210> SEQ ID NO 17
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      OsZOS3-17 gene

<400> SEQUENCE: 17
ctgcagatca gtgtaggtct tc                                                22

<210> SEQ ID NO 18
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsDnaK gene

<400> SEQUENCE: 18
atcgaggatg ccatcaagtg                                                   20

<210> SEQ ID NO 19
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsDnaK gene

<400> SEQUENCE: 19
cgccctggta catctttgag                                                   20

<210> SEQ ID NO 20
<211> LENGTH: 21
<212> TYPE: DNA

-continued

```
<213> ORGANISM: Artificial Sequence
<220> FEATURE:
<223> OTHER INFORMATION: Forward primer for real-time RT-PCR analysis of
      OsPPT1-1 gene

<400> SEQUENCE: 20
gtggcaagaa catcgagatt g                                                 21

<210> SEQ ID NO 21
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsPPT1-1 gene

<400> SEQUENCE: 21
ttcaatctca gccacgtact c                                                 21

<210> SEQ ID NO 22
<211> LENGTH: 27
<212> TYPE: DNA
<213> ORGANISM: Artificial Sequence
<220> FEATURE:
<223> OTHER INFORMATION: Forward primer for PCR analysis of OsZOS3-17
      gene

<400> SEQUENCE: 22
atttggagag gacacgctga aatcacc                                           27

<210> SEQ ID NO 23
<211> LENGTH: 22
<212> TYPE: DNA
<213> ORGANISM: Artificial Sequence
<220> FEATURE:
<223> OTHER INFORMATION: Reverse primer for PCR analysis of OsZOS3-17
      gene

<400> SEQUENCE: 23
cggaggtgga gatgacgagg tc                                                22

<210> SEQ ID NO 24
<211> LENGTH: 27
<212> TYPE: DNA
<213> ORGANISM: Artificial Sequence
<220> FEATURE:
<223> OTHER INFORMATION: Forward primer for PCR analysis of OsPPT1-1
      gene

<400> SEQUENCE: 24
atttggagag gacacgctga aatcacc                                           27

<210> SEQ ID NO 25
<211> LENGTH: 20
<212> TYPE: DNA
<213> ORGANISM: Artificial Sequence
<220> FEATURE:
<223> OTHER INFORMATION: Reverse primer for PCR analysis of OsPPT1-1
      gene

<400> SEQUENCE: 25
ggtggatttc ttctcgacgc                                                   20

<210> SEQ ID NO 26
<211> LENGTH: 25763
<212> TYPE: DNA
<213> ORGANISM: Zea mays
```

```
<400> SEQUENCE: 26
cccagacggg cccaaatcta tcgcaaacag gcctcgtctc gtcctcgtcc tcgtccgccg     60
ccaaatcgaa ccccccccaaa ccctagctac ccggcgcaac gtccccttcc cgcctctccg    120
cggcgctgcg tgacacccgg cctccgctac gaaacaccgg ggcgggtgta gcctagcggg    180
cgggccatgg cgtcaacggt gctggaggcg acgcgggcgg cccatgagga tctggagagg    240
ctggagcggc tcgcggtgag cgagctgcaa cgggagcccg ctaacccgcg tgaccgcctc    300
tttcagtccc accgcgtccg ccacatgctc gacctcgtcg tctccacctc cggcaagctc    360
gtacgtgcca ttcttctgct tctaaggatt cacgactcca tccacttcac ttcagtgatt    420
cgttttgctt agctgggtca ggttcgaaca cggtcgatag gattgatatt tgcagttgtt    480
tctgtcgatt tcggatgctt gtttagggtt ggcttctgag tgtatgagga attacagatc    540
cgtcttcctg gcaaattctt attacatatc aatcatgtta tgtttatctc tgaattcgat    600
ctgtgtagat ggattttgtg ctcttatttt tactgtagtt ggcagtggca ctgcctgatt    660
agtgttgttc accggaggtt ttggctagtg ttatttctgt accgttctgt cccccttcatt   720 ctcttttggt ctgagtcagt agttgacctt tagaaatctt aattttgctg tccagcgacg    780
atctcacttt tgctctggtg cttgtaactt gtttaggtgg aaatttacga ggacaaggac    840
aatgctagga aggatgagat caacactcat cttactgcac ccacgcaaag tggactgttt    900
agcaagtact atgaaaggct caaagaggta ccttacctat ctgcttgctt ggatgtgaca    960
aaagtgaaat agatgccagt actcattact cattcaccaa aggtcatgat gatgcttatc   1020
atgttctttt tagtcgagtt cttctccgct tttaagaaaa cagtaatgta cggcacaaac   1080
tatatggctg gaggtaccag tttgcaaaca caaacaaaag caaacaagaa agaattgtcc   1140
tgttacaatg aaactaaagc tctgtaatgt tcgggacagg aataggtgaa ggcctgaagt   1200
tgtccatcca gttccaagtg atcttatcca ctctaatgtg gtcttttggt tttagtagtt   1260
gtagctccat ctactgcaga aacataaaac agcacaccag aggtgtggct aggaaatttc   1320
ctctcaaatc tcatcttatt gcatgatgca tgctttccac attgacaatg ccaagtcttc   1380
aaagaaaaaa aaagtatgta cgttgggta aatttaggtt agttatagcc taacttccca    1440
tgaagtcaga tctagaaatg ggatgaaagt cccaaccaaa agcctctgta aaactgcacc   1500
atgcagatct agcaataggg catctgaact tctgaagaac atatggccta tgttctcagg   1560
ttcattagag agaacatgcc atttctgggc cccttctttt tgaaactgtt gtggcctgta   1620
atttaccata gaaaaattga taattttcat gggcgctttt gatttccaaa gttcttttgt   1680
catactgtca ctgacacctc catcagttaa aagtctatag agatttggta gtgaactgca   1740
gccatcaaat ccaccatgg attgtagtca gatgaggata gaaacccact taaatttgta    1800
ccccaatcat cttcagttca atattcaatc actgtagcat ctggttcttc acaaatccta   1860
tgtaactcag ggtactcggt ttttttgaat gcaatggtag gagctctgcc tctcaattaa   1920
gaagaataga attgacccag tttttaggaa aaatcgggcc caaaacctaa cagagcacac   1980
aacagagtaa ccggcggaag gcccccacaa acaacctaga caacggtagc cccacactca   2040
caaaccccat ctagagtcat tgttgacaag ctcaacacaa gggatgagca ggtcccactt   2100
ctcaagacga gctgcacaca gccaaaggaa ctcgacgaca cctacaccca aataccgaca   2160
cacaaggaag aaggccgcga cacgccattg ttgccaagcc tcgacacgcc ccacgcgagg   2220
tagctccgat tcttcaccac gagcaatgtt ccacatcgcc gaacactggg agcagataga   2280
```

-continued

```
tgcctagagc gacaaaggcc caggtaccac cgagccaagc ggagtgacga aaagcctcca    2340
caacgccgac aaccacacaa aactggaggt cttccgggca acgtcttcaa ggagaaacga    2400
cgtcgagacg ccgccgtcgc ccgcctggaa caatccaagc aaagttttct ccgaagatct    2460
agcagagcaa cgttgattgc cagcaccaag gagaaaactg cagggacagc cacaccgatg    2520
tcaccccacc aagccgcccg gcgttgtctc cttctgccac ccaccgacgc accaaccctc    2580
agagcctcga cgccggccga gcaccagcga ggaaccccaa gaaggccgag gcgaggactc    2640
ccacacggag agcgagagat ctaggacgtc accctcaaca gggtaggagt ggcacccgta    2700
ggcgtcaccg acgtccgccc gtaaatgggc atcgctttcg ccggaggacc tcccaccaca    2760
tgtcccaacg gacggagcca gccagccctt cccacatcac cgaccgagaa gagaggtgga    2820
gagatggatc tggccggaga ggctcaaaat ttagcctcca accgatcgtg gagcatgatc    2880
tgaagccacg acgccgggaa ccgccgaggc tgccgtccca tgacccacca gctgcagccc    2940
tgccatattt acattgccgc tggcagctgc agtccgccgc taggccaagg cccacgcggg    3000
ccacgtcctc gacccaacca ccgtgccacg agcacggaca gggcgcaacc gccgctgtgg    3060
gctagccaca gctatgcgag ctggcatggc cgccgtcgcc aggcggccta ggccaccctc    3120
ctaggtcggc ggggagggag aggggtgggg agtggcggag cgaggggggag catctcgctg    3180 ctgccgccgt ccttgcaggg cgcgcgggaa gcgccgcgtc cctgctctgg cagtggcgag    3240
gccaagtcgt ggcggggggg ggggaggcta gggttctaag cacagcgccg cgagcccata    3300
tatcttccca taaaaaaatc ttcctgctat tgcatgcctt gcaaataact ccacatttga    3360
acaaatatgt aaaacctgtg taggcccctta tgtttgtaaa ctgctccacg tttgaacaga    3420
tgtttaaact tatgtacaga gaattgcctt tatgcttgga agtaaatgag ctattgctgc    3480
gtttggatgt cgatattgga gggcatggat ttgaatcggg ttgaatacca aatcagccat    3540
ggtattgaaa tgagatataa ttccaattct attgtttgga tgtcactaaa ttggagtttg    3600
gaatggtgcg gtctaattcc atgcaatacc gaggggtgag gccttgtatt gggatatgga    3660
gtttctagtt atagtccaat tccagggaat tgggtctctg atcccaaatc tcaattccac    3720
gtgcaaccaa acaacgaaat tttggaaagt tgattccaat tcgcaattct gtgctccaat    3780
atctacatcc aaacgaggta tacgagttct catttggcat gtatttggtt tgaagaattc    3840
ttaaccaagg attatttgag ccttgcacat atttccaaat ccattcataa tcttggtctc    3900
attgtcccaa gaccaccttg gtcctttggt ctgactatca ttcccaactt agccatatgt    3960
tatgttgttg aatttatctt atgcacttcg ctagaagatt tctgacctga tagagttcat    4020
cacttcatct tattgtgaac tctgctaatt gtaaaatcac actgtatcta tataggcata    4080
tgttaacctt cccaaggtta aacttttacc cttccatggg tctagcctcc tgagagcacc    4140
tagagggggg ggggtgaata ggtgatcctg aataattcaa acttatagcc acaaaaactt    4200
gttaagcgtt agcacagtta atgccaagtg gctagagcga agatcaatat gataatcaca    4260
aagagttcaa cacagagaag acacagtgat ttatcccgtg gttcggccaa gtacaaaact    4320
tgcctactcc acgttgtggc gtcccaacgg acgagagttg cactcaactc ctcaagtgat    4380
ccaatgatca acttgaatac cacagtgtta tgcttttctt ttcttatcgc gtttgtgagg    4440
aatctccaca acttggagtc tctcacccctt acacttgaag ttcacaaaga agcacggagt    4500
aagggagaga agcaacacac acaaatccac agcaaaatgc gcgcacacac ggccaagaat    4560
cgagctcaaa agactatctc aaagttctca ctagaacgga gctcgaatca ctgagaatga    4620
caaacgaatg cgcaaagact gagtgtggat gatcaagaat gctctaaggt tgcttggtct    4680
```

```
cttcctccat gcgcctaggg gtcccttta tagccccaag gcagctagga gccgttgaga    4740
gtaaaactgg aaggctgatc ttgccttctg tcgactggtg caccggacag tccggtgcac    4800
accggacact gtccggtgcc cgatttcttt ccttaaatgg cgcagtcgac cgttgcagat    4860
ctgggagccg ttggcgcacc ggacatgtcc ggtgcacacc ggacagtccg gtgccccctt    4920
ccgaccgttg gctcggccac gtgtcccgcg cagattgcgc ggccgaccgt tggctcaccg    4980
gacagtccgg tgcacaccgg acagtccggt gaattatagc cgtacgccgt cggcgaaatc    5040
ccgagagcgg ccacttcatg ccgagtcagc ctggcgcacc ggacactgtc cggtgcacca    5100
ccggacaatc cggtgtgcca gactgagctg agtcttggct gtacacagcc aagcttttgc    5160
acctctcttc ttttctgttt ctaacactta gacaaatata ttagtacaca aaaccaatgt    5220
actaaggctt agaaacatac ctttactctt gatttgcact ttgttcatcc atgggcataa    5280
attcacattt aagcacttgt gtttgcactc aatcaccaaa atacttagaa atggcacaag    5340
agctcatttc cctttcaatc tcccccttt tggtgattta tgccaacaca acataaagca    5400
actataacaa gtgcaatatc acttcaaata aaaactcagt tttattttga ttcaattttg    5460
gcatatatgg atcatccttt gccaccactt ggtttgtttt tgcaaatcaa actcaaatct    5520
ctatctctaa gtcaaacaca catgttgaaa cataaagaga gtcattccaa aagagattga    5580
tcaaggattt caaaaactcc cccttttttcc cataatcact acttctcccc acaagaagcc    5640
aacttttgac aaaagagaca atgaaagagt tttgacaaac caaaaactct actctactat    5700
tttcaaatct ctcaagtggt agctgatcca ttttttcactt tggcctttat tttctccccc    5760
tttggcatca agcaccaaaa cggaatcaat cttggccctt taaccccatt gcctcaccaa    5820
aatcttcaat taagagcaaa tggcaataag agttcatgag atgaacttgg aattagttac    5880
cctctcatcg gagtgcagtg gaagtctttc atggtccaag tccaccgttt ctctttcaat    5940
tctcctttga gactaaatca agcaaactca agcatatggt tagtctcaaa gggtcaagtt    6000
gtaacacatc tccccctaaa catgtgcatc actttgcaac ggacttgtga ggtccgggga    6060
gggtttgtac aacttgagca ccacaataag caacaaaatg cagaatgaac atgatcaaag    6120
gcataaacac atgtatgcta caattcaatc caagttccgc gaatctagga catttagctc    6180
actacgcagc ttgcaaaagg tcttctcatc tagaggcttg gtaaagatat cggctagctg    6240
gttctcggtg ctaacatgaa acacttcgat atctcccttt tgctggtggt ctctcaaaaa    6300
gttatgccgg atgtctatgt gctttgtgcg gctgtgctca acaggatttt ccgccatgcg    6360
gatagcactc tcattatcac ataggagtgg gactttgctc agattgtagc caaagtccct    6420
gagggtttgc ctcatccaaa gtagttgcgc gcaacactgt cctgcggcaa cgtactcggc    6480
ctcagcggtg gatagggcaa cagaagtttg tttcttagag ttccacgaca ccagggacct    6540
tccctaagaa ttggcacgtc cccgatgtac tcttcctatc gaccttacat ccagcatagt    6600
cggaatctga gtatccaacc aagtcaaagg tagaccccctt ttggatacca gagtccgaag    6660
caaggcgtag caaccaaata tctaagaatt cgcttcaccg ccactaagtg acactcctta    6720
ggatcggatt gaaatctagc acacatgcat acgctaagca taatatccgg tctactagca    6780
cataagtaaa gtaatgacct tatcattgac cggtatgcct tttgatcaac ggacttacct    6840
cctttgttga ggtcggtgtg tccgtcggtt cccatcggag tctttgcggg tttggcgtcc    6900
ttcatcccaa accgcttcag caaatcttgc gtgtatttcg tttgggagat gaaggtgccg    6960
tccttgagtt gcttcacttg gaacccaagg aagtagttca actcgcccat cattgacatc    7020
```

-continued

```
tcgaatttct gcgtcatcac cctgctaaac tcttcacaag actttttatta gtagaaccaa    7080 atattatgtc atcgacataa atttggcata caaacaaatc accatcacat gtcttagtga    7140
aaagagttgg atcggctttc ccaaccttga aagcattagc aattaagaaa tctctaaggc    7200
attcatacca tgctcttggg gcttgcttaa gtccatagag cgccttagag agcttacaca    7260
cgtggtcggc gtaccgttca tcctcgaagc caggggggttg ctctacgtac acctcctcct    7320
ttattggccc gttgaggaaa gcgctcttca catccatttg gaacaacctg aaagaatggt    7380
gagcggcata tgctagcaag atacgaatgg actctagcct agccacagga gcaaaagtct    7440
cctcaaagtc caaacctgcg acttgggcat aaccttttgc cacaagtcga gccttgttcc    7500
ttgtcaccac tccgtgctcg tcttgtttgt tgcggaacac ccacttggtt cccacaacat    7560
tttgcttagg acgaggcacc agcgtccaaa cttcattcct cttgaagttg ttgagctcct    7620
cttgcatggc caacacccag tccggatctt gcaaggcctc ctctatcctg aaaggctcaa    7680
tagaagagac aaaggagtaa tgctcacaaa aattaactaa tcgagatcga gtagttactc    7740
ccttgctaat gtcacccaaa atttggtcga cgggatgatc cctttgaatc atcgcttgaa    7800
catgggttgg aggtgccggt tgcgcatctt cctccatcac atgatcatct tgtgctcccc    7860
cttgatcaca cgcctcctgt tgatgaacct gttcatcgtc ttgagttggg ggtagcacca    7920
tagttgagga aggtggttga tctcgttcat cttgttcctg tggccgcact tctccaatcg    7980
ccatggttcg tatagcgccc gtcggaacat cttcttcatc tacatcatca caatcaacaa    8040
cttgctctct tggagagcca ttagtctcat caaatacaac gtcgctagag atttcaacca    8100
aacccgatga tttgttgaaa actctatacg cctttgtatt tgagtcataa cctaacaaaa    8160
agccttctac agctttggga gcaaattttg aatttctacc cttcttcaca agaatgttgc    8220
acttgctccc aaatacacga aagtacgata cattgggttt gttaccggtt agtagctcat    8280
atgacgtctt cttgaggagg cggtgaaggt agaccctgtt gatggcgtgg caagtcgtgt    8340
taacggcttc cgaccaaaaa cgctcggggg tcttgaattc tccaagcatc gtcctcgcca    8400
tatcgattag cgtcctgttc ttcctctcta ccacaccatt ttgctgtggt gtgtagggag    8460
cggagaactc gtgcttgatc ccttcctcct caaggaactc ctccacttga aggttcttga    8520
actcggatcc gttgtcgctc cttatcttct tcaccttgag ctcaaactca ttttgagctc    8580
tcctgaggaa gcgtttgagg gtcccttggg tttcagactt atcctgcaaa aagaacaccc    8640
aagtgaagcg ggaaaagtca tcaacaataa ctagaccata cttacttcct cctatgctta    8700
gataggcgac gggtccgaag aggtccatat gtagcagctc caggggtctt gatgtggtca    8760
tcacattctt gctgtgatgt gctcctccca cttgtttacc tgcttgacaa gctgcacaag    8820
gtctatcttt ttcgaattgc acgttagtta aacctatcac gtgttgtccc tttagaagct    8880
tgtgaaggtt cttcatcccc acatgtgcta agcggcgatg ccacagccag cccatgctag    8940
tcttagctat taagcatgca tctagaccgg cctcttcttt tgcaaaatca actaaataaa    9000
gtttgccgtc taatacaccc ttaaaagcta gtgaaccatc acttcttcta aagacagaca    9060
catctacatt tgtaaataga cagttatacc ccatgttgca taattgacta acagatagca    9120
aattatatcc aagagactct actaaaaaca cattagagat agagtgctca ttagaaattg    9180
caattttgcc taaccctttt accttgcctt gattcccatc accgaatata attgaatctt    9240
gagaatcctt attcttgacg taggaggtga acatcttctt ctccccgtc atatggtttg    9300 tgcatccgct atcaataatc cagcttgaac ccccggatgc ataaacctgc aagacaaatt    9360
taggcttggg acttaggtac ccaactcttg ttgggtccta taaggttagt cacaatttcc    9420
```

-continued

```
ttagggacccc aaatgcaagt tttatcagcc ttgcattttg cccctaactt cctagcaatt    9480
acctttctat cctttctaca aattgcaaag gaagcattca aagcatgata tattgtagaa    9540
ggctcattaa ctttcctagg aatattaaca acatttctcc taggcatatt atgaacaaca    9600
tcccttctac caacatttct atcatgcaca tatgaagaac tagaagcaaa catagcatga    9660
gaaaaatcat cgtacgcatt ataactccta taagcatttc tagtttgtct cctatcatga    9720
tacaaaaagg catgattctt tttagcacta gtagccatag gggccttccc tttctcctta    9780
gcgagaatgg gagccttatg gcttgttaag ttcttggctt ccctcttgaa gccaagtcca    9840
tccttaattg aggggtgtct accgatcgtg taggcatccc ttgcaaattt tagtttatca    9900
aattcattct tgctagtctt aagttgggca ttaagactag ccaattcctc agttaatttg    9960
gaaattgaaa ctaaatgatc actacaagca tcaacattga aatctttaca cctagtgcaa    10020
atctcaacat gttctacaca agaattagat ttactaccta cttctagttt agcatttaag    10080
tcatcattaa cactctttaa agtagcaatg gtttcatgac aagaagatag ttcactagaa    10140
agcacttcat ttctttttaac ttctaaagca taagattttt gtgcctctac aaatttgtca    10200
tgctcttcat acaaaaggtc ctcttgtttt tctaagagtc tatctttttc attcaaggca    10260
tcaatcaatt cattaatttt atctacttta gttctatcca atcccttgaa caaactagag    10320
taatctattt cattatcact agactcatca tcactggaag aatcataagt gacattgttt    10380
tgattacata ccttcttctc ccttgccata aggcatgtgt gacgctcgtt tgggaagagg    10440
gatgacttgt tgaaggcagt ggcggcgagt ccttcatttt cggagtcgga ggaggagcaa    10500
tccgaatccc actcctttcc gatatgtgcc tcgcccttgg ccttcttgta atgcttcttc    10560
ttttccctct tgctcccgtg ttcctggtca ctatcattgt cgggacagtt agcaataaga    10620
tgaccaagct taccgcattt gaagaatgat cgctttccct tggtcttagt cttgcttggc    10680
tgtcccttgc gaccctttag tgccgtcttg aatcttttga tgatgagggc catctcttta    10740
tcattaagac cgaccgcctc aatttgcgcc accttgctgg gtagcgcctc cttgctcctt    10800
gttgccttga gagcaatggg ttgaggctca tggattgggc cattcaacgc gtcgtccacg    10860
tacctcgcct ccttgatcat cattcgcccg cttacaaatt ttccaagaat ttcttcgggc    10920
gacatcttga tgtacctagg attttcacga atattgttta ccaagtgagg atcaagaacg    10980
gtaaatgacc ttagcattag gcggacgacg tcgtgatccg tccatcgcgt gcttccgtag    11040
ctccttattt tgttgataag gatcttgagc cggttgtatg tttgtgtcgg ctcctcgccc    11100
cttatcatcg cgaatcgtcc gagctcgccc tccaccaact ccatcttggt gagtaaggtg    11160
acatcattcc cctcatgaga gatcttgagg gtgtcccaaa tttgcttggc attgtccaag    11220
ccgctcacct tgtgatactc gtccctgcac aaagaggcta acaacacagt agtagccttgt    11280 gcatttttat ggatctgttc attaataaac gaagggctat ccgagctatc aaatttcatt    11340
ccactttcca caatctccca aatgcttgga tggagagaaa ataggtgagt acgcattttg    11400
tgactccaaa atccgtagtc ctctccatca aagtgaggag gcttgccaag tggaatgggg    11460
agcaaatgag catttgagct atgcggaatg cgcgaataat caaaagaaaa gtttgagtta    11520
accgtctttt gtttgtcata gtcgttgtcg tcgttgtcct tttgggaaga ggaagattcg    11580
tcgctgtcgt cgtagtagac gatctccttg atgcgccttg tcttcctctt cttcccttcc    11640
ttccgtctgt ggcccgagcc ggagtcggta ggcttgtcat ctttgggctc gttgacgaag    11700
gactccttct ccttatcgtt gatcacgatt cccttcccct taggatccct ttcttcgggc    11760
```

-continued

```
ggttagtccc tttcttgaag agaacggctc cgataccaat tgagagcacc tagagggggg   11820
tgaataggtg atcctgaata attcaaactt atagccacaa aaacttgtta agcgttagca   11880
cagttaatgc caagtggcta gagcgaagat caatatgata atcacaaaga gttcaacaca   11940
gagaagacac agtgatttat cccgtggttc ggccaagtac aaaacttgcc tactccacgt   12000
tgtggcgtcc caacggacga gagttgcact caacccctct caagtgatcc aatgatcaac   12060
ttgaatacca cagtgttatg cttttctttt cttatcgcgt ttgtgaggaa tctccacaac   12120
ttggagtctc tcacccttac acttgaagtt cacaaagaag cacggagtaa gggagagaag   12180
caacacacac aaatccacag caaaatgcgc acacacacga ccaagaatcg agctcaaaag   12240
actatctcaa agttctcact agaacggagc tcgaatcact gagaatgaca aacgaatgcg   12300
caaagactga gtgtggatga tcaagaatgc tctaaggttg cttggtctct tcctccatgc   12360
gcctatgggt ccctttttata gccccaaggc agctaggagc cgttgagagt aaaactggaa   12420
ggctgatctt gccttctgtc gactggtgca ccggacagtc cggtgcacac cggacactgt   12480
ctggtgcccg atttctttcc ttaaatggcg cagtcgaccg ttgcagatct gggagccgtt   12540
ggcgcaccgg acatgtccgg tgcacaccgg acagtccggt gcccccttcc gaccgttggc   12600
tcggccacgt gtcccgcgca gattgcgcgg ccgaccgttg gcccggccga ccgttggctc   12660
accggacagt ccggtgcaca ccggacagtc cggtgaatta tagccgtacg ccgtcggcga   12720
aatcccgaga gcggccactt catgccgagt cagcctggcg caccggacac tgtccggtgc   12780
accaccggac agtccggtgt gccagactga gctgagtctt ggctgtacac agccaagctt   12840
ttgcacctct cttcttttct gtttctaaca cttagacaaa tatattagta cacaaaacca   12900
atttactaag gcttagaaac ataccttttac tcttgatttg cactttgttc atccatgggc   12960
ataaattcac atttaagcac ttgtgtttgc actcaatcac caaaatactt agaaatggcc   13020
caagagctca tttcccttttc acctcctcag catcttattg tgaatttctg aaaatgcttt   13080 aaacccccata aacatgatac tgtttttcaa tggtggtgcc gttttttaac gaaatgactc   13140
atgtgaatat ccaaaaagta gacaagttgg aaaaatgatt tgaaagtaac aaagatttca   13200
tgcatttaat taagaacatt tttttgtggc gcgcgctggg ggggggggc agtctatttt   13260 tgctgtccca attaccaaag taagccttgg aaaatgaact gatcagcgac cagacattgg   13320
gttggtttcc ctattattgt aagatttgca gcatgttggt tctttacatg catccttttt   13380
tggtcccttt gccccccccc ccctgtgatt tatgggtaat ttgtcttcga agaagctgtg   13440
ctagtaaaca gatattcatt tatcagcaaa tctctagtgt ttcttttttt ttgtgaactt   13500
ttaagtatat tttattgctt gcttacagat ccgtgaatat catcggcgga acccatctgc   13560
ccgctttgtt agtacaactg atgactatga agagcttcta aaggaggaac cagttattga   13620
attcactggc gaggtattgt caccttttttt gattattgca acttcgtttg atattttgtg   13680
tgccttttta tcatgggtca tatgacgttt aatcttagta acttgttact tgcacgcatt   13740
tagtcttagt aacttgttac ttgcatgatt tttccagatg attgatactt atatgcctgt   13800
gactattcaa gcctttaaaa ctattgcagt ttatctggac acatctttttt gtaattgttt   13860 gtgccatgtt atagtctttg tgttttgacc tatgcaagtt acgttgctca tcaacagggt   13920
tttctaaaaa cctttgggct tgtttggtga caagggaatt gaagaggatt ggaggggatt   13980
gagagggaaa ttagttcatt tcccctcaa tcccctccaa tcccctcaa ttcccttgtt   14040 accaaaggag cccttagagt ccatcagtgc ctttcctttt cctttcacta cagtagtctt   14100
gaagctgagg gtatctcctt tgtgatacgt gtacttcaat ttctgcagga ttgtttgatt   14160
```

-continued

```
cctcttgtgg gatcttggtg gtgtcgatgg taagatttgg gcaatgattg aaactgcgat    14220
gtagaatgat gaataacttg acaatcattc aatgatctat tcctctttct gattttcacc    14280
gctgcacagt cctttttcctg ttataccatg ttgcatattt actacatttt tctgttacta    14340
ttatactatt ctcacaatag tcttaattag gttttctgat gatctggttc tgcattttga    14400
taggaaactt ttggccgtta ccttgacttg catgagcttt acaaacagtt ttaattatgt    14460
tttctgatga agtgatgatc tggttctgca ttttgatagg aaacttttgg ccgttacctt    14520
gacttgcatg agctttataa tgagttcata aattccaagt tcggaacact gatggaatat    14580
tcagcttatg ttggctgttt ctcccagacg gacaagatct cacatagtca taaagctacc    14640
aggtatgtca tgcatagttt ttcactaagg tctgaaatgt acgatctcct ggcatgggtt    14700
tgactagtat ggtttaccta ccgtaggatc ataaggctca acatgttcaa gtctatatgt    14760
ataatagttg ttcaactgtt tattgtttaa cctgtctagc attcatttca tatatggtta    14820
atagggaaaa accctaaatc atggtatagg gtattgcata tccaagtaca tgtggatgat    14880
agttgctcag ctgtttacct gtctaacatt tatttcatat gttggtgccc ttatatgtca    14940
attataatgt tgaatattct ttatatctta caatttcttt aattgacaga aaatacagag    15000
aatacttgga acatattttg gaatatctga catcatttct gtatcgcaca gagccattgc    15060
aagacattga taagattttt ttaaaggtca gtcttatttt accattttct atattaatgt    15120
ccatttgtgt tccacatgtt tatgtgatta tgtagaggat catactttgc tttgtatttt    15180
ttaactatga tgtcgcttct ttatattcat tttggagctg ctaatagtgc tttggcagtg    15240
atttgttcaa tagcatagag catatttatg attaaatact taataactta cattctaatg    15300
gcatacattg gtacagctgg agagtgaatt cgaggaacaa tgggccaatg aaggaatact    15360
tggatggggg aataaaggga cagaaaaaga gtctgaaata gatctcgatt actacagcac    15420
agttgaagaa cttgttgagc ttggcccaga aaaattaaaa caggtttgat tttaaaacat    15480
tatgctgtta ccaaaagtta ttttcttgtc tgttattgtc aactgtacat aggttccttt    15540
ctgatgagtt ctgttgattc atttacatcg ttttaggctt tagctgctcg aggttttgaag    15600 agtggcggta ctgttcaaca gcgtgcagat cgtctttttct tgttgaaggt gatattaaag    15660
acgctagtgc tactgctggt tcatctattg ttcttgcctt tttaccattc attttgaact    15720
ttttgttgat tatattttgc aggttacacc gttggaacaa ctagatagga agcattttgc    15780
caaagttcca catactaaag atggctcaaa cacagctcct aatggtaatg ctttcaagga    15840
ggatatgaag aaagaaattg cattgatgga agtgaagatg aaacgtcttt gtgagctgct    15900
agatgaggtc tgctcttcac tgctccctgt ggttacgact tacgacttta ctcatgtaat    15960
tttgaacgca tggtacactc atgcaaatgc actagcatgt gcagtcaatc cttttgtgac    16020
cacttagggt gcgtttggtt acgggacaga caggagaggg acgttctctg gcgtcctctc    16080
ctgtccctcc aattttgagg gataagtggg gataacattg ggatagtcat gtcccaaccc    16140
ttgaccttga accaaaacaa ccttatttga gggatcgtcc cattccgtcc cgtcctgtca    16200
ttgcaaccaa acacaccctt aattcctcat ataagctcat cctatgaaga tcaaacctgc    16260
ttactttgag gaatgtactt tgttgccatc ttaggctagt ctattcaaat ggaatattga    16320
tttctttggc tagacctctc gtttgtctgg cattacactg ttcctcaaat tgcaattttg    16380
ggcatgcagg gaagtactaa ggtatgattg tagacttgtt ctgaaatagt tcatgtgatg    16440
tgtgggtgtt ttttttcctt tgtgtattct ctatcacttt ttgtttgtgt tgaaaactcc    16500
```

-continued

```
atttatatta tcacaactta agacatgctt taacggcttt ataaaaaaaa ttaacagatg   16560
attagtgcat cgcctcttct tttttcctaa taatactgtg tatgtactgg ccaccaatat   16620
aatcacatgc cagttctaat atggtagata tgtatatttt tgtttgcaaa cccaagcaca   16680
aactgtaccg ggactgtgct acaattccat tccagaacaa tccacttctt gttactacta   16740
accttctttt tgggaagagc tactagtgtt cgttgcatct ttttatgtct atatgttgac   16800
attaacctga tatttttgac attttatgtt gcttgtgtag gcctttgtaa ggacaaagga   16860
aaatgcggag aagaagctta cttttgacata tgaagagatg gaagcagaac gggaagaggt   16920
aattagttac ttacccctct tctaaaaaaa cttatctgtg tcttgcacta ttcctggagt   16980
ccagaatgtg ttctttattt tcaatgttgt agctgctgct atccttgtgc tatcttgaaa   17040
acaccaatga gtgtgttttt taacaattct aaaatatgaa ctgacatatg catgtctgat   17100
actctgatat gctttagaaa gagaactact cagctaaaga tgctcttggc tgcttttta   17160 tcagtattgt tgctactgag atataccaaa atcatgatca tggacatgga ataccatttt   17220
cctttcccct aaaacagttc tgcaagtgtc ttggatgtaa cccaatcttt tttgtattct   17280
gaaaatcctt tctctgggtc atggcatgct cttttgcttt gaaaattttg tagtacatag   17340
tgaataagtt tccaagttgt ttactatgca tttccattgt gatttgctga ttagtgttgt   17400
cacatttagc cctaataact tattaagccg catatcgtga caaggttcag ctaggcgcta   17460
ggcggaatct aggcggtgac ccattgccta gcgcctagtc gggagtactc ggtcttaggc   17520
gcttctaggc gcttttctag gcgtttggc aatatagcca taaattatat atattatgta   17580
tataactata tatacgtata taactactat atatgactat atgagtcaca gactcacagt   17640
aagtataaaa agaaggccgg tagacatatc tgattcctag ctgagcttac tcttgctgtc   17700
ttgcatgttc ctagctcctg caaggctgca acacattttg acagctagta gttagtaaat   17760
tagtcaatag acagctagtt gttcataaaa aatagaaaac actaaattgt gacttatctg   17820
gatgatttca gcagcctccc attcatgagc agttgagcac actgcacacc atatcagcag   17880
ctggtaatta caacacaagt ggataagaca gtaatacaag tgcagaacac aatttataaa   17940
taaaggacaa cacaagcaca tagttcttag ttcaggtctc acacaaaaga agacacacag   18000
acacaaagtg acacagctgc agttcataag accagggcat cacaaaaggc ttcactacta   18060
catggagatg gtccagatca tatttcatct tcactgtagc acaaatcttc atcttcatac   18120
tcttcttctt cagactcaaa ctcttctcct tcatagagct ctctcactct tgcacttcta   18180
cgaggctcaa gctgttcttc tgctcccact gcctctccaa taacagacca aggtatccct   18240
gtaccttcca tctcatcttc ctcctcatct ctaaagacaa cttgtgcaca atcatctcca   18300
ccgtcttgga gaaaaccttg agcttcagtt gtatcactag acaagagaac atcagtgatt   18360
ttctttgact taatctttc tctgttattc atcagcctgt tattgaactg aatatagacc   18420
aacttgttga ggcgggttgt agtcagccta tttctcttct tagtgtgtat ctataaatta   18480
gaaacagaag cattttcagt tctgaaattt aatcatagta ctgctgaaat gattaataga   18540
taggtcatag gtactaaccc cttcaaaccc actccaattt ctttcacaac cagaagagct   18600
tgatgtcaaa gataatatcc ttgtagccat ctttttgtaaa gctggtgttt cagttccata   18660
taaccgccac catgatgctg acataaatta gaaacagcca acattagctt cacatccttc   18720
caaaaggctg gactcaatat agtagctgtg gcctctttc ctttctttga tttcacatcc   18780
tttaatgagt cccacctgct atgaactacc atcttcctta actggtcctt cttctcttgc   18840
atactgttca aagtgagaaa gtatgaagca aacctagtca ctcctggcct cactagctct   18900
```

```
ttcccctctg tgaagtatct caagcactcc aatgttcttg tgtggccata cacaaatatg   18960
gtaaatgact ttgcttggtc aatcactttc ctgaaccgag gcaatttgcc aattccttgg   19020
agcatcaagt tgattgtgtg agctgcacaa gaggtccaaa atatttgtgg tctcttctca   19080
agcaatagct tctttgctcc catgttgtta gaggcattgt cagtgactac ttgcaccaca   19140
ttttcttcac caatgtcttc aattgctttg tccactaatt caaaaatgac ttcgcttgtg   19200
tgtgacacat ctgacatctc ttttgagctg atgaaggagg ttccatcagc acaattagtg   19260
catatattca ttatgcttct cctcttccta tctgaccaag catcggtcat aatagagcaa   19320 ccatttttc atcttctcgg cttcacgttc ctgcagcaaa cacttggttc tttcatattt   19380
cttcttccag caaactacct cgaaaggcat cttgagttgg aggtgtaagt cctggtccaa   19440
attgtccaat tgcttcacac atttgcttga actcatcatt gtcacatgca ttgaaaggta   19500
ttcctgccaa tgattaaaaa atgaagtcta atttaaaat gtgttcagtt caaagttcat   19560
gaattttaaa atgtgaaaac agcatcgtat actagcaatt taccatgatt ataggcccat   19620
cttgcaataa acttgtgcac ctcatgctct ctttctttcc atagttcctt gttcagctgc   19680
tgttgtttga atgaatcagc cttggtagga tcaatagcac gtgtccattt gtcaattggc   19740
cctaatttgt gaggctgtga gcttccaaca caagtgactt cttctgactc ctctccaacc   19800
ctagatacat tcacttcctc tctaagttct agctcacgaa cagtcttctc ctccctcttc   19860
ctttttgcag cctctattgc tttcttgcac ttctctttag cctctagagc ctgcggtgtt   19920
gcagacgtgc atttcttcac attctttcca acatgggcaa gatgttcctt caacctataa   19980
atccctcccc tcatctcctt gtcacagaac ttacacttca ccttgtcttt gttgttagca   20040
tcaacaagaa caccatattc ccatccaaca tcatctgaat ttctttttag gagattcgct   20100
ctagctgctt cagtttcaga aggtgtagct gcagtttctg atgacatcct taaaccttaa   20160
tcctttgatt tctttcactt gtacactgca caggggagga aagcagtttc agcaggggag   20220
gaaagcaggg gaggaaagca ggaaagcagg ggaggaaagc aggggagggg gatgagcagg   20280
gaggggagca gccgacgggg gaggagaact caccggcggg ggagcaggga gccgacgggg   20340
gagcagcagg aggggatctc accggcgggg gagcagggcg ccggcggcgg agccggcggt   20400
ggagcaggga gccgggcggt ggagcaggga gccggcaggg agactgcgct aaaactgccc   20460
tgcgcgctaa aactcacgcg cgctaaaaac taacgcgcgc tgcgcgcgct aaaacgcgcg   20520
ctctcccgcc tgcgcgcccg catgcgcgcc cgcgcgcccg tcctgcgcgc ccgcctgcgc   20580
gcccgcttag gcgctgtgcg ccgcccactc gccgcctagg cgccgcggcc gcctagaaga   20640
cgcacagggc gctagtctac gcggcaggct gccgactagc gcctaggcgg gcctaatcgc   20700
cgcctagtcg gcgcctagct gaacactgta tcgtgacgag tccatggcaa ccactgcttt   20760
ctggaatatg caggagagct gcacatcttt gtattaatag aagaagaaag gggagcggac   20820
cccattacat cacacacatt acaacactag aaactaacat atgatcaccg actaacactg   20880
agagaacacg acccacaacg ctgttttaac ccagcaactc ttcaacctgg aggaaagaca   20940
gggccttggc tcgagtcaag gacccttggc tccagtcaag gaccagagca ccgcctcttc   21000
cctagccacc ctaaaggctg tgaccaagct aggattacat ccatcaaaga cacgtctatt   21060
cctatgcttc catatggtcc aagcacctaa gataactaaa gaattgaaac cctccctcaa   21120
atgatcagat gccagagagc tgctagtctt ccaccacgac tcgaaggtaa tgactgttgt   21180
gcaagctgtc cttaggtgca agcgtgcaag tgactcttct agtccgttag atcatgatcc   21240
```

-continued

```
aaccatagat gcaattgtgg tttgttagtt aaaaaaaaca caacccgatg gtgggagggt   21300
ttaaatgtta aatgtgacat acggttggat catgatataa cggatcagga ggctcccttg   21360
cacacttaca cctaaggaca gcttgcacaa cagtagttgc cgtcacattt agctctaata   21420
acttattaag ccgcatttcg tgacgagtcc aatgtaaaat cttagtggat agtggtagta   21480
gcttgttgta aaggtgaaca aatgttttca gttagggact tataaggctt tggcttgttt   21540
gcttcaaatt cattgtatga tcttatacca cttggctgaa aatagtattt ttcatgcatg   21600
gaagtaaact acttagtttt tcaactactg gcttatatat atgtattttc tataggagga   21660
ggtacaagtt gacactgaga gtgatgacga agagcaacaa atctacaatc ctctcaagtt   21720
gccgatgggt tgggatggca aacctatccc ctactggctg tacaagctac atggccttgg   21780
gcaggtaact agttgtcata tttgggagta tatttcctag tagcttgtta cctctagtct   21840
tagtcagtga gatggcacgg cagtagcacc aatgctttca ctcatggtgc agattgacta   21900
gttggcaccc attaagatgc cagtcattta tgaactgatc agtcattact tcacatctat   21960
gacaccaaaa atgaaattct cttatgctat ataaattggg tacccatcct tgttcagtga   22020
ctaatactta tgcaagtcag taaggatgtt agcagtatag gatgaatatg aagtcttcta   22080
ttaagttttc tgcagtgtta gcattcaata gtaacctttt ggagtttaat ttctagggac   22140
tttccaccta atgaggtgat tgttttctcc tcacccagtc tagagcatta aaagattcta   22200
tttctgcata aactgtatct gtatgcaaat ctagaaatgt gatccatctg actaatgtat   22260
ttatctgaac acatgttcac gtttgttagt gcattttctc tcttcaggaa gtgctttgaa   22320
ccagaaaatc aaggcacctt tttcttttat gcttagtaag ctctagcaaa tttgtttttct   22380 gatgcatttt taactgttat ggacttatgc tttgttcagg aattcaagtg tgagatatgt   22440
ggaaaccata gctattgggg gcgaagggct tatgagcgtc atttcaagga atggcgtcat   22500
cagcatggga tgcgatgcct tggcattccc aatactaaga atttcaatga aattacatcc   22560
atcgaggtat atcatctctt gttttattga tattattttta tttacttggt atacttattg   22620
gtgcatagct tactacaatg tttatttact ttttactagt ataatactaa tacccgtgcg   22680
ttggaacggt acacaatcgt atttcatgat attggttggg aagggcgagg ctgtagccgc   22740
aatgcaacca atggttgaac gaagtaaacc agtcatatgg atcctcccta aaaaatacca   22800
ataataaata aatttaatat caaagtgagc atattgtcta tagacaagat aataaaaata   22860
aatattatac tttattttag ccaaaaagac cgagaaagat gagttgaaaa agaactcaat   22920
ccctattttt atagagctct ctctagctcg tcctccttca actaacgggc tgttactata   22980
tgtgtacggc ttcctgtcgt attgcgcttg gtggcttctc acggtctata tatggtgtaa   23040
caaccttgat gacttataac tcaagacatt gactccatat aaacacacat tatggctgcc   23100
ggttttaaag acccacaaca tcttccactg aacctatgcc cttttatttt ctcttagaca   23160
cacgcattaa acacacaatt cacggacaga tagaatcata aagatgtctc tagctattgc   23220
acaataatct gatagagaag gaaaacatgc ctcaacaatt atcaaacaga ggtcatgcat   23280
ggattcatga tgcaacatgc atgaaccatg catgagttga tcggtgtcca gtatcgtctt   23340
gcgtcatgca cgaggggtgg ttaattctga tcaagctaca agaaacaaat gaactaatga   23400
atcaaatgcc ttgaacaaca gccatccact acgaggggtg gttaattctg atcaagctac   23460
aagaaacaaa tgaactaatg aaccaaatgc cttgaacaac agccatccac tacgtatctg   23520
tcgtccatgc tttgcatcgg aaggccattc ccaactgtcc tagctctagc aaaacagtac   23580
acactcaact tcgaatggag ctacaataaa atgctcgcca aggaaccatc gcaaacacac   23640
```

-continued

```
gacgaccttg tagctcctca ctcctgagga agcacttgtc ctagccgctt gcaatgactt   23700
gttacgcttc gtctctcttc tccgccacaa cggtcgtgac cacgttgtgc ggcagcacta   23760
catgccacgt tgtgcggcat cttgctcacg ccccgtcgct cttgtcgccg tcgatcgtgc   23820
ccgtggccac ccttccaccg atgctcgcca taccaacggt tcccgcggtg ggcgccgtgc   23880
cacaggtcca tgtggtgccg aataccgccg tcatgccaaa agggacactg ccgccaatcc   23940
tcgccgtcgt gtcgaaggtt ggcgctttga tgccaatgcc tgtcgtcgtg cctaaggttg   24000
gtgagttgcc gttgatgccc tctctgtggc ccgtgcctaa ccgctcatgc cctccatccc   24060
gacagcatcg gtctccatta ggtcccacga acgtgacaca gactcggtgg acaggcctgt   24120
gaagatgctt gtggagtcaa tgagccagaa aatcagatgt acgtacgtgc gtaccttgga   24180
ggacgtaggc aagtcggact agctgaagag cgtcaggcca ccggtggcga gcaaatccac   24240
caccgctatc gtttgagggt cctcaatatg acttttcgta gccaggttgg tgggcggatt   24300
aggatgagta aaacggctct accccgcagc ttctggaacc actttccccg cgtttctatg   24360
catggaagac gcagcgtgtg tgggtctgct gaaaccgctt tccctatccc ctacggagcg   24420
acgtgcatgg gttgttgggc tcgcggtgca tttggcgcgg gctcacttgt catgccgatc   24480
gttgctatga acagaagaca tgacatgtgc gggtttctgt catttcgtgg gtgactgagg   24540
cattcgtgcg tcgtgcgggg cgctgattcg ctgaggacga gtggatagac gaattggatt   24600
agatgcgatt gatgtgaaga gaatgtatct tgtgggtcat ttcaaacaat agaagtagtt   24660
atttgtaaaa atatgacgcg ggacgaccgt cgaaacttgt gctttaatat atatatatat   24720
atatatatat atatatatat atatatatat atatatatta ttgcaaagga gacgatggat   24780
catgatctat ttcaaagcta aggtatatga tatattccgt aattgtaata gcagaaaaaa   24840
cgaccggaaa agacacttgt tttctctgtg ggccatgact ccgtcacgtg aagaatctga   24900
accgtggtga gatttggtga cggggacgca tggcgccaag ccgacctcgc gactgccggc   24960
aggtttggcg gatttgtctg cacaaaagcg tcgctgcttc ctatgtttac gtctagcgat   25020
ccagcctcaa gctagtttga cagtggtcaa agtcggcgag gggtcatttc aaacaacata   25080
aggtggtatt tgtaaaaata tgacgtggga cgatcgttga aactggtgct ttaatatagt   25140
agagatgaga tttgcccata tcatattggc ttccacattt ccttgtcctt tatttattct   25200
gtttccttat ttgaaacaga atgcaaaaga atgcatgtct gccatattct tgacattggc   25260
cggtttattg tatattgtat gtgctttaac atttatttct actctcagga ggcgaaagcg   25320
ctctgggaga aaattcaagc acgacaaggg gtgaataagt ggcggccaga cctagaggaa   25380
gagtatgaag atcaggaagg caacatctac aacaagaaga cctacactga cctgcagcgt   25440
caaggcctga tctagggctc ctgctggtta aagttgtcgg gatttgttca gaacttatct   25500
catgtagttg taactctgaa aatattggcc catctggcat acattttatg taataacatg   25560
attctccgga actcatgtgc ttttcccggt tgtcatggtt gtctcgtgtg tctgtttgcc   25620
cagcttggtc gtccgtagct atgttatgtt ttatataatc gtaaatgtgt tattgtatta   25680
agcacaagtt ggtgtttgca tcacgtaaaa catattttta taaaaaaatt agaaaaaaat   25740
aaaactaggc tgtttttggt cta                                          25763
```

```
<210> SEQ ID NO 27
<211> LENGTH: 1515
<212> TYPE: DNA
<213> ORGANISM: Zea mays
```

-continued

```
<400> SEQUENCE: 27
atggcgtcaa cggtgctgga ggcgacgcgg gcggcccatg aggatctgga gaggctggag     60
cggctcgcgg tgagcgagct gcaacgggag cccgctaacc cgcgtgaccg cctctttcag    120
tcccaccgcg tccgccacat gctcgacctc gtcgtctcca cctccggcaa gctcgtggaa    180
atttacgagg acaaggacaa tgctaggaag gatgagatca cactcatct tactgcaccc     240 acgcaaagtg gactgtttag caagtactat gaaaggctca agagatccg tgaatatcat     300 cggcggaacc catctgcccg ctttgttagt acaactgatg actatgaaga gcttctaaag    360
gaggaaccag ttattgaatt cactggcgag gaaacttttg ccgttacct tgacttgcat     420 gagctttata atgagttcat aaattccaag ttcggaacac tgatggaata ttcagcttat    480
gttggctgtt ctcccagac ggacaagatc tcacatagtc ataaagctac cagaaaatac     540
agagaatact tggaacatat tttggaatat ctgacatcat ttctgtatcg cacagagcca    600
ttgcaagaca ttgataagat ttttttaaag ctggagagtg aattcgagga acaatgggcc    660
aatgaaggaa tacttggatg ggggaataaa gggacagaaa aagagtctga aatagatctc    720
gattactaca gcacagttga agaacttgtt gagcttggcc cagaaaaatt aaaacaggct    780
ttagctgctc gaggtttgaa gagtggcggt actgttcaac agcgtgcaga tcgtcttttc    840
ttgttgaagg ttacaccgtt ggaacaacta gataggaagc attttgccaa agttccacat    900
actaaagatg gctcaaacac agctcctaat ggtaatgctt tcaaggagga tatgaagaaa    960
gaaattgcat tgatggaagt gaagatgaaa cgtctttgtg agctgctaga tgaggccttt   1020
gtaaggacaa aggaaaatgc ggagaagaag cttactttga catatgaaga gatggaagca   1080
gaacgggaag aggaggaggt acaagttgac actgagagtg atgacgaaga gcaacaaatc   1140
tacaatcctc tcaagttgcc gatgggttgg gatggcaaac ctatccccta ctggctgtac   1200
aagctacatg gccttgggca ggaattcaag tgtgagatat gtggaaacca tagctattgg   1260
gggcgaaggg cttatgagcg tcatttcaag gaatggcgtc atcagcatgg gatgcgatgc   1320
cttggcattc ccaatactaa gaatttcaat gaaattacat ccatcgagga ggcgaaagcg   1380
ctctgggaga aaattcaagc acgacaaggg gtgaataagg gcggccagac cctagaggaa   1440
gagtatgaag atcaggaagg caacatctac aacaagaaga cctacactga cctgcagcgt   1500
caaggcctga tctag                                                    1515
```

```
<210> SEQ ID NO 28
<211> LENGTH: 504
<212> TYPE: PRT
<213> ORGANISM: Zea mays

<400> SEQUENCE: 28

Met Ala Ser Thr Val Leu Glu Ala Thr Arg Ala Ala His Glu Asp Leu
1               5                   10                  15

Glu Arg Leu Glu Arg Leu Ala Val Ser Glu Leu Gln Arg Glu Pro Ala
            20                  25                  30

Asn Pro Arg Asp Arg Leu Phe Gln Ser His Arg Val Arg His Met Leu
        35                  40                  45

Asp Leu Val Val Ser Thr Ser Gly Lys Leu Val Glu Ile Tyr Glu Asp
    50                  55                  60

Lys Asp Asn Ala Arg Lys Asp Glu Ile Asn Thr His Leu Thr Ala Pro
65                  70                  75                  80

Thr Gln Ser Gly Leu Phe Ser Lys Tyr Tyr Glu Arg Leu Lys Glu Ile
                85                  90                  95
```

-continued

```
Arg Glu Tyr His Arg Arg Asn Pro Ser Ala Arg Phe Val Ser Thr Thr
            100             105             110

Asp Asp Tyr Glu Glu Leu Leu Lys Glu Glu Pro Val Ile Glu Phe Thr
            115             120             125

Gly Glu Glu Thr Phe Gly Arg Tyr Leu Asp Leu His Glu Leu Tyr Asn
            130             135             140

Glu Phe Ile Asn Ser Lys Phe Gly Thr Leu Met Glu Tyr Ser Ala Tyr
145             150             155             160

Val Gly Cys Phe Ser Gln Thr Asp Lys Ile Ser His Ser His Lys Ala
                165             170             175

Thr Arg Lys Tyr Arg Glu Tyr Leu Glu His Ile Leu Glu Tyr Leu Thr
            180             185             190

Ser Phe Leu Tyr Arg Thr Glu Pro Leu Gln Asp Ile Asp Lys Ile Phe
            195             200             205

Leu Lys Leu Glu Ser Glu Phe Glu Glu Gln Trp Ala Asn Glu Gly Ile
    210             215             220

Leu Gly Trp Gly Asn Lys Gly Thr Glu Lys Glu Ser Glu Ile Asp Leu
225             230             235             240

Asp Tyr Tyr Ser Thr Val Glu Glu Leu Val Glu Leu Gly Pro Glu Lys
                245             250             255

Leu Lys Gln Ala Leu Ala Ala Arg Gly Leu Lys Ser Gly Gly Thr Val
            260             265             270

Gln Gln Arg Ala Asp Arg Leu Phe Leu Leu Lys Val Thr Pro Leu Glu
            275             280             285

Gln Leu Asp Arg Lys His Phe Ala Lys Val Pro His Thr Lys Asp Gly
    290             295             300

Ser Asn Thr Ala Pro Asn Gly Asn Ala Phe Lys Glu Asp Met Lys Lys
305             310             315             320

Glu Ile Ala Leu Met Glu Val Lys Met Lys Arg Leu Cys Glu Leu Leu
                325             330             335

Asp Glu Ala Phe Val Arg Thr Lys Glu Asn Ala Glu Lys Lys Leu Thr
            340             345             350

Leu Thr Tyr Glu Glu Met Glu Ala Glu Arg Glu Glu Glu Val Gln
            355             360             365

Val Asp Thr Glu Ser Asp Asp Glu Glu Gln Gln Ile Tyr Asn Pro Leu
    370             375             380

Lys Leu Pro Met Gly Trp Asp Gly Lys Pro Ile Pro Tyr Trp Leu Tyr
385             390             395             400

Lys Leu His Gly Leu Gly Gln Glu Phe Lys Cys Glu Ile Cys Gly Asn
                405             410             415

His Ser Tyr Trp Gly Arg Arg Ala Tyr Glu Arg His Phe Lys Glu Trp
                420             425             430

Arg His Gln His Gly Met Arg Cys Leu Gly Ile Pro Asn Thr Lys Asn
            435             440             445

Phe Asn Glu Ile Thr Ser Ile Glu Glu Ala Lys Ala Leu Trp Glu Lys
    450             455             460

Ile Gln Ala Arg Gln Gly Val Asn Lys Trp Arg Pro Asp Leu Glu Glu
465             470             475             480

Glu Tyr Glu Asp Gln Glu Gly Asn Ile Tyr Asn Lys Lys Thr Tyr Thr
                485             490             495

Asp Leu Gln Arg Gln Gly Leu Ile
            500
```

```
<210> SEQ ID NO 29
<211> LENGTH: 1479
<212> TYPE: DNA
<213> ORGANISM: Triticum aestivum

<400> SEQUENCE: 29
atggcgtcgt ctgtgctgga ggccacgcgg gcggcgcacg aggacctcga gcggttggag      60
cgcctggcgg tgcgcgagct ccagcgcgac ccggccaacg cccgcgaccg cctcttccag     120
tcccaccgcg tccgtcacat gctcgatctc gtcgtctcca cgtccgacaa gctggtggaa     180
atctatgaag acaaggacgg tgctaggaag gatgagatct ccacccatct taccgcgccg     240
gtgcaaagtg acatcttccc caagtactat gaaaggctga agagattcg tgattaccat     300 agacggaatc actctgcccg tttcgtcagt gaaactgatg attatgagga gctactaaag     360
gaggaaccag ctattgaatt cactggcgag gaagcatttg gccggtactt ggacctacat     420
gagctctaca acgagttcat aaattccaag tttggatcac taatggaata ctcagcatac     480
gttggcactt ttgctcagac tgaaaaaatc gcacataatc taaaagctac caggccttac     540
aaagaatatt tggagcatat tttggaatat ctgatgtcat ttctgtatcg tacagaaccg     600
ttgcaagata ttgagaagat ttttacaaag ttggaaagtg agtttgaaga acagtggacc     660
aatggcgaag ttcctggatg ggagaataag ggcacagaga agaatctgt gttgcaagag      720 tctgcagtag accttgatta ctacagtact gttgaagagc ttgtagagct tggtccggaa     780
aagttgaagg aggctttaac tgctcgtgga ttgaagggtg gcggcactgt tcaacagcgt     840
gctgagcggc tttttcttgct gaagcataca cccttggaaa aactggatcg taagcatttt     900
gccaaaggtg atgatttgaa gaaggaaatt gctttgactg aaatgaagat gaagcgctta     960
tgtgagattc tcgatgaggt cattgtaaga acaaaggaaa acgcggagaa gaagctgacc    1020
ttgacctatg aagaaatgga agcagagcgg gaagaggaag aagtgcaagc tgatagtgaa    1080
agtgatgatg aagaccaaca aatctacaac cccctcaagt taccaatggg ctgggacggg    1140
aaacctatcc cttattggct ctataagctt cacggtcttg gtcaggaatt caagtgtgaa    1200
atatgtggta accacagtta ctgggggcga agggcttatg agcgccattt caaggagtgg    1260
cgccatcagc atgggatgcg atgccttggc attcctaata ctaagaactt caatgaaatt    1320
acatccatca aggaggcgac gacactctgg gagagaatac aagcaaagca agggcagaac    1380
aagtggcggc cagacttgga agaagagtat gaagataagg atggaaacat ctacaacaaa    1440
aagacctata ctgatctgca cgcgccaaggc ctgatatag                         1479

<210> SEQ ID NO 30
<211> LENGTH: 492
<212> TYPE: PRT
<213> ORGANISM: Triticum aestivum

<400> SEQUENCE: 30

Met Ala Ser Ser Val Leu Glu Ala Thr Arg Ala Ala His Glu Asp Leu
1               5                   10                  15

Glu Arg Leu Glu Arg Leu Ala Val Arg Glu Leu Gln Arg Asp Pro Ala
                20                  25                  30

Asn Ala Arg Asp Arg Leu Phe Gln Ser His Arg Val Arg His Met Leu
            35                  40                  45

Asp Leu Val Val Ser Thr Ser Asp Lys Leu Val Glu Ile Tyr Glu Asp
        50                  55                  60

Lys Asp Gly Ala Arg Lys Asp Glu Ile Ser Thr His Leu Thr Ala Pro
```

```
65                      70                      75                      80

Val Gln Ser Asp Ile Phe Pro Lys Tyr Tyr Glu Arg Leu Lys Glu Ile
                85                      90                      95

Arg Asp Tyr His Arg Arg Asn His Ser Ala Arg Phe Val Ser Glu Thr
            100                     105                     110

Asp Asp Tyr Glu Glu Leu Leu Lys Glu Glu Pro Ala Ile Glu Phe Thr
            115                     120                     125

Gly Glu Glu Ala Phe Gly Arg Tyr Leu Asp Leu His Glu Leu Tyr Asn
        130                     135                     140

Glu Phe Ile Asn Ser Lys Phe Gly Ser Leu Met Glu Tyr Ser Ala Tyr
145                     150                     155                     160

Val Gly Thr Phe Ala Gln Thr Glu Lys Ile Ala His Asn Leu Lys Ala
                165                     170                     175

Thr Arg Pro Tyr Lys Glu Tyr Leu Glu His Ile Leu Glu Tyr Leu Met
            180                     185                     190

Ser Phe Leu Tyr Arg Thr Glu Pro Leu Gln Asp Ile Glu Lys Ile Phe
            195                     200                     205

Thr Lys Leu Glu Ser Glu Phe Glu Glu Gln Trp Thr Asn Gly Glu Val
        210                     215                     220

Pro Gly Trp Glu Asn Lys Gly Thr Glu Lys Glu Ser Val Leu Gln Glu
225                     230                     235                     240

Ser Ala Val Asp Leu Asp Tyr Tyr Ser Thr Val Glu Glu Leu Val Glu
                245                     250                     255

Leu Gly Pro Glu Lys Leu Lys Glu Ala Leu Thr Ala Arg Gly Leu Lys
            260                     265                     270

Gly Gly Gly Thr Val Gln Gln Arg Ala Glu Arg Leu Phe Leu Leu Lys
            275                     280                     285

His Thr Pro Leu Glu Lys Leu Asp Arg Lys His Phe Ala Lys Gly Asp
        290                     295                     300

Asp Leu Lys Lys Glu Ile Ala Leu Thr Glu Met Lys Met Lys Arg Leu
305                     310                     315                     320

Cys Glu Ile Leu Asp Glu Val Ile Val Arg Thr Lys Glu Asn Ala Glu
                325                     330                     335

Lys Lys Leu Thr Leu Thr Tyr Glu Glu Met Glu Ala Glu Arg Glu Glu
            340                     345                     350

Glu Glu Val Gln Ala Asp Ser Glu Ser Asp Asp Glu Asp Gln Gln Ile
            355                     360                     365

Tyr Asn Pro Leu Lys Leu Pro Met Gly Trp Asp Gly Lys Pro Ile Pro
        370                     375                     380

Tyr Trp Leu Tyr Lys Leu His Gly Leu Gly Gln Glu Phe Lys Cys Glu
385                     390                     395                     400

Ile Cys Gly Asn His Ser Tyr Trp Gly Arg Arg Ala Tyr Glu Arg His
                405                     410                     415

Phe Lys Glu Trp Arg His Gln His Gly Met Arg Cys Leu Gly Ile Pro
            420                     425                     430

Asn Thr Lys Asn Phe Asn Glu Ile Thr Ser Ile Lys Glu Ala Thr Thr
            435                     440                     445

Leu Trp Glu Arg Ile Gln Ala Lys Gln Gly Gln Asn Lys Trp Arg Pro
        450                     455                     460

Asp Leu Glu Glu Glu Tyr Glu Asp Lys Asp Gly Asn Ile Tyr Asn Lys
465                     470                     475                     480

Lys Thr Tyr Thr Asp Leu Gln Arg Gln Gly Leu Ile
                485                     490
```

```
<210> SEQ ID NO 31
<211> LENGTH: 1479
<212> TYPE: DNA
<213> ORGANISM: Triticum aestivum

<400> SEQUENCE: 31
atggcgtcgt ctgtgctgga ggccacgcgg gcggcgcacg aggacctcga gcggttagag      60
cgcctggcgg tgcgcgagct gcagcgcgac cccgccaacg cgcgcgaccg cctcttccag     120
tcccaccgcg tccgccacat gctcgatctc gtcgtctcca cttccgacaa gctggtggaa     180
atctatgaag acaaggacgg tgctaggaag gatgagatct ccacccatct taccgcgccg     240
gtgcaaagtg acatcttccc caagtactat gaaaggctga agagattcg tgattaccat      300 agacggaatc actctgcccg tttcgtcagt gaaactgatg attatgagga gctactaaag     360
gaggaaccag ctattgaatt cactggcgag gaagcatttg ccggtactt ggacctacat      420 gagctctaca acgagttcat aaattccaag tttggatcac taatggaata tcggcatac      480 gttggcactt ttgctcagac tgaaaaaatc gcacataatc taaaagctac caggccatac     540
aaagaatatt tggagcatat tttggaatat ctgatgtcgt ttctgtatcg tacagaaccg     600
ttgcaagata ttgagaagat ttttacaaag ttggaaagtg agtttgaaga acagtggacc     660
aatggcgaag ttcctggatg ggagaataag ggcacagaga aagaatctgt gttgcaagag     720
tctgcagtag accttgatta ctatagtact gttgaagagc ttgtagagct tggtccggaa     780
aagttgaagg aggctttaac tgctcgtggg ttgaagggtg gcggcactgt tcaacagcgt     840
gctgagcgac ttttcttgct gaagcataca cccttggaaa aactggatcg caagcatttt     900
gccaaaggtg atgatctgaa gaaggaaatt gctttgattg aaatgaagat gaagcgctta     960
tgtgagattc tcgatgaggt cattgtaaga acaaaggaaa acgcggagaa gaagctgacc    1020
ttgacctatg aagaaatgga agcagagcgg gaagaggaag aagtacaagc tgatagtgaa    1080
agtgatgatg aagaccaaca aatctacaac cccctcaagt taccaatggg ctgggacggg    1140
aaacctatcc cttattggct ctataagctt cacggtcttg gtcaggaatt caagtgtgaa    1200
atatgtggta accacagtta ctgggggcga agagcttatg agcgccattt caaggagtgg    1260
cgccatcagc atgggatgcg atgccttggc attcctaata ctaagaattt caatgaaatt    1320
acatccatca aggaggcgac ggcactctgg gagagaatac aagcaaagca agggcagaac    1380
aagtggcggc cagacttgga agaagagtac gaagataagg atggaaacat ctacaacaaa    1440
aagacctata ctgatctgca gcgccaaggc ctgatatag                           1479

<210> SEQ ID NO 32
<211> LENGTH: 492
<212> TYPE: PRT
<213> ORGANISM: Triticum aestivum

<400> SEQUENCE: 32

Met Ala Ser Ser Val Leu Glu Ala Thr Arg Ala Ala His Glu Asp Leu
1               5                   10                  15

Glu Arg Leu Glu Arg Leu Ala Val Arg Glu Leu Gln Arg Asp Pro Ala
            20                  25                  30

Asn Ala Arg Asp Arg Leu Phe Gln Ser His Arg Val Arg His Met Leu
        35                  40                  45

Asp Leu Val Val Ser Thr Ser Asp Lys Leu Val Glu Ile Tyr Glu Asp
    50                  55                  60
```

-continued

```
Lys Asp Gly Ala Arg Lys Asp Glu Ile Ser Thr His Leu Thr Ala Pro
65                  70                  75                  80

Val Gln Ser Asp Ile Phe Pro Lys Tyr Tyr Glu Arg Leu Lys Glu Ile
                85                  90                  95

Arg Asp Tyr His Arg Arg Asn His Ser Ala Arg Phe Val Ser Glu Thr
            100                 105                 110

Asp Asp Tyr Glu Glu Leu Leu Lys Glu Glu Pro Ala Ile Glu Phe Thr
            115                 120                 125

Gly Glu Glu Ala Phe Gly Arg Tyr Leu Asp Leu His Glu Leu Tyr Asn
        130                 135                 140

Glu Phe Ile Asn Ser Lys Phe Gly Ser Leu Met Glu Tyr Ser Ala Tyr
145                 150                 155                 160

Val Gly Thr Phe Ala Gln Thr Glu Lys Ile Ala His Asn Leu Lys Ala
                165                 170                 175

Thr Arg Pro Tyr Lys Glu Tyr Leu Glu His Ile Leu Glu Tyr Leu Met
            180                 185                 190

Ser Phe Leu Tyr Arg Thr Glu Pro Leu Gln Asp Ile Glu Lys Ile Phe
            195                 200                 205

Thr Lys Leu Glu Ser Glu Phe Glu Glu Gln Trp Thr Asn Gly Glu Val
        210                 215                 220

Pro Gly Trp Glu Asn Lys Gly Thr Glu Lys Glu Ser Val Leu Gln Glu
225                 230                 235                 240

Ser Ala Val Asp Leu Asp Tyr Tyr Ser Thr Val Glu Glu Leu Val Glu
                245                 250                 255

Leu Gly Pro Glu Lys Leu Lys Glu Ala Leu Thr Ala Arg Gly Leu Lys
            260                 265                 270

Gly Gly Gly Thr Val Gln Gln Arg Ala Glu Arg Leu Phe Leu Leu Lys
        275                 280                 285

His Thr Pro Leu Glu Lys Leu Asp Arg Lys His Phe Ala Lys Gly Asp
        290                 295                 300

Asp Leu Lys Lys Glu Ile Ala Leu Ile Glu Met Lys Met Lys Arg Leu
305                 310                 315                 320

Cys Glu Ile Leu Asp Glu Val Ile Val Arg Thr Lys Glu Asn Ala Glu
                325                 330                 335

Lys Lys Leu Thr Leu Thr Tyr Glu Glu Met Glu Ala Glu Arg Glu Glu
            340                 345                 350

Glu Glu Val Gln Ala Asp Ser Glu Ser Asp Asp Glu Asp Gln Gln Ile
            355                 360                 365

Tyr Asn Pro Leu Lys Leu Pro Met Gly Trp Asp Gly Lys Pro Ile Pro
        370                 375                 380

Tyr Trp Leu Tyr Lys Leu His Gly Leu Gly Gln Glu Phe Lys Cys Glu
385                 390                 395                 400

Ile Cys Gly Asn His Ser Tyr Trp Gly Arg Arg Ala Tyr Glu Arg His
                405                 410                 415

Phe Lys Glu Trp Arg His Gln His Gly Met Arg Cys Leu Gly Ile Pro
            420                 425                 430

Asn Thr Lys Asn Phe Asn Glu Ile Thr Ser Ile Lys Glu Ala Thr Ala
        435                 440                 445

Leu Trp Glu Arg Ile Gln Ala Lys Gln Gly Gln Asn Lys Trp Arg Pro
        450                 455                 460

Asp Leu Glu Glu Glu Tyr Glu Asp Lys Asp Gly Asn Ile Tyr Asn Lys
465                 470                 475                 480

Lys Thr Tyr Thr Asp Leu Gln Arg Gln Gly Leu Ile
```

-continued

```
                     485                 490
```

```
<210> SEQ ID NO 33
<211> LENGTH: 1479
<212> TYPE: DNA
<213> ORGANISM: Triticum aestivum

<400> SEQUENCE: 33
atggcgtcgt ctgtgctgga ggccacgcgg gcggcgcacg aggacctcga gcggttagag      60
cgcctggcgg tgcgcgagct gcagcgcgac cccgccaacg cgcgcgaccg cctcttccag     120
tcccaccgcg tccgccacat gctcgatctc gtcgtctcca cttccgacaa gctggtggaa     180
atctatgaag acaaggacgg tgctaggaag gatgagatct ccacccatct taccgcgccg     240
gtgcaaagtg acatcttccc caagtactat gaaaggctga agagattcg tgattaccat     300 agacggaatc actctgcccg tttcgtcagt gaaactgatg attatgagga gctactaaag     360
gaggaaccag ctattgaatt cactggcgag gaagcatttg gccggtactt ggacctacat     420
gagctctaca cgagttcat aaattccaag tttggatcac taatggaata ctcagcatac     480
gttggcactt ttgctcagac tgaaaaaatc gcacataatc taaaagctac caggccatac     540
aaagaatatt tggagcatat tttggaatat ctgatgtcat ttctgtatcg tacagaaccg     600
ttgcaagata ttgagaagat ttttacaaag ttggaaagtg agtttgaaga acagtggatc     660
aatggcgaag ttcctggatg ggagaataag ggcacagaga aagaatctgt gttgcaagag     720
tctgcagtag accttgatta ctacagtact gttgaagagc ttgtagagct tggtccggaa     780
aagttgaagg aggctttaac tgctcgtgga ttgaaggggtg gtggcactgt tcaacagcgt     840
gctgagcgac ttttcttgct gaagcataca cccttggaaa agctggatcg taagcatttt     900 gccaaggtg atgatttgaa gaaggaaatt gctttgattg aaatgaagat gaagcgctta     960
tgtgagattc tcgatgaggt cattgtaaga acaaaggaaa atgcggagaa gaagctgacc    1020
ttgacctatg aagaaatgga agcagagcgg gaagaggaag aagtacaagc tgatagtgaa    1080
agtgatgatg aagaccaaca aatctacaac ccctcaagt taccaatggg ctgggacggg    1140
aaacctatcc cttattggct ctataagctt cacggtcttg gtcaggaatt caagtgtgaa    1200
atatgtggta accacagtta ctgggggcga agggcttatg agcgccattt caaggagtgg    1260
cgccatcagc atgggatgcg atgccttggc attcctaata ctaagaactt caatgaaatt    1320
acatccatca aggaagcgac agcactctgg gagagaatac aagcaaagca agggcagaac    1380
aagtggcggc cagacttgga agaagagtat gaagataagg atggaaacat ctacaacaaa    1440
aagacctata ctgatctgca cgcgccaaggc ctgatatag                           1479

<210> SEQ ID NO 34
<211> LENGTH: 492
<212> TYPE: PRT
<213> ORGANISM: Triticum aestivum

<400> SEQUENCE: 34

Met Ala Ser Ser Val Leu Glu Ala Thr Arg Ala Ala His Glu Asp Leu
1               5                   10                  15

Glu Arg Leu Glu Arg Leu Ala Val Arg Glu Leu Gln Arg Asp Pro Ala
            20                  25                  30

Asn Ala Arg Asp Arg Leu Phe Gln Ser His Arg Val Arg His Met Leu
        35                  40                  45

Asp Leu Val Val Ser Thr Ser Asp Lys Leu Val Glu Ile Tyr Glu Asp
    50                  55                  60
```

-continued

```
Lys Asp Gly Ala Arg Lys Asp Glu Ile Ser Thr His Leu Thr Ala Pro
65                  70                  75                  80

Val Gln Ser Asp Ile Phe Pro Lys Tyr Tyr Glu Arg Leu Lys Glu Ile
                85                  90                  95

Arg Asp Tyr His Arg Arg Asn His Ser Ala Arg Phe Val Ser Glu Thr
            100                 105                 110

Asp Asp Tyr Glu Glu Leu Leu Lys Glu Glu Pro Ala Ile Glu Phe Thr
            115                 120                 125

Gly Glu Glu Ala Phe Gly Arg Tyr Leu Asp Leu His Glu Leu Tyr Asn
        130                 135                 140

Glu Phe Ile Asn Ser Lys Phe Gly Ser Leu Met Glu Tyr Ser Ala Tyr
145                 150                 155                 160

Val Gly Thr Phe Ala Gln Thr Glu Lys Ile Ala His Asn Leu Lys Ala
                165                 170                 175

Thr Arg Pro Tyr Lys Glu Tyr Leu Glu His Ile Leu Glu Tyr Leu Met
            180                 185                 190

Ser Phe Leu Tyr Arg Thr Glu Pro Leu Gln Asp Ile Glu Lys Ile Phe
            195                 200                 205

Thr Lys Leu Glu Ser Glu Phe Glu Glu Gln Trp Ile Asn Gly Glu Val
        210                 215                 220

Pro Gly Trp Glu Asn Lys Gly Thr Glu Lys Glu Ser Val Leu Gln Glu
225                 230                 235                 240

Ser Ala Val Asp Leu Asp Tyr Tyr Ser Thr Val Glu Glu Leu Val Glu
                245                 250                 255

Leu Gly Pro Glu Lys Leu Lys Glu Ala Leu Thr Ala Arg Gly Leu Lys
            260                 265                 270

Gly Gly Gly Thr Val Gln Gln Arg Ala Glu Arg Leu Phe Leu Leu Lys
        275                 280                 285

His Thr Pro Leu Glu Lys Leu Asp Arg Lys His Phe Ala Lys Gly Asp
    290                 295                 300

Asp Leu Lys Lys Glu Ile Ala Leu Ile Glu Met Lys Met Lys Arg Leu
305                 310                 315                 320

Cys Glu Ile Leu Asp Glu Val Ile Val Arg Thr Lys Glu Asn Ala Glu
                325                 330                 335

Lys Lys Leu Thr Leu Thr Tyr Glu Glu Met Glu Ala Glu Arg Glu Glu
            340                 345                 350

Glu Glu Val Gln Ala Asp Ser Glu Ser Asp Asp Glu Asp Gln Gln Ile
            355                 360                 365

Tyr Asn Pro Leu Lys Leu Pro Met Gly Trp Asp Gly Lys Pro Ile Pro
    370                 375                 380

Tyr Trp Leu Tyr Lys Leu His Gly Leu Gly Gln Glu Phe Lys Cys Glu
385                 390                 395                 400

Ile Cys Gly Asn His Ser Tyr Trp Gly Arg Arg Ala Tyr Glu Arg His
                405                 410                 415

Phe Lys Glu Trp Arg His Gln His Gly Met Arg Cys Leu Gly Ile Pro
            420                 425                 430

Asn Thr Lys Asn Phe Asn Glu Ile Thr Ser Ile Lys Glu Ala Thr Ala
            435                 440                 445

Leu Trp Glu Arg Ile Gln Ala Lys Gln Gly Gln Asn Lys Trp Arg Pro
        450                 455                 460

Asp Leu Glu Glu Glu Tyr Glu Asp Lys Asp Gly Asn Ile Tyr Asn Lys
465                 470                 475                 480
```

Lys Thr Tyr Thr Asp Leu Gln Arg Gln Gly Leu Ile
        485                 490

<210> SEQ ID NO 35
<211> LENGTH: 3518
<212> TYPE: DNA
<213> ORGANISM: Zea mays

<400> SEQUENCE: 35
ctgcaccaac aggtcccgcc agcaccaacc caacgcaacc cagcgtcccg tcgcaacgat      60
acaatagaag ccgcacgaac cccgcgctgc gctgttctgg agaggtcccg tgcgcgcccg     120
aaccctccgc cggttgcgct catgctcacg cctacgacgt cgcccgcgcg ccgggccgcg     180
ctcgcaccgc cacatcaccg cactacacga accttcccga acgccaccgc tccccgccct     240
acgcctgtat ttaagcggac gcacctatcc gcctcactcc gatcaactca ggtagcagag     300
cgaagcatca atcagcgagc gaaccggcca gaaaaagcac aaagtagtcc tcctccattt     360
cgaatcgcgc tcatagtcac agggctttag cagagatggc gggcaacaag ggagagggcc     420
cggcgatcgg catcgacctc ggcacgacct actcctgcgt cggggtctgg cagcatgacc     480
gggtggagat tatcgccaac gaccagggca accgcaccac gccgtcgtac gtggcgttca     540
ccgacaccga gaggctcatc ggcgacgccg ccaagaacca ggtcgccatg aatcccacca     600
acaccgtctt cggtatgccc atgttcttcc cctgaataat tctagttcca tagtttcagt     660
ttcctcttat ttaatatttt agaaataaaa acaatcgcca cggctttcgc tgatacttgc     720
ctctcagcag tcattgagtc atgctctgct cccactctat ttttgcggca gctcatgaat     780
cacttgttgc atgttctaga tatatctaga tcacaatttc acaataattt tgagttgtaa     840
aacctttttt tttttgctgt ttatcgtttc aattacatta gtttgctatg taagtttgtc     900
ttgaaatagc aactcctttt tttttacctt tgttcattca acagatcatt acaaaatatt     960
tataggattt ttagttgtaa aatattaata gtacccttta catgtatgtc agatgattat    1020
tttttgttat tgtttatgaa agggttattt gatcatcgtt tagctataga aaaatcatga    1080
atcatcttta gttaattttc tttttactgt actagtcact ggtgtaagat tattgtctga    1140
cgtggtgtaa gattattgtc tgaattttca gaccactgag atactgcaac tcctacacta    1200
ttacactcat aatttttttc tccaaatggg aggaaagtag cacagaaatc ggtaattatc    1260
catcaactgt attgcctaac cgctctgtgt ttcttccatg aagatgccaa gcgactcatc    1320
ggccggcgct tctcggaccc gtctgtgcag gcggacatga agatgtggcc attcaaggtc    1380
gtcccaggcc ccgccgacaa gccaatgatc gtggtgactt acaagggcga ggagaagaag    1440
ttctcggccg aggagatctc ctccatggtg ctcaccaaga tgaaggagat cgccgaggcc    1500
tacctcagca ccaccatcaa gaacgccgtc attaccgtgc cggcctactt caatgactcg    1560
cagcgccagg ccaccaagga cgccggcgtc attgccggcc tcaacgtcac gcgcatcatc    1620
aacgagccca cggccgccgc catcgcctac ggactcgaca agaaggccac cagcactggc    1680
gagaagaacg tgctcatctt cgaccttggc ggtggcacct ttgatgtgtc catcctcacc    1740
attgaggagg gcatcttcga ggtcaaggcc acggctggtg acacccacct gggaggcgag    1800
gacttcgaca accgcctggt gaaccacttc gtgatggagt caagaggaa acacaagaag    1860 gacatcagcg gcaacccgag ggcgctccgg cggctgcgta ccgcgtgcga gagggcgaag    1920
aggacgctct cctccaccgc ccagaccacc attgagatcg actcgctcta cgagggcatc    1980
gacttctacg cgaccatcac ccgggccagg ttcgaggagc ttaacatgga cctcttcagg    2040

-continued

```
aagtgcatgg agcccgtgga gaagtgcctc cgcgacgcca agatggacaa gtcacagatc      2100
cacgacgtcg tgctcgtcgg aggttccacc cgtatcccca aggtgcagca gctgctccag      2160
gacttcttca acggcaagga gttgtgcaag agcatcaacc ctgacgaggc cgtcgcgtac      2220
ggcgccgctg tccaggccgc catcctcagc ggcgagggca accagaaggt gcaggacctg      2280
ctccttctcg atgtcacgcc gctctcgctc gggctggaga ctgcaggcgg tgtcatgacc      2340
gtgctgatcc cgaggaacac caccatcccc accaagaagg agcaggtgtt ctccacctac      2400
tccgacaacc agcccggcgt gctgatccag gtgtacgagg gtgagaggac gaggaccaag      2460
gacaacaacc tgctcggcaa gttcgagctg accggcatcc cgccggcgcc acggggcgtg      2520
ccccagatca acgtgacctt cgacatcgac gcgaacggca tcctgaacgt gtcggcggag      2580
gacaagacga cggggaagaa gaacaagatc accatcacca acgacaaggg ccggctgagc      2640
aaggaagaga tcgagcgcat ggtgcaggag gcggagaagt acaagaccga ggacgaggag      2700
gtgaagcgca aggtggaggc ccgcaacgcg ctggagaact acgcgtataa catgcgcaac      2760
acggtgcggg acgagaagat cgcgtcgaag ctgcccgccg atgacaagaa gaagatcgag      2820
gacacgatcg aggacgccat caagtggctc gacggcaacc agctcgcgga ggccgaggag      2880
ttcgaggaca agatgaagga gctggagagc atctgcaacc ccatcatctc acagatgtac      2940
cagggcggcg cgggcgctgc gggcatggac gaggatgtgc ccggcggtgg cgccggcaac      3000
ggaggtggca gcggcgccgg gcccaagatt gaggaggtcg actgagcgag ccatggacgg      3060
tgatgatctg gatgggaagc ttctgtgcgt gcggtgcagc tagagagtgt gctacgtgaa      3120
ctcgtgaagg cgtattaatc tgtgtgtgcg ataataatct gggggttaaca cctgcagggt      3180 gttctctgtt tccgttgtca agtggttgta ggttcagtag ggtgaaagtg tgaggcatat      3240
ccattaggct tagtaaaata gtaaccctag tgttactgta accgcctccg cgagttcagg      3300
agtctataaa tatatcagta tgtaatactg tttgttttc tcgctatgca cgttctagca      3360
tccaatcatc ccatacctct gccattcctg aacaccccgt gtgcttcaga gtatccaaaa      3420
tccgccagag ccagagtcaa ctcgttggtg atgaaatgtg tgcacacacc agcgcactgg      3480
aagacaagca aaaagtcctt cagtatatgt tttgggac                              3518
```

<210> SEQ ID NO 36
<211> LENGTH: 1959
<212> TYPE: DNA
<213> ORGANISM: Zea mays

<400> SEQUENCE: 36

```
atggcgggca acaagggaga gggcccggcg atcggcatcg acctcggcac gacctactcc        60
tgcgtcgggg tctggcagca tgaccggggtg gagattatcg ccaacgacca gggcaaccgc       120
accacgccgt cgtacgtggc gttcaccgac accgagaggc tcatcggcga cgccgccaag       180
aaccaggtcg ccatgaatcc caccaacacc gtcttcgatg ccaagcgact catcggccgg       240
cgcttctcgg acccgtctgt gcaggcggac atgaagatgt ggccattcaa ggtcgtccca       300
ggccccgccg acaagccaat gatcgtggtg acttacaagg gcgaggagaa gaagttctcg       360
gccgaggaga tctcctccat ggtgctcacc aagatgaagg agatcgccga ggcctacctc       420
agcaccacca tcaagaacgc cgtcattacc gtgccggcct acttcaatga ctcgcagcgc       480
caggccacca aggacgccgg cgtcattgcc ggcctcaacg tcacgcgcat catcaacgag       540
cccacggccg ccgccatcgc ctacggactc gacaagaagg ccaccagcac tggcgagaag       600
aacgtgctca tcttcgacct tggcggtggc accctttgatg tgtccatcct caccattgag       660
```

-continued

```
gagggcatct tcgaggtcaa ggccacggct ggtgacaccc acctgggagg cgaggacttc      720
gacaaccgcc tggtgaacca cttcgtgatg gagttcaaga ggaaacacaa gaaggacatc      780
agcggcaacc cgagggcgct ccggcggctg cgtaccgcgt gcgagagggc gaagaggacg      840
ctctcctcca ccgcccagac caccattgag atcgactcgc tctacgaggg catcgacttc      900
tacgcgacca tcacccgggc caggttcgag gagcttaaca tggacctctt caggaagtgc      960
atggagcccg tggagaagtg cctccgcgac gccaagatgg acaagtcaca gatccacgac     1020
gtcgtgctcg tcggaggttc cacccgtatc cccaaggtgc agcagctgct ccaggacttc     1080
ttcaacggca aggagttgtg caagagcatc aaccctgacg aggccgtcgc gtacggcgcc     1140
gctgtccagg ccgccatcct cagcggcgag ggcaaccaga aggtgcagga cctgctcctt     1200
ctcgatgtca cgccgctctc gctcgggctg gagactgcag cggtgtcat gaccgtgctg     1260 atcccgagga acaccaccat ccccaccaag aaggagcagg tgttctccac ctactccgac     1320
aaccagcccg gcgtgctgat ccaggtgtac gagggtgaga ggacgaggac caaggacaac     1380
aacctgctcg gcaagttcga gctgaccggc atcccgccgg cgccacgggg cgtgccccag     1440
atcaacgtga ccttcgacat cgacgcgaac ggcatcctga acgtgtcggc ggaggacaag     1500
acgacgggga agaagaacaa gatcaccatc accaacgaca agggccggct gagcaaggaa     1560
gagatcgagc gcatggtgca ggaggcggag aagtacaaga ccgaggacga ggaggtgaag     1620
cgcaaggtgg aggcccgcaa cgcgctggag aactacgcgt ataacatgcg caacacggtg     1680
cgggacgaga gatcgcgtc gaagctgccc gccgatgaca agaagaagat cgaggacacg     1740
atcgaggacg ccatcaagtg gctcgacggc aaccagctcg cggaggccga ggagttcgag     1800
gacaagatga aggagctgga gagcatctgc aaccccatca tctcacagat gtaccagggc     1860
ggcgcgggcg ctgcgggcat ggacgaggat gtgcccggcg gtggcgccgg caacggaggt     1920
ggcagcggcg ccgggcccaa gattgaggag gtcgactga                           1959
```

```
<210> SEQ ID NO 37
<211> LENGTH: 652
<212> TYPE: PRT
<213> ORGANISM: Zea mays

<400> SEQUENCE: 37

Met Ala Gly Asn Lys Gly Glu Gly Pro Ala Ile Gly Ile Asp Leu Gly
1               5                   10                  15

Thr Thr Tyr Ser Cys Val Gly Val Trp Gln His Asp Arg Val Glu Ile
                20                  25                  30

Ile Ala Asn Asp Gln Gly Asn Arg Thr Thr Pro Ser Tyr Val Ala Phe
            35                  40                  45

Thr Asp Thr Glu Arg Leu Ile Gly Asp Ala Ala Lys Asn Gln Val Ala
        50                  55                  60

Met Asn Pro Thr Asn Thr Val Phe Asp Ala Lys Arg Leu Ile Gly Arg
65                  70                  75                  80

Arg Phe Ser Asp Pro Ser Val Gln Ala Asp Met Lys Met Trp Pro Phe
                85                  90                  95

Lys Val Val Pro Gly Pro Ala Asp Lys Pro Met Ile Val Val Thr Tyr
                100                 105                 110

Lys Gly Glu Glu Lys Lys Phe Ser Ala Glu Glu Ile Ser Ser Met Val
        115                 120                 125

Leu Thr Lys Met Lys Glu Ile Ala Glu Ala Tyr Leu Ser Thr Thr Ile
        130                 135                 140
```

```
Lys Asn Ala Val Ile Thr Val Pro Ala Tyr Phe Asn Asp Ser Gln Arg
145             150             155             160

Gln Ala Thr Lys Asp Ala Gly Val Ile Ala Gly Leu Asn Val Thr Arg
            165             170             175

Ile Ile Asn Glu Pro Thr Ala Ala Ile Ala Tyr Gly Leu Asp Lys
            180             185             190

Lys Ala Thr Ser Thr Gly Glu Lys Asn Val Leu Ile Phe Asp Leu Gly
            195             200             205

Gly Gly Thr Phe Asp Val Ser Ile Leu Thr Ile Glu Glu Gly Ile Phe
            210             215             220

Glu Val Lys Ala Thr Ala Gly Asp Thr His Leu Gly Gly Glu Asp Phe
225             230             235             240

Asp Asn Arg Leu Val Asn His Phe Val Met Glu Phe Lys Arg Lys His
            245             250             255

Lys Lys Asp Ile Ser Gly Asn Pro Arg Ala Leu Arg Arg Leu Arg Thr
            260             265             270

Ala Cys Glu Arg Ala Lys Arg Thr Leu Ser Ser Thr Ala Gln Thr Thr
            275             280             285

Ile Glu Ile Asp Ser Leu Tyr Glu Gly Ile Asp Phe Tyr Ala Thr Ile
            290             295             300

Thr Arg Ala Arg Phe Glu Glu Leu Asn Met Asp Leu Phe Arg Lys Cys
305             310             315             320

Met Glu Pro Val Glu Lys Cys Leu Arg Asp Ala Lys Met Asp Lys Ser
            325             330             335

Gln Ile His Asp Val Val Leu Val Gly Gly Ser Thr Arg Ile Pro Lys
            340             345             350

Val Gln Gln Leu Leu Gln Asp Phe Phe Asn Gly Lys Glu Leu Cys Lys
            355             360             365

Ser Ile Asn Pro Asp Glu Ala Val Ala Tyr Gly Ala Ala Val Gln Ala
            370             375             380

Ala Ile Leu Ser Gly Glu Gly Asn Gln Lys Val Gln Asp Leu Leu Leu
385             390             395             400

Leu Asp Val Thr Pro Leu Ser Leu Gly Leu Glu Thr Ala Gly Gly Val
            405             410             415

Met Thr Val Leu Ile Pro Arg Asn Thr Thr Ile Pro Thr Lys Lys Glu
            420             425             430

Gln Val Phe Ser Thr Tyr Ser Asp Asn Gln Pro Gly Val Leu Ile Gln
            435             440             445

Val Tyr Glu Gly Glu Arg Thr Arg Thr Lys Asp Asn Asn Leu Leu Gly
            450             455             460

Lys Phe Glu Leu Thr Gly Ile Pro Pro Ala Pro Arg Gly Val Pro Gln
465             470             475             480

Ile Asn Val Thr Phe Asp Ile Asp Ala Asn Gly Ile Leu Asn Val Ser
            485             490             495

Ala Glu Asp Lys Thr Thr Gly Lys Lys Asn Lys Ile Thr Ile Thr Asn
            500             505             510

Asp Lys Gly Arg Leu Ser Lys Glu Glu Ile Glu Arg Met Val Gln Glu
            515             520             525

Ala Glu Lys Tyr Lys Thr Glu Asp Glu Glu Val Lys Arg Lys Val Glu
            530             535             540

Ala Arg Asn Ala Leu Glu Asn Tyr Ala Tyr Asn Met Arg Asn Thr Val
545             550             555             560
```

-continued

```
Arg Asp Glu Lys Ile Ala Ser Lys Leu Pro Ala Asp Asp Lys Lys Lys
            565                 570                 575

Ile Glu Asp Thr Ile Glu Asp Ala Ile Lys Trp Leu Asp Gly Asn Gln
            580                 585                 590

Leu Ala Glu Ala Glu Glu Phe Glu Asp Lys Met Lys Glu Leu Glu Ser
        595                 600                 605

Ile Cys Asn Pro Ile Ile Ser Gln Met Tyr Gln Gly Gly Ala Gly Ala
        610                 615                 620

Ala Gly Met Asp Glu Asp Val Pro Gly Gly Gly Ala Gly Asn Gly Gly
625                 630                 635                 640

Gly Ser Gly Ala Gly Pro Lys Ile Glu Glu Val Asp
                645                 650
```

```
<210> SEQ ID NO 38
<211> LENGTH: 1974
<212> TYPE: DNA
<213> ORGANISM: Triticum aestivum

<400> SEQUENCE: 38
atggcgagca agggaggcaa caaggggag ggccctgcca tcggcatcga cctcggcacc      60
acctactcct gcgtcggcgt ctggcagcat gatcgggtgg agatcgtcgc caacgaccag     120
ggcaaccgca ccacgccgtc ctacgtcgcc ttcaccgaca ccgagcggct catcggcgac     180
gccgccaaga accaggtcgc catgaacccc accaacaccg tttttgatgc caagcgactc     240
atcggacggc gcttctcgga cgcatccgta cagtcggaca tgaagatgtg gccgttcaag     300
gtggtccccg cgccggcga caagccgatg atcgtggtca cctacaaggg ggaggagaag     360
accttctctg ctgaggagat atcctccatg gtgctcacca agatgaggga gatcgccgag     420
gccttcctca gcacgaccat caacaacgcc gtcgtcaccg tcccggccta cttcaacgac     480
tcccagcgcc aggccaccaa ggacgccggc gtgatcgcgg gcctcaacgt catgcgcata     540
atcaacgagc ccaccgccgc ggccatcgcc tacggcctcg acaagaaggc caccagcacc     600
ggggagaaga acgtgctcat cttcgacctc ggcggcggca ccttcgacgt gtccatcctc     660
accatcgagg aaggcatatt cgaggtcaag tccaccgccg cgacaccca cctgggaggc      720 gaggacttcg acaaccggat ggtgaaccac ttcgtgcaag agttcaagag gaagaacaag     780
aaggacatca gcggcaaccc aagggcgctc cggcggctga ggacggcgtg cgagagggcc     840
aagaggacgc tctcttccac cgcccagacc accattgaga tcgactcgct gtacgagggg     900
atcgacttct acgcgaccat cacccgtgcc aggttcgagg agctcaacat ggacctcttc     960
cgcaagtgca tggagcccgt ggagaagtgc ctccgggacg ccaagatgga caagacccaa    1020
atccacgaca tcgtgctcgt cggaggctcc acccggatcc ccaaggtgca gcagctcctc    1080
caggacttct tcaacgggaa ggagctctgc aagagcatca accccgacga ggccgtcgcg    1140
tacggcgccg ccgtgcaggc cgccatcctc agcggcgagg gcaaccaaaa ggtgcaggac    1200
ctgctcctgc tcgacgtgac gccgctctcg ctcgggttgg acacggccgg aggcgtgatg    1260
accaccctga tcccgaggaa caccaccatc ccaaccaaga aggagcaggt cttctccacc    1320
tactcggaca ccagcccgg cgtgctgatc caggtgtacg agggcgagag gacgaggacc    1380
aaggacaaca acctgctggg caagttcgag ctgtccggca tcccgccggc gcccagggc    1440 gtgccccaga tcacggtgac cttcgacatc gacgcgaacg gcatcctgaa cgtgtcggca    1500
gaggacaaga cgacgggaca gaagaacaag atcaccatca ccaacgacaa gggtcggctg    1560
agcaaggagg agatcgagcg catggtgcag gaggcggaga agtacaagtc ggaggacgag    1620
```

```
caggtgcggc acaaggtgga ggcccgcaac gcgctggaga actacgcgta caacatgcgc      1680
aacacgctgc gggacgacaa gatcgcgtcc aagctccccg ccgacgacaa gaagaagatc      1740
gaggactcga tcgaggacgc catcaagtgg ctcgacggca accagctcgc cgaggcggac      1800
gagttcgagg acaagatgaa ggagctggag agcatctgca accccatcat ctccaagatg      1860
taccagggcg ccggcccggg cggcgcggcc ggcatggacg aggacatgcc cggcggcggc      1920
gcgggcaccg cggcgggag cggtgccggg cccaagatcg aagaagtgga ctaa           1974
```

```
<210> SEQ ID NO 39
<211> LENGTH: 657
<212> TYPE: PRT
<213> ORGANISM: Triticum aestivum

<400> SEQUENCE: 39

Met Ala Ser Lys Gly Gly Asn Lys Gly Glu Gly Pro Ala Ile Gly Ile
1               5                   10                  15

Asp Leu Gly Thr Thr Tyr Ser Cys Val Gly Val Trp Gln His Asp Arg
            20                  25                  30

Val Glu Ile Val Ala Asn Asp Gln Gly Asn Arg Thr Thr Pro Ser Tyr
        35                  40                  45

Val Ala Phe Thr Asp Thr Glu Arg Leu Ile Gly Asp Ala Ala Lys Asn
    50                  55                  60

Gln Val Ala Met Asn Pro Thr Asn Thr Val Phe Asp Ala Lys Arg Leu
65                  70                  75                  80

Ile Gly Arg Arg Phe Ser Asp Ala Ser Val Gln Ser Asp Met Lys Met
                85                  90                  95

Trp Pro Phe Lys Val Val Pro Gly Ala Gly Asp Lys Pro Met Ile Val
            100                 105                 110

Val Thr Tyr Lys Gly Glu Glu Lys Thr Phe Ser Ala Glu Glu Ile Ser
        115                 120                 125

Ser Met Val Leu Thr Lys Met Arg Glu Ile Ala Glu Ala Phe Leu Ser
        130                 135                 140

Thr Thr Ile Asn Asn Ala Val Val Thr Val Pro Ala Tyr Phe Asn Asp
145                 150                 155                 160

Ser Gln Arg Gln Ala Thr Lys Asp Ala Gly Val Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Lys Ala Thr Ser Thr Gly Glu Lys Asn Val Leu Ile Phe
        195                 200                 205

Asp Leu Gly Gly Gly Thr Phe Asp Val Ser Ile Leu Thr Ile Glu Glu
    210                 215                 220

Gly Ile Phe Glu Val Lys Ser Thr Ala Gly Asp Thr His Leu Gly Gly
225                 230                 235                 240

Glu Asp Phe Asp Asn Arg Met Val Asn His Phe Val Gln Glu Phe Lys
                245                 250                 255

Arg Lys Asn Lys Lys Asp Ile Ser Gly Asn Pro Arg Ala Leu Arg Arg
            260                 265                 270

Leu Arg Thr Ala Cys Glu Arg Ala Lys Arg Thr Leu Ser Ser Thr Ala
        275                 280                 285

Gln Thr Thr Ile Glu Ile Asp Ser Leu Tyr Glu Gly Ile Asp Phe Tyr
    290                 295                 300

Ala Thr Ile Thr Arg Ala Arg Phe Glu Glu Leu Asn Met Asp Leu Phe
```

-continued

```
305              310              315              320

Arg Lys Cys Met Glu Pro Val Glu Lys Cys Leu Arg Asp Ala Lys Met
                325              330              335

Asp Lys Thr Gln Ile His Asp Ile Val Leu Val Gly Gly Ser Thr Arg
                340              345              350

Ile Pro Lys Val Gln Gln Leu Leu Gln Asp Phe Phe Asn Gly Lys Glu
                355              360              365

Leu Cys Lys Ser Ile Asn Pro Asp Glu Ala Val Ala Tyr Gly Ala Ala
                370              375              380

Val Gln Ala Ala Ile Leu Ser Gly Glu Gly Asn Gln Lys Val Gln Asp
385              390              395              400

Leu Leu Leu Leu Asp Val Thr Pro Leu Ser Leu Gly Leu Glu Thr Ala
                405              410              415

Gly Gly Val Met Thr Thr Leu Ile Pro Arg Asn Thr Thr Ile Pro Thr
                420              425              430

Lys Lys Glu Gln Val Phe Ser Thr Tyr Ser Asp Asn Gln Pro Gly Val
                435              440              445

Leu Ile Gln Val Tyr Glu Gly Glu Arg Thr Arg Thr Lys Asp Asn Asn
                450              455              460

Leu Leu Gly Lys Phe Glu Leu Ser Gly Ile Pro Pro Ala Pro Arg Gly
465              470              475              480

Val Pro Gln Ile Thr Val Thr Phe Asp Ile Asp Ala Asn Gly Ile Leu
                485              490              495

Asn Val Ser Ala Glu Asp Lys Thr Thr Gly Gln Lys Asn Lys Ile Thr
                500              505              510

Ile Thr Asn Asp Lys Gly Arg Leu Ser Lys Glu Glu Ile Glu Arg Met
                515              520              525

Val Gln Glu Ala Glu Lys Tyr Lys Ser Glu Asp Glu Gln Val Arg His
                530              535              540

Lys Val Glu Ala Arg Asn Ala Leu Glu Asn Tyr Ala Tyr Asn Met Arg
545              550              555              560

Asn Thr Leu Arg Asp Asp Lys Ile Ala Ser Lys Leu Pro Ala Asp Asp
                565              570              575

Lys Lys Lys Ile Glu Asp Ser Ile Glu Asp Ala Ile Lys Trp Leu Asp
                580              585              590

Gly Asn Gln Leu Ala Glu Ala Asp Glu Phe Glu Asp Lys Met Lys Glu
                595              600              605

Leu Glu Ser Ile Cys Asn Pro Ile Ile Ser Lys Met Tyr Gln Gly Ala
                610              615              620

Gly Pro Gly Gly Ala Ala Gly Met Asp Glu Asp Met Pro Gly Gly Gly
625              630              635              640

Ala Gly Thr Gly Gly Gly Ser Gly Ala Gly Pro Lys Ile Glu Glu Val
                645              650              655

Asp
```

<210> SEQ ID NO 40
<211> LENGTH: 1974
<212> TYPE: DNA
<213> ORGANISM: Triticum aestivum

<400> SEQUENCE: 40

```
atggcgagca agggaggcaa caagggggag ggccctgcaa tcggcatcga cctcggcacc      60
acatactcct gcgtcggcgt ctggcagcat gaccgggtgg agatcgtcgc caacgaccag     120
```

-continued

```
ggcaaccgca ccacgccgtc ctacgtcgcc ttcaccgaca ccgagcggct catcggcgac    180
gccgccaaga accaggtcgc catgaacccc accaacaccg tttttgatgc caagcgactc    240
atcggacggc gcttctcgga cgcatccgtg cagtcggata tgaagatgtg gccgttcaag    300
gtggtccccg gcgccggcga caagccgatg atcgtggtca cctacaaggg ggaggagaag    360
accttctctg ccgaggagat atcctccatg gtgctcacca agatgaggga gatcgccgag    420
gccttcctca gcacaaccat caacaacgcc gtcgtcactg tcccggccta cttcaacgac    480
tcccagcgcc aggccaccaa ggacgccggc gtcatcgccg gcctcaacgt catgcgcatc    540
atcaacgagc cgaccgcggc ggccatcgct tacggcctcg acaaaaaggc caccagcacc    600
ggggagaaga acgtgctcat cttcgacctc ggcggcggca ccttcgatgt gtccatcctc    660
accatcgagg aaggcatatt cgaggtcaag tccaccgccg gggacaccca cctggggggc    720
gaggacttcg acaaccggat ggtgaaccac ttcgtgcaag agttcaagag gaagaacaag    780
aaggacatca gcggcaaccc gagggcgctc cggcggctga ggacggcgtg cgagagggcc    840
aagaggacgc tctcttccac cgcccagacc accattgaga ttgactcgct ctacgagggg    900
attgacttct acgcgaccat caccccgtgcc aggttcgagg agctcaacat ggacctcttc    960
cgcaagtgca tggagcccgt cgagaagtgc ctccggacg ccaagatgga caagacccaa     1020
atccacgaca tcgtgctcgt cggaggctcc acccggatcc ccaaggtgca gcagctcctc     1080
caggacttct tcaacgggaa ggagctctgc aagagcatca accccgacga ggccgtcgcg     1140
tacggcgccg ccgtgcaggc tgccatcctc agcggcgagg gcaatcagaa ggtgcaggac     1200
ctgctcctgc tcgatgtgac gccgctctcg ctcgggttgg agacggccgg aggcgtgatg     1260
actactctga tcccgaggaa caccaccatc cccaccaaga aggagcaggt cttctccacc     1320
tactcggaca ccagcccgg cgtgctgatc caggtgtacg agggcgagag gacgaggacc      1380
aaggacaaca acctgctggg caagttcgag ctgtccggca tcccgccggc gcccaggggc     1440
gtcccccaga tcacggtgac cttcgacatc gacgcgaacg gcatcctgaa cgtgtccgcg      1500
gaggacaaga cgaccgggca gaagaacaag atcaccatca ccaacgacaa ggggcggctg     1560
agcaaggagg agatcgagcg catggtgcag gaggcggaga agtacaagtc tgaggacgag      1620
caggtgcggc acaaggtgga ggcccgcaac gcgctggaga actacgcgta caacatgcgc     1680
aacacggtgc gggacgagaa gatcgcgtcc aagctccccg ccgaagacaa gaagaagatc     1740
gaggactcca tcgaggacgc catcaagtgg ctcgacggca accagctggc cgaggccgac     1800
gagttcgagg acaagatgaa ggagctggag aacatctgca accccatcat ctccaagatg     1860
taccagggcg ccggcccggg cggcgcggcc ggcatggacg aggacatgcc cggcggcggc      1920
gcgggcaccg gcggtgggag cggtgccggg cccaagatcg aagaagtgga ctga           1974
```

<210> SEQ ID NO 41
<211> LENGTH: 657
<212> TYPE: PRT
<213> ORGANISM: Triticum aestivum

<400> SEQUENCE: 41

```
Met Ala Ser Lys Gly Gly Asn Lys Gly Glu Gly Pro Ala Ile Gly Ile
1               5                   10                  15

Asp Leu Gly Thr Thr Tyr Ser Cys Val Gly Val Trp Gln His Asp Arg
                20                  25                  30

Val Glu Ile Val Ala Asn Asp Gln Gly Asn Arg Thr Thr Pro Ser Tyr
        35                  40                  45
```

-continued

```
Val Ala Phe Thr Asp Thr Glu Arg Leu Ile Gly Asp Ala Ala Lys Asn
    50                  55                  60

Gln Val Ala Met Asn Pro Thr Asn Thr Val Phe Asp Ala Lys Arg Leu
65                  70                  75                  80

Ile Gly Arg Arg Phe Ser Asp Ala Ser Val Gln Ser Asp Met Lys Met
                85                  90                  95

Trp Pro Phe Lys Val Val Pro Gly Ala Gly Asp Lys Pro Met Ile Val
                100                 105                 110

Val Thr Tyr Lys Gly Glu Glu Lys Thr Phe Ser Ala Glu Glu Ile Ser
                115                 120                 125

Ser Met Val Leu Thr Lys Met Arg Glu Ile Ala Glu Ala Phe Leu Ser
    130                 135                 140

Thr Thr Ile Asn Asn Ala Val Val Thr Val Pro Ala Tyr Phe Asn Asp
145                 150                 155                 160

Ser Gln Arg Gln Ala Thr Lys Asp Ala Gly Val Ile Ala Gly Leu Asn
                165                 170                 175

Val Met Arg Ile Ile Asn Glu Pro Thr Ala Ala Ala Ile Ala Tyr Gly
                180                 185                 190

Leu Asp Lys Lys Ala Thr Ser Thr Gly Glu Lys Asn Val Leu Ile Phe
                195                 200                 205

Asp Leu Gly Gly Gly Thr Phe Asp Val Ser Ile Leu Thr Ile Glu Glu
    210                 215                 220

Gly Ile Phe Glu Val Lys Ser Thr Ala Gly Asp Thr His Leu Gly Gly
225                 230                 235                 240

Glu Asp Phe Asp Asn Arg Met Val Asn His Phe Val Gln Glu Phe Lys
                245                 250                 255

Arg Lys Asn Lys Lys Asp Ile Ser Gly Asn Pro Arg Ala Leu Arg Arg
                260                 265                 270

Leu Arg Thr Ala Cys Glu Arg Ala Lys Arg Thr Leu Ser Ser Thr Ala
                275                 280                 285

Gln Thr Thr Ile Glu Ile Asp Ser Leu Tyr Glu Gly Ile Asp Phe Tyr
    290                 295                 300

Ala Thr Ile Thr Arg Ala Arg Phe Glu Glu Leu Asn Met Asp Leu Phe
305                 310                 315                 320

Arg Lys Cys Met Glu Pro Val Glu Lys Cys Leu Arg Asp Ala Lys Met
                325                 330                 335

Asp Lys Thr Gln Ile His Asp Ile Val Leu Val Gly Gly Ser Thr Arg
                340                 345                 350

Ile Pro Lys Val Gln Gln Leu Leu Gln Asp Phe Phe Asn Gly Lys Glu
                355                 360                 365

Leu Cys Lys Ser Ile Asn Pro Asp Glu Ala Val Ala Tyr Gly Ala Ala
    370                 375                 380

Val Gln Ala Ala Ile Leu Ser Gly Glu Gly Asn Gln Lys Val Gln Asp
385                 390                 395                 400

Leu Leu Leu Leu Asp Val Thr Pro Leu Ser Leu Gly Leu Glu Thr Ala
                405                 410                 415

Gly Gly Val Met Thr Thr Leu Ile Pro Arg Asn Thr Thr Ile Pro Thr
                420                 425                 430

Lys Lys Glu Gln Val Phe Ser Thr Tyr Ser Asp Asn Gln Pro Gly Val
                435                 440                 445

Leu Ile Gln Val Tyr Glu Gly Glu Arg Thr Arg Thr Lys Asp Asn Asn
    450                 455                 460

Leu Leu Gly Lys Phe Glu Leu Ser Gly Ile Pro Pro Ala Pro Arg Gly
```

-continued

```
465                470                475                480
Val Pro Gln Ile Thr Val Thr Phe Asp Ile Asp Ala Asn Gly Ile Leu
                485                490                495

Asn Val Ser Ala Glu Asp Lys Thr Thr Gly Gln Lys Asn Lys Ile Thr
            500                505                510

Ile Thr Asn Asp Lys Gly Arg Leu Ser Lys Glu Glu Ile Glu Arg Met
            515                520                525

Val Gln Glu Ala Glu Lys Tyr Lys Ser Glu Asp Glu Gln Val Arg His
        530                535                540

Lys Val Glu Ala Arg Asn Ala Leu Glu Asn Tyr Ala Tyr Asn Met Arg
545                550                555                560

Asn Thr Val Arg Asp Glu Lys Ile Ala Ser Lys Leu Pro Ala Glu Asp
                565                570                575

Lys Lys Lys Ile Glu Asp Ser Ile Glu Asp Ala Ile Lys Trp Leu Asp
            580                585                590

Gly Asn Gln Leu Ala Glu Ala Asp Glu Phe Glu Asp Lys Met Lys Glu
            595                600                605

Leu Glu Asn Ile Cys Asn Pro Ile Ile Ser Lys Met Tyr Gln Gly Ala
        610                615                620

Gly Pro Gly Gly Ala Ala Gly Met Asp Glu Asp Met Pro Gly Gly Gly
625                630                635                640

Ala Gly Thr Gly Gly Gly Ser Gly Ala Gly Pro Lys Ile Glu Glu Val
                645                650                655

Asp

<210> SEQ ID NO 42
<211> LENGTH: 1974
<212> TYPE: DNA
<213> ORGANISM: Triticum aestivum

<400> SEQUENCE: 42
atggcgagca agggaggcaa caagggggag ggccctgcga tcggcatcga cctcggcacc     60
acctactcct gcgtcggcgt atggcagcac gaccgggtgg agatcgtcgc caacgaccaa    120
ggcaaccgca ccacgccgtc ctacgtcgcc ttcaccgaca ccgagcggct catcggcgac    180
gccgccaaga accaggtcgc catgaacccc accaacaccg tttttgatgc caagcggctc    240
atcgggcggc gcttctcgga cgcatccgtg cagtcggaca tgaagatgtg ccgttcaag     300 gtggtccccg cgccggcga caaaccgatg atcgtggtca gctacaaggg ggaggagaag    360
accttctccg ccgaggagat atcctccatg gtgctcacca agatgaggga gatcgccgag    420
gccttcctca gcacgaccat caacaacgcc gtcgtcaccg tcccggcgta cttcaacgac    480
tcccagcgcc aggccaccaa ggacgccggc gtgatcgcgg tgctcaacgt catgcgcata    540
atcaacgagc ccaccgcggc ggccatcgct tacggcctcg acaagaaggc caccagcacc    600
ggggagaaga cgtgctcat cttcgacctc ggcggcggca ccttcgatgt gtccatcctc    660
accatcgagg aaggcatatt cgaggtcaag tccaccgccg gcgacaccca cctgggaggc    720
gaggacttcg acaaccggat ggtgaaccac ttcgtgcaag agttcaagag gaagaacaag    780
aaggacatca gcggcaaccc gagggcgctc cggcggctga ggacggcgtg cgagagggcg    840
aagaggaccc tctcttccac cgcccagacc accattgaga tcgactcgct ctacgagggg    900
atcgacttct acgcgaccat caccgtgcc aggttcgagg agctcaacat ggacctcttc    960
cgcaagtgca tggagcccgt cgagaagtgc ctccgggacg ccaagatgga caagacccaa   1020
```

-continued

```
atccacgaca tcgtgctcgt cggaggctcc acccggatcc ccaaggtgca gcagctcctc    1080
caggacttct tcaacgggaa ggagctctgc aagagcatca accccgacga ggccgtcgcg    1140
tacggcgccg ccgtccaggc cgccatcctc agcggcgagg gcaaccagaa ggtgcaggac    1200
ctgctcctgc tcgacgtgac gccgctctcg ctcgggttgg agacggccgg aggcgtgatg    1260
acgaccctga tcccgaggaa caccaccatc cccaccaaga aggagcaggt cttctcaacc    1320
tactcggaca accagcccgg cgtgctgatc caggtgtacg agggcgagag gacgaggacc    1380
aaggacaaca acctgctggg caagttcgag ctgtccggca tcccgtcggc gcccaggggc    1440
gtaccccaga tcacggtgac cttcgacatc gacgcgaacg gcatcctgaa cgtgtcggcg    1500
gaggacaaga cgaccgggca gaagaacaag atcaccatca ccaacgacaa ggggcggctg    1560
agcaaggagg agatcgagcg catggtgcag gaggcggaga gtacaagtc ggaggacgag     1620 caggtgcggc acaaggtgga ggcccgcaac gcgctggaga actacgcgta caacatgcgc    1680
aacacggtgc gggacgagaa gatcgcgtcc aagctccccg ccgacgacaa gaagaagatc    1740
gaggactcca tcgaggacgc catcaagtgg ctcgacggca accagctcgc cgaggccgac    1800
gagttcgagg acaagatgaa ggagctggag agcatctgca accccatcat ctccaagatg    1860
taccagggtg ctggcccggg cggcgcggcc ggcatggacg aggacatgcc cggcggcggc    1920
gcgggcaccg gcggtgggag cggtgccggg cccaagatcg aagaagtgga ctga          1974
```

<210> SEQ ID NO 43
<211> LENGTH: 657
<212> TYPE: PRT
<213> ORGANISM: Triticum aestivum

<400> SEQUENCE: 43

```
Met Ala Ser Lys Gly Gly Asn Lys Gly Glu Gly Pro Ala Ile Gly Ile
1               5                   10                  15

Asp Leu Gly Thr Thr Tyr Ser Cys Val Gly Val Trp Gln His Asp Arg
            20                  25                  30

Val Glu Ile Val Ala Asn Asp Gln Gly Asn Arg Thr Thr Pro Ser Tyr
        35                  40                  45

Val Ala Phe Thr Asp Thr Glu Arg Leu Ile Gly Asp Ala Ala Lys Asn
    50                  55                  60

Gln Val Ala Met Asn Pro Thr Asn Thr Val Phe Asp Ala Lys Arg Leu
65                  70                  75                  80

Ile Gly Arg Arg Phe Ser Asp Ala Ser Val Gln Ser Asp Met Lys Met
                85                  90                  95

Trp Pro Phe Lys Val Val Pro Gly Ala Gly Asp Lys Pro Met Ile Val
            100                 105                 110

Val Ser Tyr Lys Gly Glu Glu Lys Thr Phe Ser Ala Glu Glu Ile Ser
        115                 120                 125

Ser Met Val Leu Thr Lys Met Arg Glu Ile Ala Glu Ala Phe Leu Ser
    130                 135                 140

Thr Thr Ile Asn Asn Ala Val Val Thr Val Pro Ala Tyr Phe Asn Asp
145                 150                 155                 160

Ser Gln Arg Gln Ala Thr Lys Asp Ala Gly Val Ile Ala Gly Leu Asn
                165                 170                 175

Val Met Arg Ile Ile Asn Glu Pro Thr Ala Ala Ala Ile Ala Tyr Gly
            180                 185                 190

Leu Asp Lys Lys Ala Thr Ser Thr Gly Glu Lys Asn Val Leu Ile Phe
        195                 200                 205
```

```
Asp Leu Gly Gly Gly Thr Phe Asp Val Ser Ile Leu Thr Ile Glu Glu
    210                 215                 220

Gly Ile Phe Glu Val Lys Ser Thr Ala Gly Asp Thr His Leu Gly Gly
225                 230                 235                 240

Glu Asp Phe Asp Asn Arg Met Val Asn His Phe Val Gln Glu Phe Lys
                245                 250                 255

Arg Lys Asn Lys Lys Asp Ile Ser Gly Asn Pro Arg Ala Leu Arg Arg
                260                 265                 270

Leu Arg Thr Ala Cys Glu Arg Ala Lys Arg Thr Leu Ser Ser Thr Ala
            275                 280                 285

Gln Thr Thr Ile Glu Ile Asp Ser Leu Tyr Glu Gly Ile Asp Phe Tyr
    290                 295                 300

Ala Thr Ile Thr Arg Ala Arg Phe Glu Glu Leu Asn Met Asp Leu Phe
305                 310                 315                 320

Arg Lys Cys Met Glu Pro Val Glu Lys Cys Leu Arg Asp Ala Lys Met
                325                 330                 335

Asp Lys Thr Gln Ile His Asp Ile Val Leu Val Gly Gly Ser Thr Arg
            340                 345                 350

Ile Pro Lys Val Gln Gln Leu Leu Gln Asp Phe Phe Asn Gly Lys Glu
            355                 360                 365

Leu Cys Lys Ser Ile Asn Pro Asp Glu Ala Val Ala Tyr Gly Ala Ala
    370                 375                 380

Val Gln Ala Ala Ile Leu Ser Gly Glu Gly Asn Gln Lys Val Gln Asp
385                 390                 395                 400

Leu Leu Leu Leu Asp Val Thr Pro Leu Ser Leu Gly Leu Glu Thr Ala
                405                 410                 415

Gly Gly Val Met Thr Thr Leu Ile Pro Arg Asn Thr Thr Ile Pro Thr
                420                 425                 430

Lys Lys Glu Gln Val Phe Ser Thr Tyr Ser Asp Asn Gln Pro Gly Val
            435                 440                 445

Leu Ile Gln Val Tyr Glu Gly Glu Arg Thr Arg Thr Lys Asp Asn Asn
    450                 455                 460

Leu Leu Gly Lys Phe Glu Leu Ser Gly Ile Pro Ser Ala Pro Arg Gly
465                 470                 475                 480

Val Pro Gln Ile Thr Val Thr Phe Asp Ile Asp Ala Asn Gly Ile Leu
                485                 490                 495

Asn Val Ser Ala Glu Asp Lys Thr Thr Gly Gln Lys Asn Lys Ile Thr
                500                 505                 510

Ile Thr Asn Asp Lys Gly Arg Leu Ser Lys Glu Glu Ile Glu Arg Met
            515                 520                 525

Val Gln Glu Ala Glu Lys Tyr Lys Ser Glu Asp Glu Gln Val Arg His
    530                 535                 540

Lys Val Glu Ala Arg Asn Ala Leu Glu Asn Tyr Ala Tyr Asn Met Arg
545                 550                 555                 560

Asn Thr Val Arg Asp Glu Lys Ile Ala Ser Lys Leu Pro Ala Asp Asp
                565                 570                 575

Lys Lys Lys Ile Glu Asp Ser Ile Glu Asp Ala Ile Lys Trp Leu Asp
            580                 585                 590

Gly Asn Gln Leu Ala Glu Ala Asp Glu Phe Glu Asp Lys Met Lys Glu
            595                 600                 605

Leu Glu Ser Ile Cys Asn Pro Ile Ile Ser Lys Met Tyr Gln Gly Ala
    610                 615                 620

Gly Pro Gly Gly Ala Ala Gly Met Asp Glu Asp Met Pro Gly Gly Gly
```

-continued

```
625             630             635             640

Ala Gly Thr Gly Gly Gly Ser Gly Ala Gly Pro Lys Ile Glu Glu Val
                645                 650                 655

Asp

<210> SEQ ID NO 44
<211> LENGTH: 1259
<212> TYPE: DNA
<213> ORGANISM: Zea mays

<400> SEQUENCE: 44
cgatatttgc caaaagtttta cggttttgta tttcatcgtg tcgcccaaga aaatcgaagg      60
aacgcgccgc caccggccgc aacaaagcaa cgcaggcctc cggcctccct gaactgactt     120
cagaagtcac caacgcaccc agcacagaca gaagaccctc gccggacgct cgctctcgcc     180
ggggacaact caatcacgag gccaggatgg cccgctacga tcgcgcgatc accgtgttct     240
cacccgacgg ccacctcttc caggtcgagt acgccctcga ggccgtccgc aagggcaacg     300
ccgctgtcgg cgtccgcggt gtcgacaccg tcgtcctcgg cgtcgagaag aagtccaccc     360
ccaagctcca ggactccagg tcggtccgtc ggtacctccc cctccctccc atccaccaga     420
tctcttgacc ccgggcgccg cctcacccaa atcctccccc aaaaaatctc cgcaggtccg     480
tgcgcaagat cgcgagcctg gacacccaca tcgcgctggc gtgcgcgggg ctcaaggccg     540
acgcgcgcgt gctcatcaac cgcgctcgcg tggagtgcca gagccaccgc ctcacagtcg     600
aggaccccgt caccgtcgag tacatcacgc gctacatcgc cggcctgcag cagaagtaca     660
cgcagagcgg aggggtgcgc cccttcggcc tctccacgct catcgtcggc ttcgatccct     720
acacccagaa gcccgcgctg taccagactg acccctcggg gaccttctcc gcttggaagg     780
ccaacgcaac cggccgcaac tccaactcca tgcgcgagtt tctcgagaag aattacaagg     840
agacgtccgg taaggagacc atcaagctcg ccatcagagc actccttgag gtatacactc     900
aagcacttaa ttagcactag tggatccaaa caggcccttt tatgtgatta ttcagagaga     960
catagtactt gaagggtgtc aattgggagc aattagtata gaatgagaaa gatcaactcc    1020
ttatttataa aggcgacaat ttgtcactga agtgaaccaa atgatgtggc agtgctggac    1080
ttagaactaa gcttgcattg ctcaactcaa tgtaccactg gagtgttgaa atctatactt    1140
tgtgtgtgct gtggcagcca agtgtttcat gtgtcatggt tgattcatta tgaatagtgg    1200
tagcatcaac tatagatccc agtttaaacg atagttgcag atttcaatga aattttttat    1259

<210> SEQ ID NO 45
<211> LENGTH: 750
<212> TYPE: DNA
<213> ORGANISM: Zea mays

<400> SEQUENCE: 45
atggcccgct acgatcgcgc gatcaccgtg ttctcacccg acggccacct cttccaggtc      60
gagtacgccc tcgaggccgt ccgcaagggc aacgccgctg tcggcgtccg cggtgtcgac     120
accgtcgtcc tcggcgtcga agaagaagtcc accccccaagc tccaggactc caggtccgtg     180
cgcaagatcg cgagcctgga cacccacatc gcgctggcgt cgcgggggct caaggccgac     240
gcgcgcgtgc tcatcaaccg cgctcgcgtg gagtgccaga gccaccgcct cacagtcgag     300
gaccccgtca ccgtcgagta catcacgcgc tacatcgccg gcctgcagca gaagtacacg     360
cagagcggag gggtgcgccc cttcggcctc tccacgctca tcgtcggctt cgatccctac     420
```

```
acccagaagc ccgcgctgta ccagactgac ccctcgggga ccttctccgc ttggaaggcc          480
aacgcaaccg gccgcaactc caactccatg cgcgagtttc tcgagaagaa ttacaaggag          540
acgtccggta aggagaccat caagctcgcc atcagagcac tccttgaggt tgttgagagt          600
ggtggcaaga acatagagat tgcagtgatg acacacgagg acggccttca tgaactcgaa          660
gaggctgaga ttgatgagta tgttgccgaa attgaagcag agaaagccgc tgccgaggct          720
gcaaagaagg gtgcaccaaa ggggaactga                                           750
```

```
<210> SEQ ID NO 46
<211> LENGTH: 249
<212> TYPE: PRT
<213> ORGANISM: Zea mays

<400> SEQUENCE: 46

Met Ala Arg Tyr Asp Arg Ala Ile Thr Val Phe Ser Pro Asp Gly His
1               5                   10                  15

Leu Phe Gln Val Glu Tyr Ala Leu Glu Ala Val Arg Lys Gly Asn Ala
                20                  25                  30

Ala Val Gly Val Arg Gly Val Asp Thr Val Val Leu Gly Val Glu Lys
            35                  40                  45

Lys Ser Thr Pro Lys Leu Gln Asp Ser Arg Ser Val Arg Lys Ile Ala
        50                  55                  60

Ser Leu Asp Thr His Ile Ala Leu Ala Cys Ala Gly Leu Lys Ala Asp
65                  70                  75                  80

Ala Arg Val Leu Ile Asn Arg Ala Arg Val Glu Cys Gln Ser His Arg
                85                  90                  95

Leu Thr Val Glu Asp Pro Val Thr Val Glu Tyr Ile Thr Arg Tyr Ile
                100                 105                 110

Ala Gly Leu Gln Gln Lys Tyr Thr Gln Ser Gly Gly Val Arg Pro Phe
            115                 120                 125

Gly Leu Ser Thr Leu Ile Val Gly Phe Asp Pro Tyr Thr Gln Lys Pro
        130                 135                 140

Ala Leu Tyr Gln Thr Asp Pro Ser Gly Thr Phe Ser Ala Trp Lys Ala
145                 150                 155                 160

Asn Ala Thr Gly Arg Asn Ser Asn Ser Met Arg Glu Phe Leu Glu Lys
                165                 170                 175

Asn Tyr Lys Glu Thr Ser Gly Lys Glu Thr Ile Lys Leu Ala Ile Arg
            180                 185                 190

Ala Leu Leu Glu Val Val Glu Ser Gly Gly Lys Asn Ile Glu Ile Ala
            195                 200                 205

Val Met Thr His Glu Asp Gly Leu His Glu Leu Glu Glu Ala Glu Ile
        210                 215                 220

Asp Glu Tyr Val Ala Glu Ile Glu Ala Glu Lys Ala Ala Ala Glu Ala
225                 230                 235                 240

Ala Lys Lys Gly Ala Pro Lys Gly Asn
                245
```

```
<210> SEQ ID NO 47
<211> LENGTH: 750
<212> TYPE: DNA
<213> ORGANISM: Triticum aestivum

<400> SEQUENCE: 47
atggcccgct acgaccgagc gatcaccgtc ttctcccccg acggccacct cttccaggtt          60
gagtacgccc tcgaggccgt ccgcaagggc aacgccgccg tcggcgtccg aggcgtcgac          120
```

```
accgtcgtcc tcggtgtcga gaagaagtcc acccccaagc tccaggactc caggtccgtg       180
cgcaagatcg cgagcctgga cacccacatc gcgctggcct gcgcgggtct gaaggcggac       240
gcgcgcgtgc tcatcaaccg ggcgcgcgtc gagtgccaga gccaccgcct caccgtcgag       300
gaccccgtca ctgtcgagta catcacgcgc tacatcgccg gcctgcagca gaagtacacg       360
cagagcggag gggtgcgccc gttcgggctc tccacgctca tagttggctt cgacccctat       420
accgagaagc ccgcgctgta ccagaccgac ccctccggca ccttctccgc ctggaaggcc       480
aacgccaccg gccgcaactc caactccatg cgcgaattcc ttgagaagaa ttacaaggag       540
acgtccggca aggagaccat caagcttacc atccgagccc tccttgaggt tgtcgagagt       600
ggtggcaaga acattgagat tgctgtgatg acgcacaaag atggtcttcg ccagcttgag       660
gaagaggaga tcgatgagta tgttgctgag attgaagcag agaaggccgc tgctgaggct       720
gcaaagaagg gtggcccgaa agacacataa                                        750
```

```
<210> SEQ ID NO 48
<211> LENGTH: 249
<212> TYPE: PRT
<213> ORGANISM: Triticum aestivum

<400> SEQUENCE: 48

Met Ala Arg Tyr Asp Arg Ala Ile Thr Val Phe Ser Pro Asp Gly His
1               5                   10                  15

Leu Phe Gln Val Glu Tyr Ala Leu Glu Ala Val Arg Lys Gly Asn Ala
            20                  25                  30

Ala Val Gly Val Arg Gly Val Asp Thr Val Val Leu Gly Val Glu Lys
        35                  40                  45

Lys Ser Thr Pro Lys Leu Gln Asp Ser Arg Ser Val Arg Lys Ile Ala
    50                  55                  60

Ser Leu Asp Thr His Ile Ala Leu Ala Cys Ala Gly Leu Lys Ala Asp
65                  70                  75                  80

Ala Arg Val Leu Ile Asn Arg Ala Arg Val Glu Cys Gln Ser His Arg
                85                  90                  95

Leu Thr Val Glu Asp Pro Val Thr Val Glu Tyr Ile Thr Arg Tyr Ile
            100                 105                 110

Ala Gly Leu Gln Gln Lys Tyr Thr Gln Ser Gly Gly Val Arg Pro Phe
        115                 120                 125

Gly Leu Ser Thr Leu Ile Val Gly Phe Asp Pro Tyr Thr Glu Lys Pro
    130                 135                 140

Ala Leu Tyr Gln Thr Asp Pro Ser Gly Thr Phe Ser Ala Trp Lys Ala
145                 150                 155                 160

Asn Ala Thr Gly Arg Asn Ser Asn Ser Met Arg Glu Phe Leu Glu Lys
                165                 170                 175

Asn Tyr Lys Glu Thr Ser Gly Lys Glu Thr Ile Lys Leu Thr Ile Arg
            180                 185                 190

Ala Leu Leu Glu Val Val Glu Ser Gly Gly Lys Asn Ile Glu Ile Ala
        195                 200                 205

Val Met Thr His Lys Asp Gly Leu Arg Gln Leu Glu Glu Glu Glu Ile
    210                 215                 220

Asp Glu Tyr Val Ala Glu Ile Glu Ala Glu Lys Ala Ala Ala Glu Ala
225                 230                 235                 240

Ala Lys Lys Gly Gly Pro Lys Asp Thr
                245
```

```
<210> SEQ ID NO 49
<211> LENGTH: 750
<212> TYPE: DNA
<213> ORGANISM: Triticum aestivum

<400> SEQUENCE: 49
atggcccgct acgaccgagc gatcaccgtc ttctcccccg acggccacct cttccaggtt      60
gagtacgccc tcgaggccgt ccgcaagggc aacgccgccg tcggcgtccg aggcgtcgac     120
accgtcgtcc tcggtgtcga gaagaagtcc acccccaagc tccaagactc caggtccgtg     180
cgcaagatcg cgagcctgga cacccacatc gcgttggcct cgcggggtct gaaggcggac     240
gcgcgcgtgc tcatcaaccg ggcgcgcgtc gagtgccaga gccaccgcct caccgtcgag     300
gaccccgtca ctgtcgagta catcacgcgc tacatcgccg gcctgcagca gaagtacacg     360
cagagcggag gggtgcgccc gttcgggctc tccacgctca tagttggctt cgaccccctat   420 actgagaagc ctgcgctgta ccagaccgac ccctccggca ccttctccgc ctggaaggcc     480
aacgccaccg gccgcaactc caactccatg cgcgagttcc ttgagaagaa ttacaaggag     540
acgtccggca aggagaccat caagcttacc atccgagccc tccttgaggt tgtcgagagt     600
ggtggcaaga acattgagat tgctgtgatg acgcacaaag atggtcttcg ccagcttgag     660
gaagaggaga tcgatgagta tgttgctgag attgaagcag agaaggctgc tgctgaggct     720
gcgaagaagg tggcccgaa agacacataa                                       750

<210> SEQ ID NO 50
<211> LENGTH: 249
<212> TYPE: PRT
<213> ORGANISM: Triticum aestivum

<400> SEQUENCE: 50

Met Ala Arg Tyr Asp Arg Ala Ile Thr Val Phe Ser Pro Asp Gly His
1               5                   10                  15

Leu Phe Gln Val Glu Tyr Ala Leu Glu Ala Val Arg Lys Gly Asn Ala
                20                  25                  30

Ala Val Gly Val Arg Gly Val Asp Thr Val Val Leu Gly Val Glu Lys
            35                  40                  45

Lys Ser Thr Pro Lys Leu Gln Asp Ser Arg Ser Val Arg Lys Ile Ala
        50                  55                  60

Ser Leu Asp Thr His Ile Ala Leu Ala Cys Ala Gly Leu Lys Ala Asp
65                  70                  75                  80

Ala Arg Val Leu Ile Asn Arg Ala Arg Val Glu Cys Gln Ser His Arg
                85                  90                  95

Leu Thr Val Glu Asp Pro Val Thr Val Glu Tyr Ile Thr Arg Tyr Ile
                100                 105                 110

Ala Gly Leu Gln Gln Lys Tyr Thr Gln Ser Gly Gly Val Arg Pro Phe
            115                 120                 125

Gly Leu Ser Thr Leu Ile Val Gly Phe Asp Pro Tyr Thr Glu Lys Pro
        130                 135                 140

Ala Leu Tyr Gln Thr Asp Pro Ser Gly Thr Phe Ser Ala Trp Lys Ala
145                 150                 155                 160

Asn Ala Thr Gly Arg Asn Ser Asn Ser Met Arg Glu Phe Leu Glu Lys
                165                 170                 175

Asn Tyr Lys Glu Thr Ser Gly Lys Glu Thr Ile Lys Leu Thr Ile Arg
                180                 185                 190

Ala Leu Leu Glu Val Val Glu Ser Gly Gly Lys Asn Ile Glu Ile Ala
```

-continued

```
          195               200               205
Val Met Thr His Lys Asp Gly Leu Arg Gln Leu Glu Glu Glu Ile
    210               215               220

Asp Glu Tyr Val Ala Glu Ile Glu Ala Glu Lys Ala Ala Ala Glu Ala
225               230               235               240

Ala Lys Lys Gly Gly Pro Lys Asp Thr
              245

<210> SEQ ID NO 51
<211> LENGTH: 750
<212> TYPE: DNA
<213> ORGANISM: Triticum aestivum

<400> SEQUENCE: 51
atggcccgct acgaccgagc gatcaccgtc ttctcccccg acggccacct cttccaggtt    60
gagtacgccc tcgaggccgt ccgcaagggc aacgccgccg tcggcgtccg aggcgtcgac   120
accgtcgtcc tcggtgtcga gaagaagtcc accccccaagc tccaggactc caggtccgtg   180
cgcaagatcg cgagcctgga cacccacatc gcgctggcct gcgcgggtct caaggcggac   240
gcgcgcgtgc tgatcaaccg ggcgcgcgtc gagtgccaga gccaccgcct caccgtcgag   300
gaccccgtca ctgtcgagta catcacgcgc tacatcgccg gcctgcagca gaagtacacg   360
cagagcggag gggtgcgccc gttcgggctc tccacgctta tagttggctt cgaccccctat   420 actgagaagc cggcgctgta ccagaccgac ccctccggca ccttctccgc ctggaaggcc   480
aacgccaccg gccgcaactc caactccatg cgcgagttcc ttgagaagaa ttacaaggag   540
acgtccggca aggagaccat caagcttacc atccgagccc tccttgaggt tgtcgagagt   600
ggtggcaaga acattgagat tgctgtgatg acgcacaaag atggtcttcg ccagcttgag   660
gaagaggaga tcgatgagta tgttgctgag attgaagcag agaaggccgc tgctgaggct   720
gcgaagaagg gtggcccgaa agacacataa                                     750

<210> SEQ ID NO 52
<211> LENGTH: 249
<212> TYPE: PRT
<213> ORGANISM: Triticum aestivum

<400> SEQUENCE: 52

Met Ala Arg Tyr Asp Arg Ala Ile Thr Val Phe Ser Pro Asp Gly His
1               5                   10                  15

Leu Phe Gln Val Glu Tyr Ala Leu Glu Ala Val Arg Lys Gly Asn Ala
              20                  25                  30

Ala Val Gly Val Arg Gly Val Asp Thr Val Val Leu Gly Val Glu Lys
          35                  40                  45

Lys Ser Thr Pro Lys Leu Gln Asp Ser Arg Ser Val Arg Lys Ile Ala
      50                  55                  60

Ser Leu Asp Thr His Ile Ala Leu Ala Cys Ala Gly Leu Lys Ala Asp
65                  70                  75                  80

Ala Arg Val Leu Ile Asn Arg Ala Arg Val Glu Cys Gln Ser His Arg
              85                  90                  95

Leu Thr Val Glu Asp Pro Val Thr Val Glu Tyr Ile Thr Arg Tyr Ile
              100                 105                 110

Ala Gly Leu Gln Gln Lys Tyr Thr Gln Ser Gly Gly Val Arg Pro Phe
          115                 120                 125

Gly Leu Ser Thr Leu Ile Val Gly Phe Asp Pro Tyr Thr Glu Lys Pro
          130                 135                 140
```

```
Ala Leu Tyr Gln Thr Asp Pro Ser Gly Thr Phe Ser Ala Trp Lys Ala
145                 150                 155                 160

Asn Ala Thr Gly Arg Asn Ser Asn Ser Met Arg Glu Phe Leu Glu Lys
                165                 170                 175

Asn Tyr Lys Glu Thr Ser Gly Lys Glu Thr Ile Lys Leu Thr Ile Arg
            180                 185                 190

Ala Leu Leu Glu Val Val Glu Ser Gly Gly Lys Asn Ile Glu Ile Ala
        195                 200                 205

Val Met Thr His Lys Asp Gly Leu Arg Gln Leu Glu Glu Glu Glu Ile
    210                 215                 220

Asp Glu Tyr Val Ala Glu Ile Glu Ala Glu Lys Ala Ala Ala Glu Ala
225                 230                 235                 240

Ala Lys Lys Gly Gly Pro Lys Asp Thr
                245
```

STERILE GENES AND RELATED CONSTRUCTS AND APPLICATIONS THEREOF

FIELD

This disclosure relates to the field of plant sexual reproduction, genetics and breeding, and in particular relates to recombinant DNA constructs useful for regulating sterility of plants, and methods for producing sterile plant.

BACKGROUND

Hybrid rice has greatly contribution to the global increase of rice productivity. A cytoplasmic male sterile (CMS) lines-based three-line system and a photoperiod/thermo-sensitive genic male sterile (PTGMS) line-based two lines system are used in commercial hybrid rice production (Chang et al., *Proceedings of the National Academy of Sciences,* 113 (49): 14145-14150 (2016)).

Plant male reproductive development involves a series of events, from stamen meristem specification to pollen grain formation and pollination. Cross-pollination of the fertile transgenic plants to the non-transgenic male sterile plants propagated the male sterile seeds of high purity. Pollen fertility is regulated by day length. For example, rice can be completely sterile when grown under long-day conditions, whereas pollen fertility varies when it is grown under short-day conditions.

The development of female organ mainly refers to the process of ovule development and embryo sac formation. If the female organ development is absent or stagnant, the plant will show female sterility. Ling etc. (1991) divided the female sterility into three categories: 1) defects in pistil development, no style and stigma, and only have a dried ovary; 2) the female organs do not differentiate or staminate; 3) the pistil looks normal, but abnormal in the ovary development. Female sterility is often accompanied by male sterility.

Studies of two distantly related dicotyledons, *Arabidopsis thaliana* and *Antirrhinum majus*, has led to the identification of three classes of homeotic genes, acting alone or in combination to determine floral organ identity (Bowman, et al., *Development,* 112:1 (1991); Carpenter and Coen, *Genes Devl.,* 4:1483 (1990); Schwarz-Sommer, et al., *Science,* 250: 931 (1990)). Several of these genes are transcription factors whose conserved DNA-binding domain has been designated as MADS box (Schwarz-Sommer, et al., supra).

Earlier acting genes that control the identity of flower meristem have also been characterized. Flower meristems are derived from inflorescence meristem in both *Arabidopsis* and *Antirrhinum.* Two factors that control the development of meristematic cells into flowers are known. In *Arabidopsis,* the factors are the products of the LEAFY gene (Weige, et al. Cell 69:843 (1992)) and the *APETALA1* gene (Mandel, et al., Nature 360:273 (1992)). When either of these genes is inactivated by mutation, structures combining the properties of flowers and inflorescence develop (Weigel, et al., supra; Irish and Sussex, Plant Cell, 2:741 (1990)). In *Antirrhinum,* the homologue of the *Arabidopsis* LEAFY gene is FLORI-CAULA (Coen, et al., *Cell,* 63:1311 (1990)) and that of the APETALA1 gene is SQUAMOSA (Huijser, et al., *EMBO J.,* 11:1239 (1992)). The latter pair contains MADS box domains.

Number of male sterile genes have been reported. However, not many reports on the female sterile genes. Recently, great progress has been made in utilization of male sterile genes in developing hybrid seed production technology (Wu et al. Plant Biotechno. J. doi: 10.1111/pbi.12477 (2015)).

Accordingly, there is a need to develop new compositions and methods for altering the sterile characteristics of the target plant. This disclosure provides such compositions and methods.

SUMMARY

In one aspect, the present disclosure includes an isolated polynucleotide regulating plant sterile trait, comprising: (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52; or (c) the full complement of the nucleotide sequence of (a) or (b), wherein increasing expression of the polynucleotide makes the plants sterile.

In certain embodiments, the polynucleotide comprises the nucleotide sequence of SEQ ID NO: 1, SEQ ID NO: 2, SEQ ID NO: 4, SEQ ID NO: 5, SEQ ID NO: 7, SEQ ID NO: 8, SEQ ID NO: 26, SEQ ID NO: 27, SEQ ID NO: 29, SEQ ID NO: 31, SEQ ID NO: 33, SEQ ID NO: 35, SEQ ID NO: 36, SEQ ID NO: 38, SEQ ID NO: 40, SEQ ID NO: 42, SEQ ID NO: 44, SEQ ID NO: 45, SEQ ID NO: 47, SEQ ID NO: 49, or SEQ ID NO: 51.

In certain embodiments, the polynucleotide encodes a polypeptide comprising the amino acid sequence of SEQ ID NO: 3, SEQ ID NO: 6, SEQ ID NO: 9, SEQ ID NO: 28, SEQ ID NO: 30, SEQ ID NO: 32, SEQ ID NO: 34, SEQ ID NO: 37, SEQ ID NO: 39, SEQ ID NO: 41, SEQ ID NO: 43, SEQ ID NO: 46, SEQ ID NO: 48, SEQ ID NO: 50, or SEQ ID NO: 52.

In another aspect, the present disclosure provides the use of the isolated sterile trait-regulating polynucleotide in a plant to regulate the sterile trait, wherein the isolated polynucleotide comprises (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52; or (c) the full complement of the nucleotide sequence of (a) or (b). Certain embodiments provide for the use of the isolated polynucleotide in a plant to make plant sterile by increasing expression of the polynucleotide.

In another aspect, the present disclosure includes a recombinant DNA construct comprising the isolated sterile trait-regulating polynucleotide operably linked to at least one regulatory element, wherein the polynucleotide comprises (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52; or (c) the full complement of the nucleotide sequence of (a) or (b). In certain embodiments, the at least one regulatory element is a promoter functional in a plant. In certain embodiments the at least one regulatory element is heterologous to the polynucleotide.

In another aspect, the present disclosure includes a modified plant, plant cell or seed with increased expression of a polynucleotide encoding a sterility-regulating polypeptide ZOS3-17, Dnak, or PPT1-1, wherein the plant exhibits sterile trait when compared to a control plant planted under the same conditions.

In certain embodiments, the plant, plant cell, or seed is modified to have increased expression of the sterile trait-regulating gene, wherein the plant or plant produced from said plant cell or seed has a sterile trait when compared to a control plant not having said increased expression. In certain embodiments, the modified plant, plant cell, or seed comprises a recombinant DNA construct comprising a sterile trait polynucleotide operably linked to at least one regulatory element, wherein the polynucleotide comprises (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52; or (c) the full complement of the nucleotide sequence of (a) or (b); thereby increasing expression of the polynucleotide in the modified plant, plant cell, or seed. In certain embodiments, the plant comprises a modified regulatory element, wherein the modified regulatory element increases the expression of an endogenous polynucleotide comprising (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52; or (c) the full complement of the nucleotide sequence of (a) or (b).

In certain embodiments, the plant for the use in the compositions and methods provided herein is selected from the group consisting of rice, maize, soybean, sunflower, sorghum, canola, wheat, alfalfa, cotton, barley, millet, sugar cane and switchgrass.

In another aspect, a rice plant is provided, wherein the rice plant comprises a modified genomic locus, wherein expression of an endogenous polynucleotide encoding the polypeptide having an amino acid sequence of at least 90% sequence identity compared to SEQ ID NO: 3, 6 or 9 is increased.

In another aspect, a maize plant is provided, wherein the maize plant comprises a modified genomic locus, wherein expression of an endogenous polynucleotide encoding the polypeptide having an amino acid sequence of at least 90% sequence identity compared to SEQ ID NO: 28, 37, or 46 is increased.

In another aspect, a wheat plant is provided, wherein the wheat plant comprises a modified genomic locus, wherein expression of an endogenous polynucleotide encoding the polypeptide having an amino acid sequence of at least 90% sequence identity compared to SEQ ID NO: 30, 32, 34, 39, 41, 43, 48, 50 or 52 is increased.

In another aspect, methods are provided for regulating plant sterile trait, comprising increasing the expression or function of a polynucleotide encoding a ZOS3-17, DnaK, or PPT1-1 polypeptide in a plant (e.g., rice, maize, or wheat) to make the plant sterile, wherein the polynucleotide comprises: (a) a polynucleotide with a nucleotide sequence of at least 85% identity to SEQ ID NO: 1, 2, 4, 5, 7, 8, 26, 27, 29, 31, 33, 35, 36, 38, 40, 42, 44, 45, 47, 49 or 51; and (b) a polynucleotide encoding a polypeptide with an amino acid sequence of at least 90% identity to SEQ ID NO: 3, 6, 9, 28, 30, 32, 34, 37, 39, 41, 43, 46, 48, 50 or 52.

In another aspect, a method of identifying one or more alleles associated with sterile trait in a population of plants (e.g., rice, maize, wheat) is provided, wherein the method comprises the steps of: (a) detecting in a population of plants one or more polymorphisms in (i) a genomic region encoding a polypeptide or (ii) a regulatory region controlling expression of the polypeptide, wherein the polypeptide comprises the amino acid sequence selected from the group consisting of SEQ ID NO: 3, 6, 9, 28, 30, 32, 34, 37, 39, 41, 43, 46, 48, 50 or 52 or a sequence that is 90% identical to SEQ ID NO: 3, 6, 9, 28, 30, 32, 34, 37, 39, 41, 43, 46, 48, 50 or 52, wherein the one or more polymorphisms in the genomic region encoding the polypeptide or in the regulatory region controlling expression of the polypeptide is associated with sterile trait; and (b) identifying one or more alleles at the one or more polymorphisms that are associated with sterile trait. Wherein the one or more alleles associated with sterile trait is used for marker assisted selection of a plant with sterile trait.

BRIEF DESCRIPTION OF THE DRAWINGS AND SEQUENCE LISTINGS

The disclosure can be more fully understood from the following detailed description and the accompanying Drawings and Sequence Listing which form a part of this application.

FIG. 1 shows the relative expression levels of OsZOS3-17 gene in leaves of different transgenic rice lines (DP0640) by real-time PCR analyses. The base expression level in ZH11-TC is set at 1.00, the numbers on the top of the columns are fold-change compared to ZH11-TC rice.

FIG. 2 shows the relative expression levels of OsDnak gene in leaves of different transgenic rice lines (DP1673) by real-time PCR analyses. The base expression level in ZH11-TC is set at 1.00, the numbers on the top of the columns are fold-change compared to ZH11-TC rice.

FIG. 3 shows the relative expression levels of OsPPT1-1 gene in leaves of different transgenic rice lines (DP1675) by real-time PCR analyses. The base expression level in ZH11-TC is set at 1.00, the numbers on the top of the columns are fold-change compared to ZH11-TC rice.

FIG. 4 shows the pollen staining results of DP0640 transgenic rice plant. The pollens from DP0640 plants were fertile as showed by the $I_2$K-staining.

FIG. 5 shows the seed morphology of DP0640 transgenic rice plant.

FIG. 6 shows the PCR amplification result of F1 hybrid plants of DP0640 transgenic cross-out rice plants.

FIG. 7 shows the pollen staining results of DP1673 transgenic rice plant. The pollens from DP1673 plants were fertile as showed by the $I_2$K-staining.

FIG. 8 shows the pistil development of DP1673 plants. DP1673 plants apparently grew normally before pollination, however, their ovary and stigmas withered and died after pollination.

FIG. 9 shows the pollen staining results of DP1675 transgenic rice plant. The pollens from DP1675 plants were fertile as showed by the $I_2$K-staining.

FIG. 10 shows the PCR amplification result of F1 hybrid plants of DP1675 transgenic cross-out rice plants.

TABLE 1

SEQ ID NOs for nucleotide and amino acid sequences
provided in the sequence listing

| Source species | Clone Description | SEQ ID NO: (Nucleotide) | SEQ ID NO: (Amino Acid) |
|---|---|---|---|
| Oryza sativa | OsZOS3-17 cDNA | 1 | |
| Oryza sativa | OsZOS3-17 CDS | 2 | |
| Oryza sativa | OsZOS3-17 PRT | | 3 |
| Oryza sativa | OsDnaK cDNA | 4 | |
| Oryza sativa | OsDnaK CDS | 5 | |
| Oryza sativa | OsDnaK PRT | | 6 |
| Oryza sativa | OsPPT1-1 gDNA | 7 | |
| Oryza sativa | OsPPT1-1 CDS | 8 | |
| Oryza sativa | OsPPT1-1 PRT | | 9 |
| Artificial | Primers | 10-25 | n/a |
| Zea mays | ZOS3-17 gDNA | 26 | |
| Zea mays | ZOS3-17 CDS | 27 | |
| Zea mays | ZOS3-17 PRT | | 28 |
| Triticum aestivum | ZOS3-17 from A genome CDS | 29 | |
| Triticum aestivum | ZOS3-17 from A genome PRT | | 30 |
| Triticum aestivum | ZOS3-17 from B genome CDS | 31 | |
| Triticum aestivum | ZOS3-17 from B genome PRT | | 32 |
| Triticum aestivum | ZOS3-17 from D genome CDS | 33 | |
| Triticum aestivum | ZOS3-17 from D genome PRT | | 34 |
| Zea mays | DnaK gDNA | 35 | |
| Zea mays | DnaK CDS | 36 | |
| Zea mays | DnaK PRT | | 37 |
| Triticum aestivum | DnaK from A genome CDS | 38 | |
| Triticum aestivum | DnaK from A genome PRT | | 39 |
| Triticum aestivum | DnaK from B genome CDS | 40 | |
| Triticum aestivum | DnaK from B genome PRT | | 41 |
| Triticum aestivum | DnaK from D genome CDS | 42 | |
| Triticum aestivum | DnaK from D genome PRT | | 43 |
| Zea mays | PPT1-1 gDNA | 44 | |
| Zea mays | PPT1-1 CDS | 45 | |
| Zea mays | PPT1-1 PRT | | 46 |
| Triticum aestivum | PPT1-1 from A genome CDS | 47 | |
| Triticum aestivum | PPT1-1 from A genome PRT | | 48 |
| Triticum aestivum | PPT1-1 from B genome CDS | 49 | |
| Triticum aestivum | PPT1-1 from B genome PRT | | 50 |
| Triticum aestivum | PPT1-1 from D genome CDS | 51 | |
| Triticum aestivum | PPT1-1 from D genome PRT | | 52 |

The Drawing Descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (2): 345-373 (1984) which are herein incorporated by reference. The symbols and format used for nucleotide and amino acid sequence data comply with the rules set forth in 37 C.F.R. § 1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

"OsZOS3-17" refers to a rice polypeptide that confers a sterile phenotype when expression is altered. The OsZOS3-17 polypeptide (SEQ ID NO: 3) is encoded by the coding sequence (CDS) (SEQ ID NO: 2) or nucleotide sequence (SEQ ID NO: 1) at rice gene locus LOC_Os03g50850.1 which is annotated as "ZOS3-17-C2H2 zinc finger protein, expressed" in TIGR. "ZOS3-17 polypeptide" refers herein to the OsZOS3-17 polypeptide and its paralogs or homologs from other organisms, such as maize (e.g., SEQ ID NO: 28 encoded by SEQ ID NO: 27 or SEQ ID NO: 26) or wheat (e.g., SEQ ID NO: 30 encoded by SEQ ID NO: 29; SEQ ID NO: 32 encoded by SEQ ID NO: 31; SEQ ID NO: 34 encoded by SEQ ID NO: 33).

"OsDnak" refers to a rice polypeptide that confers a sterile phenotype when expression is altered. The OsDnak polypeptide (SEQ ID NO: 6) is encoded by the coding sequence (CDS) (SEQ ID NO: 5) or nucleotide sequence (SEQ ID NO: 4) at rice gene locus LOC_Os03g16920.1 which is annotated as "Dnak family protein, putative, expressed" in TIGR. "Dnak polypeptide" refers herein to the OsDnak polypeptide and its paralogs or homologs from other organisms, such as maize (e.g., SEQ ID NO: 37 encoded by SEQ ID NO: 36 or SEQ ID NO: 35) or wheat (e.g., SEQ ID NO: 39 encoded by SEQ ID NO: 38; SEQ ID NO: 41 encoded by SEQ ID NO: 40; SEQ ID NO: 43 encoded by SEQ ID NO: 42).

"OsPPT1-1" refers to a rice polypeptide that confers a sterile phenotype when expression is altered. The OsPPT1-1 polypeptide (SEQ ID NO: 9) is encoded by the coding sequence (CDS) (SEQ ID NO: 8) or nucleotide sequence (SEQ ID NO: 7) at rice gene locus LOC_Os08g43540.1 which is annotated as "peptidase, T1 family, putative, expressed" in TIGR. "PPT1-1 polypeptide" refers herein to the OsPPT1-1 polypeptide and its paralogs or homologs from other organisms, such as maize (e.g., SEQ ID NO: 46 encoded by SEQ ID NO: 45 or SEQ ID NO: 44) or wheat (e.g., SEQ ID NO: 48 encoded by SEQ ID NO: 47; SEQ ID NO: 50 encoded by SEQ ID NO: 49; SEQ ID NO: 52 encoded by SEQ ID NO: 51).

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

As used herein, the term "wheat" refers to any species of the genus Triticum, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes T. aestivum, T. spelta, T. mocha, T. compactum, T. sphaerococcum, T. vavilovii, and interspecies cross thereof. Tetraploid wheat includes T. durum (also referred to as

*durum* wheat or *Triticum turgidum* ssp. *durum*), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-*Triticum* species, such as rye (*Secale cereale*), including but not limited to Triticale. In some embodiments, the wheat plant is suitable for commercial production of grain, such as commercial varieties of hexaploid wheat or *durum* wheat, having suitable agronomic characteristics which are known to those skilled in the art.

The terms "sterile" and "sterility" refers to the plants cannot produce seeds. Include but not limited to, the pollen fertility rate or seed setting rate less than 20%, the female organ development is absent or stagnant. The said female organ include but not limited to ovule, pistil, style, stigma etc.

The terms "semi-sterile" and "semi-sterility" refers to the plants cannot produce seeds and/or pollen properly. Include but not limited to, the pollen fertility rate or seed setting rate less than 80%, more than 20%.

The terms "fertile" and "fertility" refers to the plants can produce seeds normally. Include but not limited to, the pollen fertility rate or seed setting rate more than 80%, and the said seeds can germinate and grow normally.

The terms "male sterile" refers to the plants cannot produce pollen or cannot produce enough pollen, which is influenced by the plant reproductive development, such as from stamen meristem specification to pollen grain formation and pollination.

The terms "female sterile" refers to the plants cannot produce seeds because of the abnormal development of female organ. The said abnormal development of female organ, includes but not limited to, the process of ovule development and embryo sac formation.

The terms "full complement" and "full-length complement" are used interchangeably herein and refer to a complement of a given nucleotide sequence, wherein the complement and the nucleotide sequence consist of the same number of nucleotides and are 100% complementary.

The term "trait" refers to a physiological, morphological, biochemical, or physical characteristic of a plant or particular plant material or cell.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a recombinant DNA construct.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-WT, ZH11-TC, WT and empty vector plants may be designated as control plants. ZH11-WT represents wild type Zhonghua 11, ZH11-TC represents rice plants generated from tissue cultured Zhonghua 11, WT represents the wild type plants, such as Zhonghua 11, Daohuaxiang 2, and empty vector represents plants transformed with empty vector DP0158.

"Genome" as it applies to plant cells encompasses not only chromosomal DNA found within the nucleus, but organelle DNA found within subcellular components (e.g., mitochondrial, plastid) of the cell.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

The term "gene" refers to a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. A mutated or modified plant is a plant comprising a mutated gene.

A "targeted mutation" is a mutation in a native gene that was made by altering a target sequence within the native gene using a method involving a double-strand-break-inducing agent that is capable of inducing a double-strand break in the DNA of the target sequence as disclosed herein of known in the art.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Heterologous" with respect to sequence means a sequence that originates from a foreign species, or, if from the same species, is substantially modified from its native form in composition and/or genomic position by deliberate human intervention.

"Polynucleotide", "nucleic acid sequence", "nucleotide sequence", or "nucleic acid fragment" are used interchangeably and is a polymer of RNA or DNA that is single-or double-stranded, optionally containing synthetic, non-natural or altered nucleotide bases.

The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified but does not encompass the alteration of the cell or vector by naturally occurring events (e.g., spontaneous mutation, natural transformation/transduction/transposition) such as those occurring without deliberate human intervention.

"Non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a cDNA. In some embodiments, the non-genomic nucleic acid molecule is a synthetic nucleic acid sequence.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source but arranged in a manner different than that normally found in nature.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Genetic modification" refers to a change or alteration in the genomic nucleic acid sequence of a plant introduced by deliberate human activity.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Transient transformation" refers to the introduction of a nucleic acid fragment into the nucleus, or DNA-containing organelle, of a host organism resulting in gene expression without genetically stable inheritance.

"Stable transformation" refers to the introduction of a nucleic acid fragment into a genome of a host organism resulting in genetically stable inheritance.

A "nuclear localization signal" is a signal peptide which directs the protein to the nucleus (Raikhel. (1992) *Plant Phys.* 100:1627-1632).

A "suppression DNA construct" is a recombinant DNA construct which when transformed or stably integrated into the genome of the plant, results in "silencing" of a target gene in the plant. The target gene may be endogenous or transgenic to the plant. "Silencing", as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product.

"Cosuppression" refers to the production of sense RNA transcripts capable of suppressing the expression of the target gene or gene product. "Sense" RNA refers to RNA transcript that includes the mRNA and can be translated into protein within a cell or in vitro.

Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants.

MicroRNAs (miRNAs) are designed that regulate target genes (e.g., the polynucleotide sequences disclosed herein) by binding to complementary sequences located in the transcripts produced by these genes for example by translational inhibition and RNA cleavage.

"CRISPR-associated genes" refers to nucleic acid sequences that encode polypeptide components of clustered regularly interspersed short palindromic repeats (CRISPR)-associated systems (Cas), and the genes are generally coupled, associated or close to or in the vicinity of flanking CRISPR loci. The terms "Cas gene", "CRISPR-associated gene" are used interchangeably herein. Examples include, but are not limited to, Cas3 and Cas9, which encode endonucleases from the CRISPR type I and type II systems, respectively.

"Cas endonuclease" refers to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell.

"Guide RNA (gRNA)" refers to a crRNA (CRISPR RNA): tracrRNA fused hybrid RNA molecule encoded by a customizable DNA element that, generally, comprises a copy of a spacer sequence which is complementary to the protospacer sequence of the genomic target site, and a binding domain for an associated-Cas endonuclease of the CRISPR complex.

"Guide polynucleotide" refers to a polynucleotide sequence that can form a complex with a Cas endonuclease and enables the Cas endonuclease to recognize and optionally cleave a DNA target site. The guide polynucleotide can be comprised of a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "guide polynucleotide/Cas endonuclease system" refers to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

"Genomic target site" refers to a protospacer and a protospacer adjacent motif (PAM) located in a host genome selected for targeted mutation and/or double-strand break.

"Protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

"Protospacer adjacent motif (PAM)" includes a 3 to 8 bp sequence immediately adjacent to the protospacer sequence in the genomic target site.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 bp by depending on the CRISPR locus (WO2007/025097 published Mar. 1, 2007).

Endonucleases are enzymes that cleave the phosphodiester bond within a polynucleotide chain and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application WO-PCT PCT/US12/30061 filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, Foki. The unique, modular TAL effector DNA binding domain allows for the design of proteins with potentially any given DNA recognition specificity (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type I is endonuclease such as Fokl. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Turning now to the embodiments:

Embodiments include isolated polynucleotides and polypeptides, recombinant DNA constructs (including suppression constructs) useful for regulating plant sterile trait, compositions (such as plants or seeds) comprising these recombinant DNA constructs, and methods utilizing these recombinant DNA constructs, compositions comprising sterile-regulating gene and its promoter.

Isolated Polynucleotides and Polypeptides

The present disclosure includes the following isolated polynucleotides and polypeptides:

In some embodiments, isolated polynucleotides are provided comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 3, 6, 9, 28, 30, 32, 34, 37, 39, 41, 43, 46, 48, 50, or 52; or (ii) a full complement of the nucleic acid sequence of (i), wherein the full complement and the nucleic acid sequence of (i) consist of the same number of nucleotides and are 100% complementary. In certain embodiments, increasing expression of this polynucleotide makes the plant sterile. Any of the foregoing isolated polynucleotides may be utilized in any recombinant DNA constructs of the present disclosure.

In some embodiments, isolated polypeptides are provided having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 3, 6, 9, 28, 30, 32, 34, 37, 39, 41, 43, 46, 48, 50, or 52.

In some embodiments, isolated polynucleotides are provided comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 1, 2, 4, 5, 7, 8, 26, 27, 29, 31, 33, 35, 36, 38, 40, 42, 44, 45, 47, 49 or 51; or (ii) a full complement of the nucleic acid sequence of (i). Any of the foregoing isolated polynucleotides may be utilized in any recombinant DNA constructs of the present disclosure. In certain embodiments, increasing expression of this polynucleotide makes plant sterile.

Recombinant DNA Constructs

In one aspect, the present disclosure includes recombinant DNA constructs.

In one embodiment, the recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 3, 6, 9, 28, 30, 32, 34, 37, 39, 41, 43, 46, 48, 50, or 52; or (ii) a full complement of the nucleic acid sequence of (i).

In another embodiment, the recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity as compared to SEQ ID NO: 1, 2, 4, 5, 7, 8, 26, 27, 29, 31, 33, 35, 36, 38, 40, 42, 44, 45, 47, 49 or 51; or (ii) a full complement of the nucleic acid sequence of (i).

In another embodiment, the recombinant DNA construct comprises a polynucleotide operably linked to at least one regulatory sequence (e.g., a promoter functional in a plant), wherein said polynucleotide encodes a OsZOS3-17, DnaK or a PPT1-1 protein. These polypeptides regulate sterile trait, and may be from, for example, *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella.*

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Regulatory Elements:

A recombinant DNA construct (including a suppression DNA construct) of the present disclosure may comprise at least one regulatory element.

A regulatory element may be a promoter, enhancer, 5'UTR, or 3'UTR.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to regulate plant flowering time. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter which causes the desired temporal and spatial expression may be used in the methods of the present disclosure.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development, the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter Itp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOT-MET2 promoter (WO 2005/063998, published Jul. 14, 2005), the CR1BIO promoter (WO 2006/055487, published May 26, 2006), the CRWAQ81 promoter (WO 2005/035770, published Apr. 21, 2005) and the maize ZRP2.47 promoter (NCBI Accession No. U38790; NCBI GI No. 1063664).

Recombinant DNA constructs of the present disclosure may also include other regulatory elements including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

An enhancer or enhancer element refers to a cis-acting transcriptional regulatory element, a.k.a. cis-element, which confers an aspect of the overall expression pattern, but is usually insufficient alone to drive transcription, of an operably linked polynucleotide sequence. An isolated enhancer element may be fused to a promoter to produce a chimeric promoter cis-element, which confers an aspect of the overall modulation of gene expression. Enhancers are known in the art and include the SV40 enhancer region, the CaMV 35S enhancer element, and the like. Some enhancers are also known to alter normal regulatory element expression patterns, for example, by causing a regulatory element to be expressed constitutively when without the enhancer, the same regulatory element is expressed only in one specific tissue or a few specific tissues. Duplicating the upstream region of the CaMV35S promoter has been shown to increase expression by approximately tenfold (Kay, R. et al., (1987) Science 236:1299-1302).

Compositions:

Provided are plants comprising in their genome any of the recombinant DNA constructs of the present disclosure (such as any of the constructs discussed above). In certain embodiments, the recombinant DNA constructs comprise heterologous regulatory elements. Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic or used in a breeding program to produce hybrid seed, which can be grown to produce plants that would exhibit such an altered agronomic characteristic. The seeds may be maize seeds, wheat seeds, or rice seeds.

The plant of the compositions described herein may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A transgenic plant (for example, a rice, maize, wheat or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 3, 6, 9, 28, 30, 32, 34, 37, 39, 41, 43, 46, 48, 50 or 52; and wherein the plant exhibits sterile trait.

2. The plant of embodiment 1, wherein the polynucleotide encodes ZOS3-17, Dnak or PPT1-1 polypeptide, for example from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon*(brownbeard or red rice), *Oryza nivara* (Indian wild rice), *Arabidopsis thaliana,*

*Cicer arietinum, Solanum tuberosum, Brassica oleracea, Zea mays, Glycine max, Glycine tabacina, Glycine soja* or *Glycine tomentella,* or wheat.

3. Any progeny of the above plants in embodiments 1 to 2, any seeds of the above plants in embodiments 1 to 2, any seeds of progeny of the above plants in embodiments 1 to 2, and cells from any of the above plants in embodiments 1 to 2 and progeny thereof.

In any of the foregoing embodiments 1 to 3 or any other embodiments of the present disclosure, the recombinant DNA construct may comprise at least one heterologous promoter functional in a plant as a regulatory element.

The examples below describe some representative protocols and techniques for regulating plant sterile trait and observing and/or evaluating plants agricultural characteristics under such conditions.

1. Progeny of a transformed plant which is hemizygous with respect to a recombinant DNA construct, such that the progeny is segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% identity of nuclear genetic material compared to the plant comprising the recombinant DNA construct.

Methods

Methods are provided for genome modification of a target sequence in the genome of a plant or plant cell, for selecting plants, for gene editing, and for inserting a polynucleotide of interest into the genome of a plant. The methods employ a guide RNA/Cas endonuclease system, wherein the Cas endonuclease is guided by the guide RNA to recognize and optionally introduce a double strand break at a specific target site into the genome of a cell. The guide RNA/Cas endonuclease system provides for an effective system for modifying target sites within the genome of a plant, plant cell or seed. Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest.

In one embodiment, a method for modifying a target site in the genome of a plant cell, comprises introducing a guide RNA and a Cas endonuclease into said plant, wherein said guide RNA and Cas endonuclease are capable of forming a complex that enables the Cas endonuclease to introduce a double strand break at said target site.

Further provided is a method for modifying a target site in the genome of a plant cell, the method comprising: a) introducing into a plant cell a guide RNA and a Cas endonuclease, wherein said guide RNA and Cas endonuclease are capable of forming a complex that enables the Cas endonuclease to introduce a double strand break at said target site; and, b) identifying at least one plant cell that has a modification at said target site, wherein the modification includes at least one deletion, insertion or substitution of one or more nucleotides in said target site.

Proteins may be altered in various ways including amino acid substitution, deletions, truncations, and insertions. Methods for such manipulations are generally known. For example, amino acid sequence variants of the protein(s) can be prepared by mutations in the DNA. Methods for muta-genesis and nucleotide sequence alterations include, for example, Kunkel, (1985) Proc. Natl. Acad. Sci. USA 82:488-92; Kunkel et al., (1987) and the references cited therein. Guidance regarding amino acid substitutions not likely to affect biological activity of the protein is found, for example, in the model of Dayhoff et al., (1978) Atlas of Protein Sequence and Structure (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

Also provided is a method for editing a nucleotide sequence in the genome of a cell, the method comprising introducing a guide polynucleotide, a Cas endonuclease, and optionally a polynucleotide modification template, into a cell, wherein said guide RNA and Cas endonuclease are capable of forming a complex that enables the Cas endonuclease to introduce a double strand break at target site in the genome at said cell, wherein said polynucleotide modification template comprises at least one nucleotide modification of said nucleotide sequence. The nucleotide sequence in the genome of a cell is selected from the group consisting of a promoter sequence, a terminator sequence, a regulatory element sequence, a splice site, a coding sequence, a polyubiquitination site, an intron site and an intron enhancing motif.

Further provided is a method for editing a promoter sequence in the genome of a cell, the methods comprising introducing a guide polynucleotide, a polynucleotide modification template and at least one Cas endonuclease into a cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said nucleotide sequence.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method for producing a modified plant comprising transforming a plant cell with any of the CRISPR-Cas construct of the present disclosure and regenerating a modified plant from the transformed plant cell, wherein, the modified plant and the modified seed obtained by this method may be used in other methods of the present disclosure.

A method for altering the expression level of a polypeptide of the disclosure in a plant comprising: (a) transforming a regenerable plant cell with a CRISPR-Cas construct of the present disclosure; and (b) regenerating a modified plant from the regenerable plant cell after step (a), wherein the plant gene were edited; and (c) growing the transformed plant, wherein the expression of the CRISPR-Cas construct results in production of altered levels of the polypeptide of the disclosure in the transformed plant.

A method of producing seed comprising any of the preceding methods, and further comprising obtaining seeds from said progeny plant, wherein said seeds comprise in their genome said recombinant DNA construct.

One embodiment provides a method for making sterile plant (e.g., rice), the method comprising increasing the expression of a polynucleotide encoding a polypeptide having at least 90% sequence identity to SEQ ID NO: 3, 6, or 9. The increase in expression of the polynucleotide may be mediated by any of the methods described herein using any of the polynucleotides or compositions described herein.

In some embodiments, the disclosure provides seeds that comprise in their genome the recombinant DNA construct of the disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

The development or regeneration of plants containing the foreign, exogenous isolated nucleic acid fragment that encodes a protein of interest is well known in the art. The regenerated plants are self-pollinated to provide homozygous transgenic plants.

Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

Stacking of Traits

Modified plants may comprise a stack of one or more sterile polynucleotides disclosed herein with one or more additional polynucleotides resulting in the production or suppression of multiple polypeptide sequences. Modified plants comprising stacks of polynucleotide sequences can be obtained by either or both of traditional breeding methods or through genetic engineering methods. These methods include, but are not limited to, breeding individual lines each comprising a polynucleotide of interest, genome editing, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Expression of the sequences can be driven by the same promoter or by different promoters. In certain cases, it may be desirable to introduce a transformation cassette that will suppress the expression of the polynucleotide of interest. This may be combined with any combination of other suppression cassettes or over-expression cassettes to generate the desired combination of traits in the plant. It is further recognized that polynucleotide sequences can be stacked at a desired genomic location using a site-specific recombination system.

EXAMPLES

Example 1

Sterile Genes Cloning and Over-Expression Vectors Construction

A binary construct that contains four multimerized enhancers elements derived from the Cauliflower Mosaic Virus 35S (CaMV 35S) promoter was used, and the rice activation tagging population was developed from four japonica (*Oryza sativa* ssp. *Japonica*) varieties (Zhonghua 11, Chaoyou 1, Taizhong 65 and Nipponbare), which were transformed by Agrobacteria-mediated transformation method as described by Lin and Zhang ((2005) *Plant Cell Rep.* 23:540-547). The transgenic lines generated were developed and the transgenic seeds were harvested to form the rice activation tagging population.

Sterile tagging lines (ATLs) were confirmed in repeated field experiments and their T-DNA insertion loci were determined. The genes near by the left border and right border of the T-DNA were cloned and the functional genes were recapitulated by field screens. Only the recapitulated functional genes are showed herein. And based on LOC IDs of these genes shown in Table 2. Primers were designed for cloning rice sterile genes OsZOS3-17, OsDnaK and OsPPT1-1.

TABLE 2

| Rice gene names, Gene IDs (from TIGR) and Construct IDs | | |
|---|---|---|
| Gene name | LOC ID | Construct ID |
| OsZOS3-17 | LOC_Os03g50850 | DP0640 |
| OsDnaK | LOC_Os03g16920 | DP1673 |
| OsPPT1-1 | LOC_Os08g43540 | DP1675 |

PCR amplified products were extracted after the agarose gel electrophoresis using a column kit and then ligated with TA cloning vectors. The sequences and orientation in these constructs were confirmed by sequencing. Each gene was cloned into a plant binary construct.

Example 2

Generation of Rice Plants with Increased Gene Expression

The over-expression vectors and empty vector (DP0158) were transformed into Zhonghua 11 (*Oryza sativa* L.) by Agrobacteria-mediated as described by Lin and Zhang (*Plant Cell Rep.* 23:540-547 (2005)). The transgenic seedlings (T0) generated in transformation laboratory were transplanted in the field to get T1 seeds. The T1 and T2 seeds were stored at 4° C. The over-expression vectors contain DsRED and HYG genes. T1 and T2 seeds which showed red color under green fluorescent light were transgenic seeds and were used in the following sterility assays.

Gene Expression Analysis in Transgenic Rice Plants:

Gene expression levels in the transgenic rice plants were analyzed by a standard real-time RT-PCR procedure. EF1a gene was used as an internal control to show that the amplification and loading of samples from the transgenic rice and control plant were similar. The expression level was normalized based on the EF1a mRNA levels.

OsZOS3-17 gene expression levels in the DP0640 transgenic rice plants were detected using the primers of SEQ ID NOs: 16 and 17. mRNA was extracted from leaf of T1 or T2 generation seedlings. As shown in FIG. 1, the expression level in ZH11-TC rice is set at 1.00, and OsZOS3-17 gene is over-expressed in almost all the tested transgenic lines.

```
DP0640-F1
                                      (SEQ ID NO: 16)
   5'-AGGCAAAAGAACTCTGGGAG-3'

DP0640-R1
                                      (SEQ ID NO: 17)
   5'-CTGCAGATCAGTGTAGGTCTTC-3'
```

OsDnak gene expression levels in the DP1673 transgenic rice plants were detected using the primers of SEQ ID NOs: 18 and 19. mRNA was extracted from leaf of T1 generation seedlings. As shown in FIG. 2, the expression level in ZH11-TC rice is set at 1.00, and OsDnak gene is over-expressed in almost all the tested transgenic lines.

```
DP1673-F1
                                      (SEQ ID NO: 18)
   ATCGAGGATGCCATCAAGTG

DP1673-R1
                                      (SEQ ID NO: 19)
   CGCCCTGGTACATCTTTGAG
```

OsPPT1-1 gene expression levels in the DP1675 transgenic rice plants were detected using the primers of SEQ ID NOs: 20 and 21. mRNA was extracted from leaf of T1 generation seedlings. As shown in FIG. 3, the expression level in ZH11-TC rice is set at 1.00, and OsPPT1-1 gene is over-expressed in almost all the tested transgenic lines.

```
DP1675-F1
                                  (SEQ ID NO: 20)
5'-GTGGCAAGAACATCGAGATTG-3'

DP1675-R1
                                  (SEQ ID NO: 21)
5'-TTCAATCTCAGCCACGTACTC-3'
```

Example 3

Sterile Trait of OsZOS3-17 Over-Expression Rice Plants

The sterility phenotype was observed during propagation. The fertility was divided into three levels according to pollen fertility rate and seed setting rate as shown in Table 3. The pollen is classified into four types by pollen microscope examination and reaction to 12-KI solution as shown in Table 4.

TABLE 3

Classification of plant fertility by pollen
fertility and seed setting rate

| Parameter | Classification | | |
| --- | --- | --- | --- |
| | Sterility | Semi-sterility | Fertility |
| Pollen fertility (%) | <20 | 20-80 | >80 |
| Seed setting rate (%) | <20 | 20-80 | >80 |

TABLE 4

Pollen classification by pollen microscope examination
and reaction to $I_2$-KI solution

| Character | Type | | | |
| --- | --- | --- | --- | --- |
| | Typical abortion type | Spherical abortion type | Stained abortion type | Fertility |
| Stage | Monokaryotic phase | Dikaryophase | Trinucleate stage | |
| Pollen particle shape | Anomaly | Round | Round | Round and full |
| Dyeing condition ($I_2$-KI) | Non-staining | Non-staining | Partial and light staining | Deep and even staining |

The OsZOS3-17 transgenic rice plants were planted in Beijing (40° 13'N) to get seeds. The results were as below.

1. Sterile Trait at T1 Generation

The seed setting rates of OsZOS3-17 transgenic rice lines at T1 generation are listed in Table 5. Four of thirteen lines (DP0640.05, DP0640.06, DP0640.07, DP0640.13) were fertile. In the other nine lines, there are fertile plants and sterile plants. The ratio of fertile plants to sterile plants in all lines was about 3:1, indicating a potential recessive sterile gene.

TABLE 5

Seed setting of DP0640 at T1 generation in Beijing (1$^{st}$ experiment)

| Line ID | Total plant number | Seed setting | | |
| --- | --- | --- | --- | --- |
| | | Fertile | Semi-sterile | Sterile |
| DP0640.01 | 10 | 4 | 0 | 6 |
| DP0640.02 | 10 | 8 | 0 | 2 |
| DP0640.03 | 10 | 6 | 0 | 4 |
| DP0640.05 | 10 | 10 | 0 | 0 |
| DP0640.06 | 10 | 10 | 0 | 0 |
| DP0640.07 | 10 | 10 | 0 | 0 |
| DP0640.09 | 10 | 7 | 0 | 3 |
| DP0640.10 | 10 | 6 | 0 | 4 |
| DP0640.12 | 6 | 4 | 0 | 2 |
| DP0640.13 | 10 | 10 | 0 | 0 |
| DP0640.16 | 10 | 4 | 0 | 6 |
| DP0640.17 | 5 | 3 | 1 | 1 |
| DP0640.18 | 3 | 2 | 0 | 1 |
| Totally | 114 | 84 | 1 | 29 |

To confirm the observation, three lines at T1 generation were planted again in Beijing. The pollen from the transgenic rice plants were tested, and the same panicles were bagged to measure the seed setting rate. As shown in table 6, the pollen from all the three lines at T1 generation were fertile. As shown in table 7, the bagged panicles from the three OsZOS3-17 transgenic rice lines were fertile, semi-sterile and sterile; and the ratio of fertile panicles to sterile panicles was 2.4:1. As shown in table 8, the three OsZOS3-17 transgenic rice lines were fertile, semi-sterile and sterile panicles; the ratio of fertile panicles to sterile panicles was about 3:1. These results consistently demonstrate that OsZOS3-17 is likely a recessive sterile gene.

TABLE 6

Pollen fertility of DP0640 at T1 generation
in Beijing (2$^{nd}$ experiment)

| Line ID | Panicle number tested | Pollen fertility | | |
| --- | --- | --- | --- | --- |
| | | Fertility | Semi-sterility | Sterility |
| DP0640.01 | 10 | 10 | 0 | 0 |
| DP0640.02 | 10 | 10 | 0 | 0 |
| DP0640.03 | 9 | 9 | 0 | 0 |
| Totally | 29 | 29 | 0 | 0 |

TABLE 7

Seed setting of bagged panicles of DP0640
at T1 generation in Beijing (2$^{nd}$ experiment)

| Line ID | Bagged panicle number | Seed setting | | |
| --- | --- | --- | --- | --- |
| | | Fertility | Semi-sterility | Sterility |
| DP0640.01 | 8 | 5 | 0 | 3 |
| DP0640.02 | 10 | 8 | 0 | 2 |
| DP0640.03 | 8 | 4 | 2 | 2 |
| Totally | 26 | 17 | 2 | 7 |

TABLE 8

Seed setting of DP0640 at T1 generation
in Beijing (2$^{nd}$ experiment)

| Line ID | Plant number | Seed setting | | |
| | | Fertility | Semi-sterility | Sterility |
| --- | --- | --- | --- | --- |
| DP0640.01 | 15 | 9 | 1 | 5 |
| DP0640.02 | 15 | 11 | 1 | 3 |
| DP0640.03 | 10 | 8 | 0 | 2 |
| Totally | 40 | 28 | 2 | 10 |

2. Sterile Trait at T2 Generation

OsZOS3-17 transgenic rice plants at T2 generation were planted. The pollen from the transgenic rice plants were tested, and the same panicles were bagged to measure the seed setting rate. As shown in table 9, the pollen from all the 13 lines were fertile. As shown in table 10, the bagged panicles from the OsZOS3-17 transgenic rice lines were fertile, semi-sterile and sterile; and the ratio of fertile panicles to sterile panicles was 3.9:1. As shown in table 11, the thirteen OsZOS3-17 transgenic rice lines were fertile, semi-sterile and sterile panicles; the ratio of fertile panicles to sterile panicles was 3.5:1. These results are consistent with the results of T1 generation, and it shows that OsZOS3-17 is likely a recessive sterile gene.

TABLE 9

Pollen fertility of DP0640 at T2 generation in Beijing

| Line ID | Panicle number tested | Pollen fertility | | |
| | | Fertility | Semi-sterility | Sterility |
| --- | --- | --- | --- | --- |
| DP0640.01.01 | 9 | 9 | 0 | 0 |
| DP0640.02.01 | 10 | 10 | 0 | 0 |
| DP0640.03.01 | 9 | 9 | 0 | 0 |
| DP0640.05.01 | 9 | 9 | 0 | 0 |
| DP0640.06.01 | 10 | 10 | 0 | 0 |
| DP0640.07.01 | 10 | 10 | 0 | 0 |
| DP0640.09.01 | 10 | 10 | 0 | 0 |
| DP0640.10.01 | 10 | 10 | 0 | 0 |
| DP0640.12.01 | 9 | 9 | 0 | 0 |
| DP0640.13.01 | 10 | 10 | 0 | 0 |
| DP0640.16.01 | 10 | 10 | 0 | 0 |
| DP0640.17.01 | 10 | 10 | 0 | 0 |
| DP0640.18.01 | 10 | 10 | 0 | 0 |
| Totally | 126 | 126 | 0 | 0 |

TABLE 10

Seed setting of bagged panicles of
DP0640 at T2 generation in Beijing

| Line ID | Bagged panicle number | Seed setting | | |
| | | Fertility | Semi-sterility | Sterility |
| --- | --- | --- | --- | --- |
| DP0640.01.01 | 9 | 5 | 2 | 2 |
| DP0640.02.01 | 10 | 5 | 2 | 3 |
| DP0640.03.01 | 9 | 4 | 3 | 2 |
| DP0640.05.01 | 10 | 5 | 4 | 1 |
| DP0640.06.01 | 10 | 6 | 2 | 2 |
| DP0640.07.01 | 9 | 7 | 0 | 2 |
| DP0640.09.01 | 10 | 6 | 2 | 2 |
| DP0640.10.01 | 10 | 7 | 1 | 2 |
| DP0640.12.01 | 9 | 6 | 1 | 2 |

TABLE 10-continued

Seed setting of bagged panicles of
DP0640 at T2 generation in Beijing

| Line ID | Bagged panicle number | Seed setting | | |
| | | Fertility | Semi-sterility | Sterility |
| --- | --- | --- | --- | --- |
| DP0640.13.01 | 10 | 9 | 1 | 0 |
| DP0640.16.01 | 9 | 5 | 1 | 3 |
| DP0640.17.01 | 9 | 7 | 2 | 0 |
| DP0640.18.01 | 9 | 9 | 0 | 0 |
| Totally | 123 | 81 | 21 | 21 |

TABLE 11

Seed setting of DP0640 at T2 generation in Beijing

| Line ID | Plant number | Seed setting | | |
| | | Fertility | Semi-sterility | Sterility |
| --- | --- | --- | --- | --- |
| DP0640.01.01 | 19 | 14 | 1 | 4 |
| DP0640.02.01 | 20 | 15 | 1 | 4 |
| DP0640.03.01 | 19 | 15 | 0 | 4 |
| DP0640.05.01 | 18 | 12 | 5 | 1 |
| DP0640.06.01 | 20 | 16 | 2 | 2 |
| DP0640.07.01 | 20 | 12 | 0 | 8 |
| DP0640.09.01 | 15 | 9 | 2 | 4 |
| DP0640.10.01 | 20 | 13 | 2 | 5 |
| DP0640.12.01 | 20 | 13 | 1 | 6 |
| DP0640.13.01 | 20 | 20 | 0 | 0 |
| DP0640.16.01 | 20 | 9 | 0 | 11 |
| DP0640.17.01 | 20 | 17 | 2 | 1 |
| DP0640.18.01 | 20 | 16 | 3 | 1 |
| Totally | 251 | 181 | 19 | 51 |

Both pollen and pistil phenotypes were observed in the above experiments. The pollen of OsZOS3-17 transgenic rice plants were fertile (FIG. 4). And no abnormal phenotype in pistils was observed with OsZOS3-17 transgenic rice plants. During the field experiments, except a few individual plants, most of the transgenic rice plants had only a sterile phenotype, and the other phenotypes, include but not limited to, plant height, growth period, yield etc., were normal.

3. OsZOS3-17 Transgenic Rice Seed Phenotype

One line of DP0640.02 at T2 generation and one line of DP0640.12.01 at T3 generation were planted to get seeds. However, most of the seeds were shrunken grain (FIG. 5). The seed germination experiment is needed to validate the sterility phenotype of shrunken grains.

4. Seed Germination Experiment of OsZOS3-17 Transgenic Rice Seeds

One T2 generation line of DP0640.02 and one T3 generation line of DP0640.12.01 were tested 3 times with 50 seeds per replication. ZH11-TC and DP0158 are used as controls. All the seeds were put in oven at 42° C. for 72 h to break seed dormancy. Seeds were placed evenly in a germination box, covered with filter paper and 18 ml water, and put into an incubator at 28° C. for 8 days. The resulting germination rate was then recorded.

As shown in Table 12, the germination rate of the seeds from OsZOS3-17 transgenic rice plants are lower than that of ZH11-TC and DP0158 controls. And the germination rate of the homozygosis seeds is lower than that of the heterozygosis seeds in OsZOS3-17 transgenic rice plants. All the shrunken seeds did not germinate.

TABLE 12

| | | | | | Seed germination rate of DP0640 at T2 and T3 generations |
|---|---|---|---|---|

| Line ID | Genotype | Totally seed number | Germi-nated | Un-germi-nated | Germi-nation rate |
|---|---|---|---|---|---|
| ZH11-TC | | 150 | 147 | 3 | 98% |
| DP0158.mix | | 150 | 142 | 8 | 95% |
| DP0640.02-1 | Heterozygous | 150 | 111 | 39 | 74% |
| DP0640.02-2 | Homozygous | 150 | 8 | 142 | 5% |
| DP0640.12.01-1 | Heterozygous | 150 | 136 | 14 | 91% |
| DP0640.12.01-2 | Homozygous | 150 | 7 | 143 | 5% |

5. Fluorescence Segregation Ratio of OsZOS3-17 Transgenic Rice Seeds

The fluorescence segregation ratio of OsZOS3-17 transgenic rice seeds were measured. The seeds of 28 plants from three lines at T1 generation were detected, and 100 seeds from each plant. The results demonstrated that 2128 of 2800 seeds show red color under green fluorescence light, while 672 of 2800 seeds didn't show red color. The ratio of red color seeds to normal seeds was 3.2:1.

The seeds of 156 plants from 13 lines at T2 generation were inspected also, using 100 seeds from each plant. A total of 15519 seeds were tested. The results demonstrated that 11836 seeds show red color under green fluorescence light, while 3683 seeds didn't show red color. The ratio of red color seeds to normal seeds was 3.2:1. These results indicated that single OsZOS3-17 gene was inserted in the OsZOS3-17 transgenic rice genome.

TABLE 13

| | | | | | Fluorescence segregation ratio of OsZOS3-17 transgenic rice seeds |
|---|---|---|---|---|

| Generation | Total seed number | DsRed-seed number | DsRed-null seed number | Ratio |
|---|---|---|---|---|
| T1 | 2800 | 2128 | 672 | 3.17 |
| T2 | 15519 | 11836 | 3683 | 3.21 |

6. Cross-In and Cross-Out Results of OsZOS3-17 Transgenic Rice

To further investigate the function of OsZOS3-17 gene, cross-in and cross-out experiments were performed, and only the homozygous plants were used in the experiments. As shown in table 14, the cross-in of 560 florets from 10 plants with pollen from wildtype ZH11 did not produce any seed; while the cross-out of 705 florets with wildtype ZH11 seeds to OsZOS3-17 transgenic plants produce seeds, and some seeds show red color under the green florescence light. This data indicate OsZOS3-17 is a potential female sterile gene.

TABLE 14

| | | | | | | Seed set of cross-In and cross-Out of DP0640 transgenic lines |
|---|---|---|---|---|---|

| | | Cross-breeding | | Seed number | | |
|---|---|---|---|---|---|---|
| Line ID | Plant ID | (♀) Cross-In | (♂) Cross-Out | Floret number | Total | DsRed seed | Null seed |
| DP0640.02.1-3 | 1-1 | ✓ | | 51 | 0 | 0 | 0 |
| DP0640.02.1-3 | 1-2 | ✓ | | 83 | 0 | 0 | 0 |
| DP0640.02.1-3 | 2-1 | ✓ | | 51 | 0 | 0 | 0 |
| DP0640.02.1-3 | 1-7 | ✓ | | 49 | 0 | 0 | 0 |
| DP0640.02.1-3 | 1-8 | ✓ | | 48 | 0 | 0 | 0 |
| DP0640.02.2-4 | 1-8 | ✓ | | 51 | 0 | 0 | 0 |
| DP0640.02.2-4 | 2-4 | ✓ | | 54 | 0 | 0 | 0 |
| DP0640.02.2-4 | 1-1 | ✓ | | 54 | 0 | 0 | 0 |
| DP0640.02.2-4 | 1-2 | ✓ | | 55 | 0 | 0 | 0 |
| DP0640.02.2-4 | 1-5 | ✓ | | 64 | 0 | 0 | 0 |
| Totally | | | | 560 | 0 | 0 | 0 |
| DP0640.02.1-3 | 1-3 | | ✓ | 79 | 14 | 13 | 1 |
| DP0640.02.1-3 | 1-5 | | ✓ | 75 | 6 | 0 | 6 |
| DP0640.02.1-3 | 2-3 | | ✓ | 110 | 51 | 34 | 17 |
| DP0640.02.1-3 | 1-2 | | ✓ | 74 | 41 | 19 | 22 |
| DP0640.02.1-3 | 1-3 | | ✓ | 83 | 35 | 32 | 3 |
| DP0640.02.1-3 | 1-4 | | ✓ | 86 | 12 | 4 | 8 |
| DP0640.02.1-3 | 2-8 | | ✓ | 60 | 25 | 15 | 10 |
| DP0640.02.2-4 | 1-1 | | ✓ | 92 | 22 | 8 | 14 |
| DP0640.02.2-4 | 1-8 | | ✓ | 46 | 3 | 0 | 3 |
| Totally | | | | 705 | 209 | 125 | 84 |

The cross-out seeds were validated by PCR with the primers of SEQ ID NO: 22 and SEQ ID NO: 23. The PCR validation results demonstrated that all the cross-out plants contained the OsZOS3-17 gene. The seed setting of the cross-out plants was also measured. As shown in table 15, all the plants were fertile.

TABLE 15

Sees sets of cross-out of DP0640 lines

| | | Total | Seed setting | | |
|---|---|---|---|---|---|
| Line ID | Gener-ation | plant number | Fertility | Semi-sterility | Sterility |
| DP0640.01♂.1-9-F | F1 | 10 | 10 | 0 | 0 |
| DP0640.01.01♂.1-7-F | F1 | 10 | 10 | 0 | 0 |
| DP0640.02.01♂.1-1-F | F1 | 10 | 10 | 0 | 0 |
| DP0640.07.01♂.1-9-F | F1 | 4 | 4 | 0 | 0 |
| DP0640.12.01♂.1-3-F | F1 | 5 | 4 | 1 | 0 |
| DP0640.10.01♂.1-10-F | F1 | 2 | 2 | 0 | 0 |

Example 4

Sterile Trait of OsDnak Over-Expression Rice Plants

The classification of plant fertility and pollen types are illustrated in example 3. The OsDnak transgenic rice plants were planted to get seeds. The results are shown below.

1. Phenotype at T0 Generation

Forty-nine transgenic seedlings (TO, DP1673) generated in the transformation laboratory were transplanted in Hainan field (18° 30'N) to get T1 seeds in October. The rice plants were managed by normal practice using pesticides and fertilizers. The architecture, panicle phenotype of OsDnak transgenic rice plants were same to that of wild-type rice plants during the whole growth period. Finally, some seeds were harvested from 25 lines and no seed was obtained from the remaining 24 lines. This data indicates that the overexpression of OsDnak gene may impact the sterile trait, and OsDnak may be a dominant sterile gene.

2. Sterile Trait at T1 Generation

To further confirm the sterility trait observation at the TO generation, the seeds from the first 15 lines were planted in Beijing field (40° 13'N). The seed setting rates or the pollen fertility of OsDnak transgenic rice plants were measured. The seed setting rates of DP1673 T1 lines are listed in Table 16. Thirteen of fifteen lines showed a complete sterile phenotype and two lines (DP1673.06, DP1673.12) were fertile. This data further indicates overexpression of OsDnak gene may impact the sterile trait.

TABLE 16

Sterile phenotypes of DP1673 at T1 generation in Beijing

| | Total | Seed set | | |
|---|---|---|---|---|
| Line ID | plant number | Fertility | Semi-sterility | Sterility |
| DP1673.01 | 10 | 0 | 0 | 10 |
| DP1673.02 | 10 | 0 | 0 | 10 |
| DP1673.03 | 10 | 0 | 0 | 10 |
| DP1673.04 | 10 | 0 | 0 | 10 |
| DP1673.05 | 5 | 0 | 0 | 5 |
| DP1673.06 | 10 | 8 | 0 | 2 |
| DP1673.07 | 10 | 0 | 0 | 10 |
| DP1673.08 | 10 | 0 | 0 | 10 |
| DP1673.09 | 8 | 0 | 0 | 8 |
| DP1673.10 | 10 | 0 | 0 | 10 |
| DP1673.11 | 10 | 0 | 0 | 10 |
| DP1673.12 | 10 | 10 | 0 | 0 |
| DP1673.13 | 10 | 1 | 0 | 9 |
| DP1673.14 | 10 | 0 | 0 | 10 |
| DP1673.15 | 10 | 0 | 0 | 10 |

To understand if the phenotypes were impacted by locations and/or environmental factors, the stubbles of OsDnak transgenic rice were transferred from Beijing to Hainan in October. As indicated in Table 17, the pollen from almost all the rice plants are fertile or semi-sterile. While the seed sets of 6 lines (DP1673.01, DP1673.02, DP1673.05, DP1673.10, DP1673.14, DP1673.15) remained completely sterile at both Beijing and Hainan; another 6 lines (DP1673.03, DP1673.04, DP1673.07, DP1673.08, DP1673.09, DP1673.11) were sterile in Beijing, but set seeds in Hainan (semi or high sterile); and the rest 3 lines (DP1673.06, DP1673.12, DP1673.13) showed segregating sterile phenotypes at both Beijing and Hainan.

TABLE 17

Sterile phenotypes of DP1673 at T1 generation in Hainan

| | Total | Pollen fertility | | | Seed set | | |
|---|---|---|---|---|---|---|---|
| Line ID | plant number | Fertility | Semi-sterility | Sterility | Fertility | Semi-sterility | Sterility |
| DP1673.01 | 10 | 9 | 1 | 0 | 0 | 0 | 10 |
| DP1673.02 | 9 | 4 | 5 | 0 | 0 | 0 | 9 |
| DP1673.03 | 10 | 3 | 7 | 0 | 0 | 0 | 10 |
| DP1673.04 | 10 | 3 | 7 | 0 | 0 | 1 | 9 |
| DP1673.05 | 6 | 5 | 0 | 1 | 0 | 0 | 6 |
| DP1673.06 | 8 | 8 | 0 | 0 | 6 | 2 | 0 |
| DP1673.07 | 10 | 8 | 2 | 0 | 0 | 1 | 9 |
| DP1673.08 | 9 | 7 | 2 | 0 | 0 | 0 | 9 |
| DP1673.09 | 7 | 5 | 0 | 2 | 0 | 1 | 6 |
| DP1673.10 | 6 | 6 | 0 | 0 | 0 | 0 | 6 |
| DP1673.11 | 5 | 3 | 2 | 0 | 0 | 3 | 2 |
| DP1673.12 | 6 | 3 | 3 | 0 | 0 | 0 | 6 |
| DP1673.13 | 8 | 5 | 3 | 0 | 0 | 1 | 7 |

TABLE 17-continued

| | Total | Pollen fertility | | | Seed set | | |
|---|---|---|---|---|---|---|---|
| Line ID | plant number | Fertility | Semi-sterility | Sterility | Fertility | Semi-sterility | Sterility |
| DP1673.14 | 5 | 3 | 2 | 0 | 0 | 0 | 5 |
| DP1673.15 | 3 | 3 | 0 | 0 | 0 | 0 | 3 |

*Sterile phenotypes of DP1673 at T1 generation in Hainan*

Interestingly, seed sets were different in panicles from same plant in 6 lines (DP1673.03, DP1673.04, DP1673.07, DP1673.08, DP1673.11, DP1673.12). The young tiller-developed panicles showed fertile phenotypes, whereas the primary and older panicles showed sterile phenotypes under both bagged or un-bagged conditions.

The temperature and day-light-length during the panicle development were different between Beijing and Hainan. In Beijing field, the temperature was more than 23° C. and day-light-length was longer than 12 hours; whereas the temperature was less than 23° C. and day-light-length was shorter than 12 hours in Hainan field during the young panicle development. These results indicate that the sterility of DP1673 plants was impacted by temperature and day-light-length.

To understand if the sterile phenotypes of these stubbles were retained as in the first Beijing field planting, the stubbles from Hainan were transferred back to Beijing field. As indicated in Table 18, all the events showed sterile phenotypes except DP1673.06 line as observed in the first planting. These results further confirmed OsDnak is likely a female-sterile gene and the function was impacted by the environmental factors.

TABLE 18

*Sterile phenotypes of DP1673 at T1 generation in Beijing (2$^{nd}$ time)*

| | Total | Seed set | | |
|---|---|---|---|---|
| Line ID | plant number | Fertility | Semi-sterility | Sterility |
| DP1673.01 | 5 | 0 | 0 | 5 |
| DP1673.02 | 5 | 0 | 0 | 5 |
| DP1673.03 | 5 | 0 | 0 | 5 |
| DP1673.04 | 8 | 0 | 0 | 8 |
| DP1673.05 | 3 | 0 | 0 | 3 |
| DP1673.06 | 3 | 2 | 0 | 1 |
| DP1673.07 | 4 | 0 | 0 | 4 |
| DP1673.08 | 6 | 0 | 0 | 6 |
| DP1673.09 | 4 | 0 | 0 | 4 |
| DP1673.10 | 3 | 0 | 0 | 3 |
| DP1673.11 | 2 | 0 | 0 | 2 |
| DP1673.12 | 4 | 0 | 0 | 4 |
| DP1673.13 | 4 | 0 | 0 | 4 |
| DP1673.14 | 3 | 0 | 0 | 3 |

To understand if the transgene expression level in DP1673 plants related to the sterile phenotypes, leaf samples were collected from the stubble plants from the second Beijing field planting, and quantitative RT-PCR analyses was performed. As indicated in FIG. 2, all the events which showed sterile phenotypes have increased OsDnak expression, more than 200-fold, whereas the DP1673.06 line which showed fertility only increased 21-fold. These results indicated that the OsDnak transgene expression level is closely related to the sterility.

3. Sterile Trait at T2 Generation

We planted 3 lines (DP1673.04, DP1673.07 and DP1673.06) of the T2 generation. The seed set results indicate that plants from both DP1673.04 and DP1673.07 were sterile, whereas DP1673.06 plants were fertile. Also, young tillers from both DP1673.04 and DP1673.07 plants, that experienced a lower temperature (<20° C.) along with short-day-light-length (<12 hours) showed fertile phenotypes. These results were consistent with the data from T1 generation. OsDnaK is likely a female-sterile gene and its function is impacted by environmental factors.

4. Cross-In and Cross-Out Results of OsDnaK Transgenic Rice

To further investigate the function of OsDnak gene, cross-in and cross-out experiments were performed in Beijing. As shown in table 19, the cross-in of 502 florets of 7 lines with pollen from wildtype ZH11 produced little, if any seed; the cross-out of 384 of 5 lines to wildtype ZH11 produced seeds, and some seed showed red color under the green florescence light. These data indicate OsDnaK is a potential female sterile gene.

TABLE 19

*Seed sets of Cross-In and Cross-Out of DP1673 lines*

| | Cross-breeding | | Seed number | | |
|---|---|---|---|---|---|
| Line ID | (♀) Cross-In | (♂) Cross-Out | Floret number | Total | DsRed seed | Null seed |
| DP1673.01 | ✓ | | 133 | 0 | 0 | 0 |
| DP1673.07 | ✓ | | 38 | 0 | 0 | 0 |
| DP1673.08 | ✓ | | 82 | 0 | 0 | 0 |
| DP1673.09 | ✓ | | 100 | 0 | 0 | 0 |
| DP1673.11 | ✓ | | 55 | 4 | 0 | 4 |
| DP1673.12 | ✓ | | 33 | 0 | 0 | 0 |
| DP1673.14 | ✓ | | 61 | 0 | 0 | 0 |
| Totally | | | 502 | 4 | 0 | 4 |
| DP1673.01 | | ✓ | 134 | 38 | 24 | 14 |
| DP1673.04 | | ✓ | 91 | 31 | 20 | 11 |
| DP1673.07 | | ✓ | 50 | 23 | 10 | 13 |
| DP1673.09 | | ✓ | 51 | 6 | 4 | 2 |
| DP1673.13 | | ✓ | 58 | 16 | 5 | 11 |
| Totally | | | 384 | 114 | 63 | 51 |

5. Pistil Development of OsDnak Transgenic Plants

To understand the female sterile mechanism of OsDnak, the development process of DP1673.01 plants at T2 generation were carefully observed in Beijing field. The pollen from DP1673 plants were fertile by I$_2$K-statining as shown in FIG. 7. The fertility of pollen from DP1673.01 plants was more than 90%. The pistils of the DP1673.01 plants apparently grew normally before pollination, however, their ovary and stigmas withered and died after pollination as indicated in FIG. 8. These results clearly demonstrated that OsDnaK prevented pistil development after pollination. A similar phenomenon was observed with other lines, such as DP1673.04 and DP1673.07.

Example 5

Sterile Trait of OsPPT1-1 Over-Expression Rice Plants

The classification of plant fertility and pollen types were illustrated in example 3. The OsPPT1-1 transgenic rice plants were planted to get seeds. The results are shown below.

1. Sterile Trait at T1 Generation

Fifteen lines at T1 generation were planted in Beijing field (40° 13'N). The seed setting rates of OsPPT1-1 transgenic rice at T1 generation are listed in Table 20. Seven of fifteen lines (DP1675.02, DP1675.04, DP1675.09, DP1675.10, DP1675.11, DP1675.14, DP1657.15) were complete fertile. While there were fertile plants and sterile plants in other eight lines. The ratio of fertile plants to sterile plants of all transgenic plants is about 21:4, indicating a potential recessive sterile gene.

TABLE 20

Seed setting of DP1675 at T1 generation in Beijing (1st experiment)

| Line ID | Total plant number | Seed setting | |
| --- | --- | --- | --- |
| | | Fertile | Sterile |
| DP1675.01 | 10 | 9 | 1 |
| DP1675.02 | 10 | 10 | 0 |
| DP1675.03 | 10 | 7 | 3 |
| DP1675.04 | 10 | 10 | 0 |
| DP1675.05 | 10 | 6 | 4 |
| DP1675.06 | 10 | 8 | 2 |
| DP1675.07 | 10 | 7 | 3 |
| DP1675.08 | 10 | 5 | 5 |
| DP1675.09 | 10 | 10 | 0 |
| DP1675.10 | 10 | 10 | 0 |
| DP1675.11 | 10 | 10 | 0 |
| DP1675.12 | 10 | 8 | 2 |
| DP1675.13 | 10 | 6 | 4 |
| DP1675.14 | 10 | 10 | 0 |
| DP1675.15 | 10 | 10 | 0 |
| Totally | 150 | 126 | 24 |

To confirm the observation, the fifteen lines at the T1 generation were validated again in the Beijing field. The pollen from the transgenic rice plants was examined using microscopy, and the panicles were bagged to measure the seed setting rate. As shown in table 21, the fertile pollen rate of all the lines at T1 generation were 97%. This indicate the pollen fertility of OsPPT1-1 transgenic plants are normal. As shown in table 22, the bagged panicles from the fifteen OsPPT1-1 transgenic rice plants were fertile, semi-sterile and sterile; and the ratio of fertile panicles to sterile panicles was 3.2:1. Before harvest, the seed setting rate of all individual plant were measured. As shown in table 23, the fifteen OsPPT1-1 transgenic rice lines were fertile, semi-sterile and sterile panicles; the ratio of fertile panicles to sterile panicles was about 3.1:1. These results consistently demonstrate that OsPPT1-1 is likely a recessive sterile gene.

TABLE 21

Pollen fertility of DP1675 at T1 generation in Beijing (2nd experiment)

| Line ID | Bagged panicle number | Seed set | |
| --- | --- | --- | --- |
| | | Fertility | Semi-sterility |
| DP1675.01 | 8 | 8 | 0 |
| DP1675.02 | 10 | 10 | 0 |
| DP1675.03 | 8 | 8 | 0 |
| DP1675.04 | 10 | 10 | 0 |
| DP1675.05 | 8 | 8 | 0 |
| DP1675.06 | 10 | 10 | 0 |
| DP1675.07 | 10 | 10 | 0 |
| DP1675.08 | 9 | 9 | 0 |
| DP1675.09 | 10 | 10 | 0 |
| DP1675.10 | 8 | 8 | 0 |
| DP1675.11 | 10 | 10 | 0 |
| DP1675.12 | 10 | 10 | 0 |
| DP1675.13 | 10 | 6 | 4 |
| DP1675.14 | 10 | 10 | 0 |
| DP1675.15 | 8 | 8 | 0 |
| Totally | 139 | 135 | 4 |

TABLE 22

Seed setting of bagged panicles of DP1675 at T1 generation in Beijing (2nd experiment)

| Line ID | Bagged panicle number | Seed set | | |
| --- | --- | --- | --- | --- |
| | | Fertility | Semi-sterility | Sterility |
| DP1675.01 | 9 | 7 | 0 | 2 |
| DP1675.02 | 10 | 10 | 0 | 0 |
| DP1675.03 | 8 | 5 | 2 | 1 |
| DP1675.04 | 10 | 10 | 0 | 0 |
| DP1675.05 | 7 | 6 | 0 | 1 |
| DP1675.06 | 10 | 7 | 0 | 3 |
| DP1675.07 | 9 | 3 | 0 | 6 |
| DP1675.08 | 10 | 3 | 3 | 4 |
| DP1675.09 | 9 | 8 | 0 | 1 |
| DP1675.10 | 8 | 6 | 0 | 2 |
| DP1675.11 | 10 | 9 | 1 | 0 |
| DP1675.12 | 10 | 5 | 0 | 5 |
| DP1675.13 | 8 | 7 | 0 | 1 |
| DP1675.14 | 10 | 7 | 0 | 3 |
| DP1675.15 | 10 | 7 | 1 | 2 |
| Totally | 138 | 100 | 7 | 31 |

TABLE 23

Seed setting of DP1675 at T1 generation in Beijing (2nd experiment)

| Line ID | Plant number | Seed set | | |
| --- | --- | --- | --- | --- |
| | | Fertility | Semi-sterility | Sterility |
| DP1675.01 | 20 | 14 | 1 | 5 |
| DP1675.02 | 19 | 19 | 0 | 0 |
| DP1675.03 | 20 | 14 | 0 | 6 |
| DP1675.04 | 20 | 20 | 0 | 0 |
| DP1675.05 | 20 | 13 | 0 | 7 |
| DP1675.06 | 16 | 11 | 4 | 1 |
| DP1675.07 | 15 | 6 | 1 | 8 |
| DP1675.08 | 20 | 10 | 1 | 9 |
| DP1675.09 | 13 | 10 | 0 | 3 |
| DP1675.10 | 10 | 8 | 2 | 0 |
| DP1675.11 | 13 | 11 | 0 | 2 |

TABLE 23-continued

| Seed setting of DP1675 at T1 generation in Beijing (2$^{nd}$ experiment) | | | | |
|---|---|---|---|---|
| | | Seed set | | |
| Line ID | Plant number | Fertility | Semi-sterility | Sterility |
| DP1675.12 | 12 | 6 | 0 | 6 |
| DP1675.13 | 16 | 12 | 0 | 4 |
| DP1675.14 | 13 | 10 | 0 | 3 |
| DP1675.15 | 20 | 15 | 1 | 4 |
| Totally | 247 | 179 | 10 | 58 |

Both pollen and pistil phenotype were observed in the above experiments. The pollen of OsPPT1-1 transgenic rice plants were fertile (FIG. 9), and no abnormal phenotype in pistils was observed with OsPPT1-1 transgenic rice plants. During the field experiments, except for a few individual plants, most of the transgenic rice plants had only a sterile phenotype, and the other phenotypes, include but not limit to, plant height, growth period, yield etc., were normal.

To understand if the phenotypes were impacted by locations and/or environmental factors, the stubbles of OsPPT1-1 transgenic rice were transferred from Beijing to Hainan in October. The pollen of 11 sterile plants at T1 generation were examined by microscope, and the panicles were bagged to measure the seed setting rate. As indicated in table 24, the pollen were fertile and semi-sterile. This might be influenced by the low temperature in Hainan at the stages of booting and/or flowering. Except DP1675.08 line, the seed setting rate of all the other lines were sterile. In a word, the pollen from all plants are fertile or semi-sterile, while the seed setting rate of the bagged plants is sterile or high sterile. The results suggest that OsPPT1-1 is a female-sterile gene.

TABLE 24

| Sterile phenotypes of DP1675 at T1 generation in Hainan (3$^{rd}$ experiment) | | |
|---|---|---|
| Line ID | Seed setting rate of pollen (%) | Seed setting rate of bagged plants (%) |
| DP1675.01 | 25 | 0 |
| DP1675.05-1 | 73 | 0 |
| DP1675.05-2 | 83 | 0 |
| DP1675.07-1 | 57 | 0 |
| DP1675.07-2 | 60 | 0 |
| DP1675.08-1 | 83 | 10 |
| DP1675.08-2 | 82 | 5 |
| DP1675.12-1 | 55 | 0 |
| DP1675.12-2 | 77 | 0 |
| DP1675.13 | 50 | 0 |
| DP1675.14 | 90 | 0 |

2. Fluorescence Segregation Ratio of OsPPT1-1 Transgenic Rice Seeds

The fluorescence segregation ratio of OsPPT1-1 transgenic rice seeds were measured. The seeds of 165 plants from 15 lines at T1 generation were inspected, using 100 seeds from each plant. The results demonstrated that 12449 of 16460 seeds shown red color under green fluorescence light, while 4011 of 16460 seeds didn't show red color. The ratio of red color seeds to normal seeds was 3.1:1. The results indicated that a single OsPPT1-1 gene was inserted in the OsPPT1-1 transgenic rice genome.

3. Cross-Out Results of OsPPT1-1 Transgenic Rice

To further investigate the function of OsPPT1-1 gene, cross-out experiments were performed. The cross-out seeds were validated by PCR with the primers of SEQ ID NO: 24 and SEQ ID NO: 25. The PCR validation results demonstrated that all the cross-out plants contained the OsPPT1-1 gene. The seed setting of the cross-out plants was measured. As shown in table 25, all the plants were fertile.

TABLE 25

| Sees sets of cross-out of DP1675 lines at F1 generation | | | | | |
|---|---|---|---|---|---|
| | | Total | Seed setting | | |
| Line ID | Generation | plant number | Fertility | Semi-sterility | Sterility |
| DP1675.07♂.1-7-F | F1 | 7 | 7 | 0 | 0 |
| DP1675.07♂.1-9-F | F1 | 8 | 8 | 0 | 0 |
| DP1675.07♂.1-2-F | F1 | 10 | 10 | 0 | 0 |
| DP1675.05♂.1-3-F | F1 | 10 | 10 | 0 | 0 |

The seeds showing red color under green florescence light from the F1 generation were planted in Hainan. As shown in table26, the seed setting rate of the cross-out plants were fertile, semi-sterile and sterile panicles; the ratio of fertile panicles to sterile panicles was about 1.4:1. This might be influenced by the low temperature in Hainan at the stages of booting and/or flowering. These results also demonstrate that OsPPT1-1 is likely a recessive female sterile gene.

TABLE 26

| Seed sets of cross-out of DP1675 lines at F2 generation | | | | | |
|---|---|---|---|---|---|
| | | Total | Seed setting | | |
| Line ID | Generation | plant number | Fertility | Semi-sterility | Sterility |
| DP1675.07♂.1-7-1 | F2 | 19 | 8 | 5 | 6 |
| DP1675.07♂.1-7-2 | F2 | 20 | 3 | 9 | 8 |
| DP1675.07♂.1-7-3 | F2 | 20 | 9 | 3 | 8 |
| DP1675.07♂.1-9-1 | F2 | 20 | 5 | 9 | 6 |
| DP1675.07♂.1-9-2 | F2 | 20 | 2 | 13 | 5 |
| DP1675.07♂.1-9-3 | F2 | 20 | 0 | 9 | 11 |
| DP1675.07♂.1-2-1 | F2 | 20 | 9 | 9 | 2 |
| DP1675.07♂.1-2-2 | F2 | 20 | 6 | 5 | 9 |
| DP1675.07♂.1-2-3 | F2 | 20 | 12 | 5 | 3 |
| DP1675.05♂.1-3-1 | F2 | 20 | 17 | 3 | 0 |
| DP1675.05♂.1-3-2 | F2 | 20 | 14 | 2 | 4 |
| DP1675.05♂.1-3-3 | F2 | 20 | 10 | 8 | 2 |
| Totally | | 239 | 95 | 80 | 64 |

What is claimed is:

1. A polynucleotide, wherein said polynucleotide comprises:

a nucleotide sequence encoding a polypeptide with an amino acid sequence of at least 95% identity to SEQ ID NO: 41;

wherein increasing expression of the polynucleotide in a plant confers female sterility to the plant, wherein said polynucleotide is operably linked to at least one heterologous regulatory element.

2. A method of making a female sterile plant for use in hybrid seed production, the method comprising increasing the expression of the polynucleotide of claim 1 in a plant to confer female sterility; and pollinating the female-sterile plant with pollen from a second plant, thereby producing hybrid seed.

3. The method of claim 2, wherein the female sterile plant is a rice, maize, or wheat plant.

* * * * *